US009339202B2

(12) United States Patent
Brockway et al.

(10) Patent No.: US 9,339,202 B2
(45) Date of Patent: May 17, 2016

(54) SYSTEM FOR PROCESSING PHYSIOLOGICAL DATA

(71) Applicant: VivaQuant LLC, St. Paul, MN (US)

(72) Inventors: Marina Brockway, St. Paul, MN (US); Brian Brockway, St. Paul, MN (US)

(73) Assignee: VivaQuant LLC, St. Paul, MN (US)

( * ) Notice: Subject to any disclaimer, the term of this patent is extended or adjusted under 35 U.S.C. 154(b) by 38 days.

(21) Appl. No.: 13/931,228

(22) Filed: Jun. 28, 2013

(65) Prior Publication Data
US 2013/0289424 A1 Oct. 31, 2013

Related U.S. Application Data

(63) Continuation-in-part of application No. 13/092,530, filed on Apr. 22, 2011, now Pat. No. 8,478,389, which is a continuation-in-part of application No. 12/938,995, filed on Nov. 3, 2010, now Pat. No.
(Continued)

(51) Int. Cl.
*A61B 5/00* (2006.01)
*A61B 5/0402* (2006.01)
*A61B 5/0205* (2006.01)
*A61B 5/0456* (2006.01)

(52) U.S. Cl.
CPC ............ *A61B 5/0402* (2013.01); *A61B 5/0002* (2013.01); *A61B 5/0205* (2013.01); *A61B 5/0456* (2013.01); *A61B 5/7203* (2013.01)

(58) Field of Classification Search
CPC ............... A61B 5/0402; A61B 5/0424; A61B 5/0408–5/0416
See application file for complete search history.

(56) References Cited

U.S. PATENT DOCUMENTS

| | | |
|---|---|---|
| 5,090,418 A | 2/1992 | Squires et al. |
| 5,521,851 A | 5/1996 | Wei et al. |
| 5,792,065 A | 8/1998 | Xue et al. |
| 5,817,027 A | 10/1998 | Arand et al. |
| 5,827,195 A | 10/1998 | Lander |
| 5,987,352 A | 11/1999 | Klein et al. |

(Continued)

FOREIGN PATENT DOCUMENTS

WO 2013/043157 A2 3/2013

OTHER PUBLICATIONS

B. Widrow, et al., "Adaptive noise cancelling: principles and applications," IEEE Proc., vol. 63, No. 12, pp. 1692-1716, Dec. 1975.
(Continued)

*Primary Examiner* — Scott Getzow
(74) *Attorney, Agent, or Firm* — Crawford Maunu PLLC

(57) ABSTRACT

Physiological signals such as ECG signals are obtained from a patient. In accordance with one or more embodiments, an apparatus, system and/or method is directed to at least two ECG sensing electrodes that adhere to remote locations on a patient and sense ECG signals from the patient. An amplifier circuit amplifies the sensed ECG signals to provide amplified ECG signals, and a digitizing circuit digitizes the amplified ECG. A computing circuit processes the digitized ECG signals (e.g., by removing noise). A battery powers the aforesaid circuits, and a housing houses the battery and aforesaid circuit. A fastener mechanically fastens and electrically couples the housing to one of the electrodes, and the other electrodes are coupled to the amplifier via a flexible insulated lead wire.

21 Claims, 20 Drawing Sheets

Related U.S. Application Data 8,632,465, which is a continuation-in-part of application No. PCT/US2013/024770, filed on Feb. 5, 2013, which is a continuation-in-part of application No. PCT/US2011/052371, filed on Sep. 20, 2011.

(60) Provisional application No. 61/327,497, filed on Apr. 23, 2010, provisional application No. 61/257,718, filed on Nov. 3, 2009, provisional application No. 61/366,052, filed on Jul. 20, 2010.

(56) References Cited

U.S. PATENT DOCUMENTS

| | | | |
|---|---|---|---|
| 6,117,077 A * | 9/2000 | Del Mar et al. | 600/301 |
| 6,389,308 B1 | 5/2002 | Shusterman | |
| 6,589,189 B2 | 7/2003 | Meyerson et al. | |
| 6,690,959 B2 | 2/2004 | Thompson | |
| 6,701,170 B2 | 3/2004 | Stetson | |
| 6,822,564 B2 | 11/2004 | Al-Ali | |
| 6,856,832 B1 * | 2/2005 | Matsumura et al. | 600/523 |
| 7,096,060 B2 | 8/2006 | Arand et al. | |
| 7,115,096 B2 | 10/2006 | Siejko et al. | |
| 7,236,819 B2 | 6/2007 | Brockway et al. | |
| 7,272,265 B2 | 9/2007 | Kouri et al. | |
| 7,376,453 B1 | 5/2008 | Diab et al. | |
| 7,627,369 B2 | 12/2009 | Hunt | |
| 7,672,717 B1 * | 3/2010 | Zikov et al. | 600/544 |
| 7,840,259 B2 | 11/2010 | Xue et al. | |
| 8,086,304 B2 | 12/2011 | Brockway et al. | |
| 8,214,007 B2 | 7/2012 | Baker et al. | |
| 8,271,073 B2 | 9/2012 | Zhang et al. | |
| 8,348,852 B2 | 1/2013 | Bauer et al. | |
| 8,460,189 B2 * | 6/2013 | Libbus et al. | 600/301 |
| 8,478,389 B1 | 7/2013 | Brockway et al. | |
| 2004/0073125 A1 * | 4/2004 | Lovett | A61B 5/7203 600/509 |
| 2005/0010120 A1 | 1/2005 | Jung et al. | |
| 2005/0234361 A1 | 10/2005 | Holland | |
| 2005/0283090 A1 | 12/2005 | Wells | |
| 2006/0094992 A1 * | 5/2006 | Imboden et al. | 601/70 |
| 2007/0219453 A1 | 9/2007 | Kremliovsky et al. | |
| 2007/0219455 A1 | 9/2007 | Wong et al. | |
| 2007/0260151 A1 | 11/2007 | Clifford | |
| 2007/0265508 A1 | 11/2007 | Sheikhzadeh-Nadjar | |
| 2008/0065158 A1 | 3/2008 | Ben-Ezra et al. | |
| 2008/0097537 A1 | 4/2008 | Duann et al. | |
| 2008/0183093 A1 | 7/2008 | Duann et al. | |
| 2008/0200832 A1 | 8/2008 | Stone | |
| 2009/0069703 A1 | 3/2009 | Takla et al. | |
| 2009/0222262 A1 | 9/2009 | Kim et al. | |
| 2010/0063438 A1 * | 3/2010 | Bengtsson | 604/66 |
| 2012/0165691 A1 | 6/2012 | Ting et al. | |
| 2012/0197144 A1 | 8/2012 | Christ et al. | |
| 2012/0232417 A1 | 9/2012 | Zhang | |
| 2013/0069768 A1 * | 3/2013 | Madhyastha et al. | 340/12.5 |
| 2013/0109937 A1 | 5/2013 | Banet et al. | |
| 2014/0005988 A1 | 1/2014 | Brockway | |

OTHER PUBLICATIONS

H. Boudoulas, YH. Sohn, W. O'Neill, R. Brown, AM. Weissler. The QT greater that QS2 syndrome: a new mortality risk indicator in coronary artery disease. American Journal of Cardiology, vol. 50 (6) pp. 1229-1235 (1982).Unavailable).
G. Moody, W. Muldrow, and R. Mark, "A noise stress test for arrhythmia detectors," Computers in Cardiology, pp. 381-384 (1984).
K. R. Rao and P. Yip, "Discrete Cosine Transform: Algorithms, Advantages, Applications," San Diego, CA: Academic (1990).
J. Woods. Subband Coding, Kluwer Academic Press (1990).
K. Ball, L. Sirovich, and L. Keefe, "Dynamical Eigenfunction Decomposition of Turbulent Channel Flow," International Journal for Numerical Methods in Fluids, vol. 12, Issue 6, pp. 585-604 (Apr. 1991).
NV Thakor and YS Zhu, "Applications of adaptive filtering to ECG analysis: noise cancellation," IEEE Transactions on Biomedical Engineering, vol. 38, No. 8, pp. 785-794 (Aug. 1991).
S. Mallat and W. L.-Hwang, "Singularity Detection and Processing with Wavelets," IEEE Transactions on Information Technology (38), pp. 617-643 (1992).
S. Mallat and S. Zhong, "Characterization of Signals from Multiscale Edges," IEEE Trans. Pattern Anal. Mach. Intell. 14, 7 (Jul. 1992).
Vaidyanathan, Multirate Systems and Filter Banks, Prentice Hall, 1993.
Y. Pati, R. Rezaiifar and P. Krishnaprasad, "Orthogonal Matching Pursuit: Recursive Function Approximation With Applications to Wavelet Decomposition," in Asilomar Conference on Signals, Systems and Computers, vol. 1, pp. 40-44 (Nov. 1993).
S. Mallat and Z. Zhang, "Matching Pursuits with Time-Frequency Dictionaries," IEEE TSP(41), No. 12, pp. 3397-3415 (Dec. 1993).
P. Comon, "Independent component analysis, a new concept?," Signal Process. Special Issue on Higher Order Statistics, vol. 36, No. 3, pp. 287-314 (Apr. 1994).
Donoho, D.L., I.M. Johnstone (1994), "Ideal spatial adaptation by wavelet shrinkage," Biometrika, vol. 81, pp. 425-455.
Y. Xu, J. Weaver, D. Healy, Jr. and J. Lu, "Wavelet Transform Domain Filters: A Spatially Selective Noise Filtration Technique," IEEE Transactions on Image Processing, vol. 3, No. 6, pp. 747-758 (1994).
D. L. Donoho, "Denoising by Soft-Thresholding," IEEE Trans. on Inf. Theory, vol. 41, No. 3, pp. 613-627 (May 1995).
A.Bell and T. Sejnowski, "An Information-Maximization Approach to Blind Separation and Blind Deconvolution," Neural Computation, 7:1129-1159. (1995).
M. Haugland and T. Sinkjaer, "Cutaneous Whole Nerve Recordings Used for Correction of Footdrop in Hemiplegic Man," IEEE Transactions on Rehabilitation Engineering, vol. 3, No. 4. pp. 207-317 (Dec. 1995).
V. Afonso, W. Tompkins, T. Nguyen, K. Michler and S. Luo, "Comparing Stress ECG Enhancement Algorithms," IEEE in Medicine and Biology, Engineering iology, pp. 37-44 (May/Jun. 1996).
J._Francois Cardoso, "Infomax and Maximum Likelihood for Source Separation," IEEE Letters on Signal Processing, vol. 4, No. 4, pp. 112-114 (Apr. 1997).
M. L. Hilton, "Wavelet and Wavelet Packets Compression of Electrocardiogram," IEEE Transactions on Biomedical Engineering, vol. 44, No. 5, pp. 394-402 (May 1997).
A. Hyvärinen, "New Approximations of Differential Entropy for Independent Component Analysis and Projection Pursuit," in Advances in Neural Information Processing Systems, vol. 10, pp. 273-279, MIT Press. (1997).
W. Sweldens. The lifting scheme: A construction of second generation wavelets. SIAM J. Math. Anal., 29(2):511-546, 1997.
American National Standard ANSI/AAMI EC57:1998, Testing and Reporting Performance Results of Cardiac Rhythm and ST Segment Measurement Algorithms.
Testing and reporting performance results of cardiac rhythm and ST-segment measurement algorithms ANSI/AAMI EC57:1998.
L. Torres-Pereira, et. al. "A Biotelemetric Heart Sound Monitoring System," in Proceedings of the 14th International Symposium on Biotelemetry. Marburg, 1998.
A. Hyvärinen, "Fast and Robust Fixed-Point Algorithms for Independent Component Analysis," IEEE Transactions on Neural Networks, vol. 10, No. 3, pp. 626-634 (May 1999).
J.-F. Cardoso, "High-Order Contrasts for Independent Component Analysis," Neural Comput., vol. 11, No. 1, pp. 157-192 (1999).
S. Chen, D Donoho, and M. Saunders, "Atomic Decomposition by Basis Pursuit," SIAM J. Scientific Computing, vol. 20, No. 1, pp. 33-61 (1999).
Q. Pan, L. Zhang, G. Dai and H. Zhang, "Two Denoising Methods by Wavelet Transform," IEEE Trans. on SP, vol. 47, No. 12, pp. 3401-3406 (Dec. 1999).
G. Michaud, Q. Li, X. Costeas, R. Stearns, M. Estes, and PJ Wang, "Correlation waveform analysis to discriminate monomorphic ventricular tachycardia from sinus rhythm using stored electrograms from implantable defibrillators," PACE. Aug. 1999; 22(8):1146-51 (1999).

(56) References Cited

OTHER PUBLICATIONS

S. Mallat, "A Wavelet Tour of Signal Processing," Academic Press, 1999.
Langley, P.; Di Bernardo, D.; Murray, A.; Comparison of three measures of QT dispersion. Computers in Cardiology 1999 pp. 69-72.
Goldberger AL et al. PhysioBank, PhysioToolkit, and PhysioNet: components of a new research resource for complex physiologic signals. Circulation 101(23): e215-e220, (Jun. 13, 2000).
Z. Lu, D. Kim, and W. Pearlman, "Wavelet Compression of ECG Signals by the Set Partitioning in Hierarchical Trees Algorithm," IEEE Transactions on Biomedical Engineering, vol. 47, No. 7, pp. 849-856 (Jul. 2000).
M. Marcellin, M. gormish, A. Bilgin and M. Boleik, "An Overview of JPEG-2000," Proc. of IEEE Data Compression Conference, pp. 523-541 (2000).
L. K. Saul and J. B. Allen, "Periodic component analysis: An eigenvalue method for representing periodic structure in speech," in NIPS, [Online],, pp. 807-813 (2000). Available: http://www.cs.cmu.edu/Groups/NIPS/00papers-pub-on-web/SaulAllen.pdf.
C. Taswell, "The What, How, and Why of Wavelet Shrinkage Denoising," Computing in Science and Engineering, vol. 2, No. 3, pp. 12-19 (2000).
J. S. Richman and J. R. Moorman, Physiological time-series analysis using approximate entropy and sample entropy Am. J. Physiol. 278, H2039 (2000).
K. Sayood, "Introduction to Data Compression," Academic Press 2000.
Malik M, Batchvarov VN. Measurement, interpretation and clinical potential of QT dispersion. J Am Coll Cardiol. Nov. 15, 2000;36(6):1749-66.
A. Hyvärinen and E. Oja, "Independent Component Analysis: Algorithms and Applications," Neural Networks, 13(4-5), pp. 411-430 (2000).
R. Mayerburg. Sudden cardiac death: exploring the limits of our knowledge. Journal of Cardiovascular Electrophysiology, vol. 12, No. 3, Mar. 2001.
M. Brennan, M. Palaniswami, and P. Kamen. Do Existing Measures of Poincaré Plot Geometry Reflect Nonlinear Features of Heart Rate Variability? IEEE Transactions on Biomedical Engineering, vol. 48, No. 11, Nov. 2001.
D. Donoho and X. Huo, "Uncertainty Principles and Ideal Atomic Decomposition," IEEE Transactions on Information Theory, vol. 47, No. 7, pp. 2845-2862 (Nov. 2001).
M. Zibulevsky and B. Pearlmutter, "Blind Source Separation by Sparse Decomposition in a Signal Dictionary," Neural Computation. vol. 13, pp. 863-882 (2001).
Oweiss, K.G. Anderson, D.J. "MASSIT—Multiresolution Analysis of Signal Subspace Invariance Technique: a novel algorithm for blind source separation", Conference on Signals, Systems and Computers Publication Date: 2001 vol. 1, pp. 819-823 vol. 1.
M. Costa, A. L. Goldberger, and C.-K. Peng, Multiscale Entropy Analysis of Complex Physiologic Time Series, Phys. Rev. Lett. 89, 6, (2002).
B. U. Kohler, C. Hennig, R. Orglmeister. The principles of software QRS detection. IEEE Engineering in Medicine and Biology Magazine, vol. 21, No. 1. (2002), pp. 42-57.
Tsalaile, et al. "Blind Source Extraction of Heart Sound Signals From Lung Sound Recordings Exploiting Periodicity of the Heart Sound," ICASSP 2008 IEEE, p. 461-464.
G.-J. Jang, T.-W. Lee and Y.-H Oh, "Single-Channel Signal Separation Using Time-Domain Basis Functions," IEEE Signal Processing Letters, vol. 10, No. 6, pp. 168-171 (Jun. 2003).
T. Blaschke and L. Wiskott, "Cubica: Independent Component Analysis by Simultaneous Third- and Fourth-Order Cumulant Diagonalization," IEEE Transactions on Signal Processing, vol. 52, No. 5, pp. 1250-1256 (May 2004).
D A Clunie, "Extension of an open source DICOM toolkit to support SCP-ECG waveforms," 2nd OpenECG Workshop 2004, Berlin, Germany.
J.-P Martinez, et. al., "A wavelet-based ECG delineator: Evaluation on standard databases," IEEE transactions on biomedical engineering, vol. 51, No. 4, pp. 57 (2004).
Thomsen, M. B., Verduyn, S. C., Stengl, M., Beekman, J. D., de Pater, G., van Opstal, J., et al. (2004). Increased short-term variability of repolarization predicts d- sotalolinduced torsade de pointes in dogs. Circulation, 110, 2453-2459.
Malik M, Hnatkova K, Batchvarov V, Gang Y, Smetana P, Camm AJ. Sample size, power calculations, and their implications for the cost of thorough studies of drug induced QT interval prolongation. Pacing Clin Electrophysiol. Dec. 2004;27(12):1659-69.
Madalena Costa.et. al. Multiscale entropy analysis of biological signals. Physical Review E 71, 021906 s2005d.
M. Alghoniemy and A. Tewfik, "Reduced Complexity Bounded Error Subset Selection," IEEE Int. Conf. Acoustics, Speech and Signal Processing (ICASSP), pp. 725-728 (Mar. 2005).
S.-C. Tai, C.-C. Sun and W.-C Yan, "2-D ECG Compression Method Based on Wavelet Transform and Modified SPIHT," IEEE Trans. Biomed. Eng., vol. 52, No. 6, pp. 999-1008 (Jun. 2005).
Hamlin RL. Non-drug-related electrocardiographic features in animal models in safety pharmacology. J Pharmacol Toxicol Methods. Jul.-Aug. 2005; 52(1): 60-76.
HJ van der Linde, A van Water, W Loots, B van Dueren, K van Ammel, M Peters and DJ Gallacher. A new method to calculate the beat-to-beat instability of QT duration in drug-induced long QT in anesthetized dogs. Journal of Pharmacological and Toxicological Methods 52 (2005) 168-177.
R. Sameni, MB Shamsollahi, C. Jutten, and M. Babaie-Zadeh, "Filtering Noisy ECG Signals Using the Extended Kalman Filter Based on a Modified Dynamic ECG Model," Computers in Cardiology, pp. 1017-1020 (2005).
M. Blanco-Velasco, B. Weng and Ke Barner, "A New ECG Enhancement Algorithm for Stress ECG Tests," Computers in Cardiology, vol. 33, pp. 917-920 (2006).
Chen PC, Lee S, Kuo CD. Delineation of T-wave in ECG by wavelet transform using multiscale differential operator. IEEE Trans Biomed Eng. Jul. 2006;53(7):1429-33.
K. Zhang, L.-W. Chan, "An Adaptive Method for Subband Decomposition ICA", Neural Computation, vol. 18, No. 1, pp. 191-223 (2006).
R. Brychta, "Wavelet analysis of autonomic and cardiovascular signals," PhD Dissertation. Vanderbilt University (Aug. 2006).
M. Aminghafari, N. Cheze, J.-M Poggi, "Multivariate de-noising using wavelets and principal component analysis," Computational Statistics & Data Analysis, 50, pp. 2381-2398 (2006).
Aharon, M. Elad and A. Bruckstein, "K-SVD: An Algorithm for Designing Overcomplete Dictionaries for Sparse Representation," IEEE Transactions on Signal Processing, vol. 54, No. 11, pp. 4311-4322 (Nov. 2006).
Chouakri S.A., et al. ECG signal smoothing based on combining wavelet denoising levels. Asian Journal of Information Technology. vol. 5, pp. 667-677. 2006.
Inan, O.T.; Giovangrandi, L.; Kovacs, G.T.A.; Robust Neural-Network-Based Classification of Premature Ventricular Contractions Using Wavelet Transform and Timing Interval Features , IEEE Transactions on Biomedical Engineering vol. 53 , Issue: 12 , pp. 2507-2515.
L. Smith, A tutorial on Principal Components Analysis.
Akinori Ueno, et al. Capacitive sensing of electrocardiographic potential through cloth from the dorsal surface of the body in a supine position: a preliminary study. IEEE Transactions on Biomedical Engineering, vol. 54, No. 4, Apr. 2007, pp. 759-766.
K. Oweiss , A. Mason , Y. Suhail , A. Kamboh and K. Thomson, "A Scalable Wavelet Transform VLSI Architecture for Real-Time Signal Processing in High-Density Intra-Cortical Implants", IEEE Trans. Circuits Syst. I, vol. 54, No. 6, pp. 1266-1278 (Jun. 2007).
K. Todros and J. Tabrikian, "Blind Separation of Independent Sources Using Gaussian Mixture Model," IEEE Transactions on Signal Processing, vol. 55, No. 7, pp. 3645-3658 (Jul. 2007).
R. Sameni, M. Shamsollahi, C. Jutten and G. Glifford, "A Nonlinear Bayesian Filtering Framework for ECG Denoising," IEEE Transactions on Biomedical Engineering , vol. 54, No. 12, pp. 2172-2185 (2007).

(56) References Cited

OTHER PUBLICATIONS

X. Li, X. Yao, J. Fox, and J. Jefferys, "Interaction Dynamics of Neuronal Oscillations Analysed Using Wavelet Transforms," Journal of Neuroscience Methods 160, pp. 178-185 (2007).

R Schimpf, CH Antzelevitch, D Haghi, C Giustetto, A Pizzuti, F Gaita, Ch Veltmann, Ch Wolpert, and M Borggrefe. Electromechanical coupling in patients with the short QT syndrome: Further insights into the mechanoelectrical hypothesis of the U wave. Heart Rhythm. Feb. 2008 ; 5(2): 241-245.

Sarkar S, Ritscher D, Mehra R. A detector for a chronic implantable atrial tachyarrhythmia monitor. IEEE Trans Biomed Eng. Mar. 2008;55(3):1219-24.

M. Malik, K. Hnatkova, T. Novotny, G Schmidt Subject-specific profiles of QT/RR hysteresis. Am J Physiol Heart Circ Physiol 295:H2356-H2363, 2008.

Akturk, A. and Goldsman, N. (2008) "Electron transport and full-band electron phonon interactions in graphene" J. of Applied Physics 103.

S. Paredes, T. Rocha, P. de Carvalho, and J. Henriques, "Atrial Activity Detection through a Sparse Decomposition Technique," vol. 2, pp. 358-362, 2008 International Conference on BioMedical Engineering and Informatics, 2008.

R. Sameni, C. Jutten and M. Shamsollahi, "Multichannel Electrocardiogram Decomposition Using Periodic Component Analysis," IEEE Transactions on Biomedical Engineering, vol. 55, No. 8, pp. 1935-1940 (Aug. 2008).

O. Adeyemi, et. al., "QA interval as an indirect measure of cardiac contractility in the conscious telemeterised rat: Model optimisation and evaluation," Journal of Pharmacological and Toxicological Methods. 60, pp. 159-166 (2009).

H. Li, R. Li, F. Wang. Multiresolution Subband Blind Source Separation: Models and Methods. Journal of Computers, vol. 4, No. 7 (2009), 681-688.

Afonso, V.X.; Tompkins, W.J.; Detecting ventricular fibrillation. IEEE Engineering in Medicine and Biology Magazine, vol. 14 , Issue: 2, pp. 152-159.

Dash S, Chon KH, Lu S, Raeder EA. Automatic real time detection of atrial fibrillation. Ann Biomed Eng. Sep. 2009;37 9):1701-9. Epub Jun. 17, 2009.

M. Hassan, J. Terrien, B. Karlsson, and C. Marque, "Spatial Analysis of Uterine EMG Signals: Evidence of Increased in Synchronization With Term," Conf Proc IEEE Eng Med Biol Soc, vol. 1, pp. 6296-6299 (Sep. 2009).

R. Yang, Y. Qin, C. Li, G. Zhu, Z. Lin Wang, "Converting Biomechanical Energy into Electricity by a Muscle-Movement-Driven Nanogenerator," Nano Letters, vol. 9, No. 3, pp. 1201-1205 (2009).

J. Piccini, et al, Predictors of sudden cardiac death change with time after myocardial infarction: results from the Valiant trial. European Heart Journal (2009).

J. Lipponen, M. Tarvainen, T. Laitinen, T. Lyyra-Laitinen, and P.A. Karjalainen, "Principal Component Regression Approach for Estimation of Ventricular Repolarization Characteristics," IEEE Trans Biomed Eng., vol. 57, No. 5, pp. 1062-1069 (2010).

S.Hadei, M. Iotfizad. A family of adaptive filter algorithms in noise cancellation for speech enhancement. International Journal of Computer and Electrical Engineering, vol. 2, No. 2, Apr. 2010. 1793-8163.

Allen, M., Tung, V., Kaner, R. (2010) "Honey Carbon: A Review of Graphene" Chem. Rev. 110:132-145.

Attila S. Farkas. et. al. Biomarkers and endogenous determinants of dofetilide-induced torsades de pointes in $\alpha$1-adrenoceptor-stimulated, anaesthetized rabbits. British Journal of Pharmacology. vol. 161, Issue 7, pp. 1477-1495, Dec. 2010.

HJ van der Linde, B Van Deuren, Y Somers, B Loenders, R Towart and DJ Gallacher, The Electro-Mechanical window: a risk marker for Torsade de Pointes in a canine model of drug induced arrhythmias, British Journal of Pharmacology (2010) 161 1444-1454.

Daubechies I., et al. Synchrosqueezed wavelet transforms: an empirical mode decomposition-like tool. Applied and Computational Harmonic Analysis, vol. 30, Issue 2, Mar. 2011, pp. 243-261.

M. Brockway and R Hamlin, "Evaluation of an algorithm for highly automated measurements of QT interval," Journal of Pharmacological and Toxicological Methods, vol. 64, pp. 16-24 (2011).

http://www.physionet.org/physiobank/database/#ecg.

http://www.physionet.org/physiobank/database/mitdb/.

Ghasemi, M, SadAbadi, H "A Semi-Automated QT Interval Measurement Based on Wavelet and Energy Analysis," http://physionet.org/challenge/2006/papers/.

Jungwirth B, Mackensen GB, Blobner M, Neff F, Reichart B, Kochs EF, Nollert G: Neurologic outcome after cardiopulmonary bypass with deep hypothermic circulatory arrest in rats: description of a new model. J Thorac Cardiovasc Surg 2006, 131:805-812.

SadAbadi H, Ghasemi M, Ghaffari A, "A mathematical algorithm for ECG signal denoising using window analysis," Biomed Pap Med Fac Univ Palacky Olomouc Czech Repub. Jun. 2007;151(1):73-8.

Sameni, R., Jutten, C. and Shamsollahi, M. B., "Multichannel electrocardiagram decomposition using periodic component analysis", IEEE Trans. Biomed. Eng., vol. 55, No. 8, pp. 1935-1940 2008.

Kellermann, et al.,"A mobile phone based alarm system for supervising vital parameters in free moving rats," BMC Research Notes 2012, 5:119, Feb. 23, 2012.

http://www.simplehelp.net/2006/09/12/how-to-set-up-outlook-2003-for-email/.

* cited by examiner

Figure 1 – Physiological Monitoring System Diagram

Figure 3 - Data Collection and Review System and Remote Communicator

Figure 4 - High level TAMD signal flow

Figure 5 – Identification and Validity Evaluation of Feature Points and Events

Figure 6 – Computing Parameters

Figure 10 - Signal flow - EEG

Figure 11 - Signal flow - Peripheral Nerve Activity (PNA)

Figure 12 – System for Reporting Arrhythmia Information

Figure 13 – Decision Flow for Detecting, Classifying, and Reporting Arrythmia Events Figure 14 – Compression Data Flow Event classification breakdown Figure 21
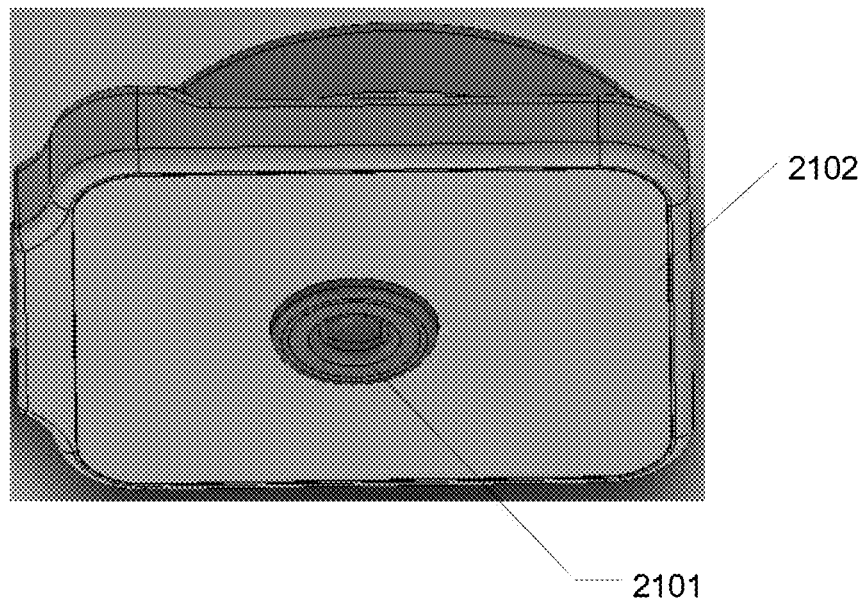
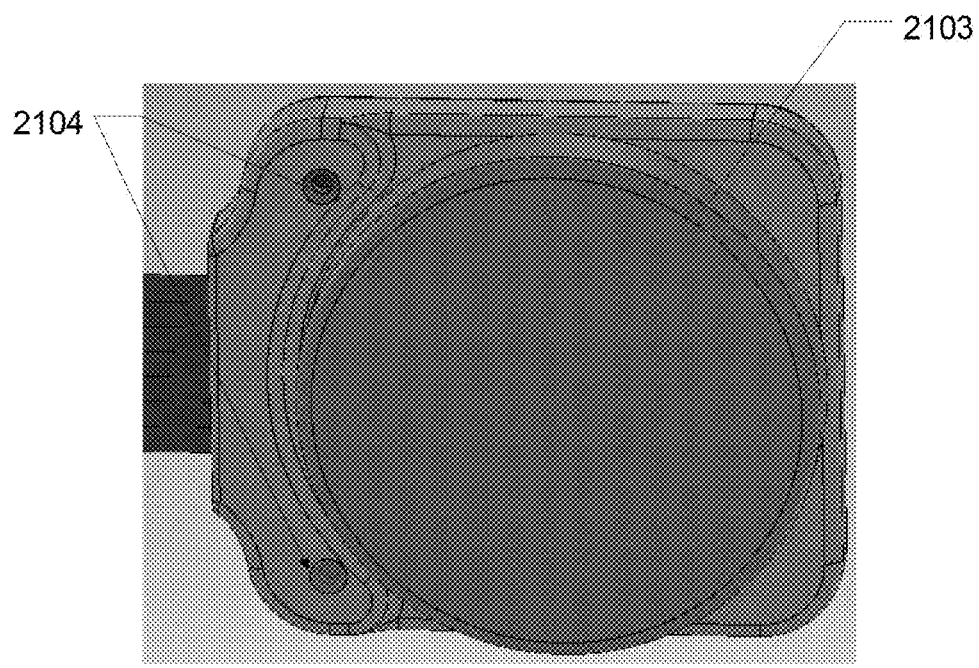

SYSTEM FOR PROCESSING PHYSIOLOGICAL DATA

RELATED PATENT DOCUMENTS

This patent document is a continuation-in-part under 35 U.S.C. §120 of U.S. patent application Ser. No. 13/092,530 filed on Apr. 22, 2011 (U.S. Pat. No. 8,478,389), which claims benefit under 35 U.S.C. §119 to U.S. Provisional Patent Application Ser. No. 61/327,497, entitled "System and Method for Monitoring Physiological Data of Subjects" and filed on Apr. 23, 2010; this patent document is also a continuation-in-part of U.S. patent application Ser. No. 12/938,995 (U.S. Pat. No. 8,632,465), entitled "Physiological Signal Denoising," and filed on Nov. 3, 2010, to which priority is claimed under 35 U.S.C. §120 for common subject matter; Ser. No. 12/938,995 (U.S. Pat. No. 8,632,465) claims benefit under 35 U.S.C. §119 to U.S. Provisional Patent Application Ser. No. 61/257,718 filed on Nov. 3, 2009, and to Ser. No. 61/366,052 filed on Jul. 20, 2010; this patent document is also a continuation-in-part of PCT/US2013/024770 filed on Feb. 5, 2013; this patent document is also a continuation-in-part of PCT/US2011/052371 filed on Sep. 20, 2011; all of these patent documents, the references cited therein and any applications to which priority is claimed therein are fully incorporated herein by reference.

FIELD OF INVENTION

The present invention relates to monitoring of physiological signals, and more particularly, a system for monitoring ambulatory animals and human beings.

BACKGROUND

Implantable and external wireless devices have been used to monitor physiologic signals in humans and animals for clinical care and in research studies. For example, wireless devices that measure electrocardiogram and blood pressure are routinely used to assess cardiovascular function in animal research models. Wireless ECG monitoring devices are also routinely used to monitor subjects in human clinical studies and for diagnosis of arrhythmias. Information extracted from the measured signal can be used to assess the physiological status and/or health of a monitored subject as well as the safety and clinical utility of experimental therapies such as pharmaceuticals.

Research study protocols and clinical care regimens using conventional systems may require that the waveform be communicated from the subject to a data collection system and archived for post hoc evaluation if a researcher or clinician has concern that information may not have been extracted properly. However, communicating the waveform may require significant power and processing resources. Ensuring the accuracy and reliability of information provided by these systems can be challenging. In addition, the size, power required and other characteristics of such systems have also been challenging to their implementation.

SUMMARY

Various aspects of the present invention are directed to devices, methods and systems involving physiological monitoring and signal processing, in a manner that addresses challenges and limitations including those discussed above.

According to an example embodiment, an apparatus includes two or more ECG sensing electrodes, digitizing and computing circuits, a housing that houses the digitizing and computing circuits, a fastener that mechanically fastens and electrically couples the housing to one of the electrodes, and a lead wire that couples the other one(s) of the electrodes to the digitizing circuit. The electrodes adhere to remote locations on a patient and sense ECG signals therefrom, and couple the signals to the digitizing circuit via the fastener or the lead wire(s). The digitizing circuit digitizes the ECG signals, and the computing circuit processes the digitized ECG signals by one or more of removing noise, detecting an R-R interval, detecting a Q-T interval, and detecting a QRS complex.

Another example embodiment is directed to a patient-worn apparatus for recording an ECG from the patient. The apparatus includes a first circuit that digitizes an ECG signal obtained from the patient via at least two ECG leads, and a computing circuit that is connected to the first circuit to receive the digitized ECG signal. The computing circuit decomposes the digitized ECG signal into subcomponents, computes a statistical variance of the subcomponents over a time interval, and determines if one of the at least two ECG leads is disconnected from the patient based upon the statistical variance of the subcomponents.

Another example embodiment is directed to an apparatus including a sensing electrode that adheres to and senses physiological signals from a patient, a denoising component and a fastener that fastens the denoising component to the sensing electrode. The denoising component includes a housing having a digitizing circuit, a computer circuit and a battery. The digitizing circuit digitizes the signals received via the sensing electrode and at least another sensing electrode coupled to the patient, the computing circuit processes the digitized signals to remove noise therefrom, and the battery powers the digitizing and computing circuits. The fastener mechanically fastens the housing to the sensing electrode, which supports the weight of the denoising component via the fastener while the first sensing electrode is adhered to the patient.

In other embodiments, a parameter value is computed for a segment of a cardiac-related signal. Cardiac cycles within the segment are identified, and at least one feature point is identified within said cardiac cycles. For each of the identified feature points, a signal-to-noise ratio (SNR) representative of the ratio of signal energy to noise energy is computed for a cardiac cycle subsegment containing the identified feature point. A validity characteristic of the feature point is determined as a function of said signal-to-noise ratio. Feature points contained within said segment are combined based upon the determined validity characteristics of the feature points, with the combined feature points used to compute/form a parameter value.

According to another example embodiment, physiological signals of a subject human or animal are collected, preprocessed and digitized by a telemetric ambulatory monitoring device (TAMD) that is worn by the subject. The digitized signal is denoised using one of several signal processing algorithms, a feature signal is created from the denoised signal, physiologic events are detected, and the denoised signal is compressed to reduce the data volume in order to reduce the energy required to telemeter the signal. A confidence signal is computed that provides a metric of the validity of points comprising the feature signal. An additional confidence signal is computed to evaluate the validity of detected events. The monitoring device includes a wireless communication module to communicate information to and from a data review system. Further, a process is described for detecting, classifying, and reporting arrhythmia events that provides for efficiency and accuracy.

In one aspect of this invention, a component of computing the confidence signal is a dynamic signal-to-noise ratio (dSNR) that is updated frequently, and in the case of a cardiac signal, it is updated for each cardiac cycle or portion of the cardiac cycle. Feature points extracted from the denoised signal are classified as valid or invalid and only valid features are used to compute a parameter including a mathematical combination of valid features. dSNR can also be used to identify segments of the physiologic signal that contain no useful information.

In another aspect of this invention, physiologic events are detected. A confidence signal is computed and used to classify a detected event as valid, invalid, or uncertain. Events classified as valid are accepted and included in a report summarizing arrhythmia events without the need for verification by a trained person.

In another aspect of this invention, parameters derived from valid feature points of a physiological signal are computed within the TAMD, thereby reducing the volume of data that must be transmitted, resulting in a net reduction in power consumption and hence longer battery life.

In another aspect of this invention, a peripheral nerve activity signal is denoised, a signal indicative of nerve activity is computed, and a signal indicative of recruitment of nerve fibers by a neural stimulation therapy is computed.

In another aspect of this invention, a data collection and review system (DCRS) is in communication with the TAMD, whereby the DCRS facilitates review of the signals and data received from the TAMD, performs certain statistical analysis and reporting, and manages acquired data.

The above summary is not intended to describe each embodiment or every implementation of the present disclosure. The figures and detailed description that follow more particularly exemplify various embodiments.

BRIEF DESCRIPTION OF THE DRAWINGS

The invention may be more completely understood in consideration of the following detailed description of various embodiments of the invention in connection with the accompanying drawings, in which:

FIG. 21 shows another apparatus including a housing with an integrated snap as discussed herein, in accordance with another example embodiment.

Figure 1:
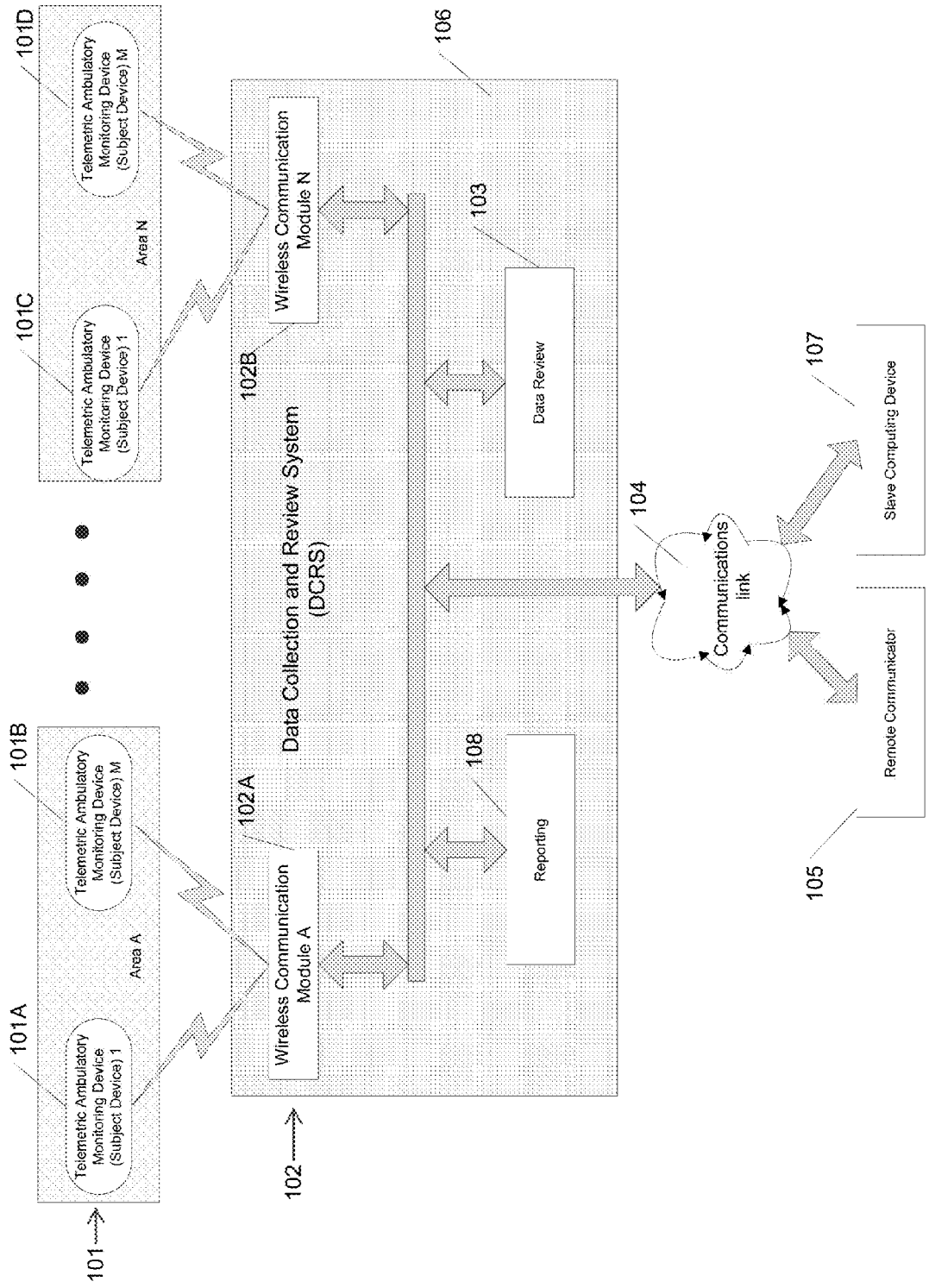
FIG. 1 provides a block diagram of a physiologic monitoring system showing a Telemetric Ambulatory Monitoring Device (TAMD), Data Collection and Review System (DCRS), Remote Communicator, and Slave Computing Device, consistent with one or more example embodiments of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the invention including aspects defined in the claims.

DETAILED DESCRIPTION

Aspects of the present invention relate to a system for wireless monitoring, analysis, evaluation, and/or archival of physiological signals and data from ambulatory animal or human subjects. Various embodiments are directed to monitoring subjects that are part of a research study involving one or more subjects that are within telemetry reception range of each other. In connection with certain embodiments, the accuracy of information provided is improved under a broad range of use scenarios, battery life can be extended, the size of monitoring devices can be reduced, and information can be obtained more efficiently. While the present invention is not necessarily limited to such applications, various aspects of the invention may be appreciated through a discussion of examples using this context.

In the following discussion, reference is made to cited references listed in a numbered order near the end of this document, which are fully incorporated herein by reference. These references may assist in providing general information regarding a variety of fields that may relate to one or more embodiments of the present invention, and further may provide specific information regarding the application of one or more such embodiments.

In accordance with a particular embodiment, an apparatus includes two or more ECG sensing electrodes that adhere to a patient for sensing ECG signals therefrom, a housing having digitizing and computing circuits that process the ECG signals, and a fastener that fastens the housing to one of the electrodes and provides an electrical connection therebetween. The electrodes are adhered to the patient using one or more of a variety of approaches, such as an adhesive applied to the electrode or an integrated adhesive pad. One or more electrical leads couple the housing to each remote electrode to which the housing is not fastened. The digitizing circuit digitizes ECG signals received via the sensing electrodes, and the computing circuit processes the digitized ECG signals (e.g., to remove noise, detect an R-R interval, detect a Q-T interval, or detect a QRS complex).

In various embodiments, a compact arrangement including the housing and the electrode fastened thereto are used to mitigate or eliminate the need to couple each electrode to remote processing devices, which can be cumbersome for patient use. Such approaches may, for example, be facilitated using a signal processing approach as described and/or referenced herein (e.g., denoising) that facilitate an efficient use of circuitry and/or power that, in turn, facilitates the implementation of the housing and circuitry therein in a compact and lightweight component that can be supported by a single electrode. Such an efficient signal processing approach can further facilitate the use of low power and, in turn, lightweight battery supplies which may also be incorporated into the housing. Accordingly, the housing, circuitry and battery can be completely supported by the electrode to which it is fastened, while the electrode is fastened to a patient. For instance, a housing having an average thickness of less than 12 mm and a volume of less than 18 cc is implemented in connection with various embodiments. In some implementations, the housing and electrode are integrated into a common component, such as by including the electrode within the housing and employing the fastener as part of the housing.

The lead wires are implemented using one or more approaches, to suit particular applications. In some embodiments, the flexible insulating lead wires are greater than 10 cm in length, and in other implementations, the flexible insulating lead wires are greater than 15 cm in length. In still other implementations, the flexible insulating lead wires are less than 3 mm in diameter. In further implementations, the electrical leads are replaced with a wireless connection to remote electrodes, each of which is powered by an integrated battery for communicating the wireless signals. Such an approach thus entails two or more self-contained electrodes, one of which incorporates wireless receiving circuitry for coupling to remote electrodes, as well as digitizing and processing circuitry that process ECG signals obtained from the electrodes with desirable accuracy.

The computer circuitry includes one or more of a variety of types of circuits and/or modules operable to carry out one or more processing functions. In some embodiments, the computing circuit processes each digitized ECG signal by decomposing the signal into subcomponents, identifying a location of the QRS complex of a cardiac cycle in the ECG signal, identifying a first time window in the cardiac cycle that includes the QRS complex, and identifying at least one time window in the cardiac cycle that does not include the QRS complex. For each of the identified time windows, the computing circuit identifies target subcomponents as subcomponents that contain more energy that is within the band of frequencies characteristic of a desired ECG signal in the time window than energy that is outside the band of frequencies of the desired ECG signal. The computing circuit then reconstructs a denoised signal from the received ECG signal, using at least two of the identified target subcomponents.

These approaches may, for example, facilitate the processing of the ECG signals in the housing relatively low power. Such an approach can be used to process digitized ECG signals by reducing in-band noise as measured by the ANSI/AAMI EC57:1998 standard by at least 20 dB with a Quality of Signal Reconstruction (QSR) of >95%. Moreover, such an approach can be implemented by sampling each ECG signal at 300 Hz or less, and using the computing circuit to reduce the in-band noise, using an average power consumption that is less than 500 micro-Watts per ECG signal. For further information regarding these methods for denoising subcomponents and their implementation, reference may be made to U.S. patent application Ser. No. 12/938,995 and to PCT Patent Application No. PCT/US2013/024770, which are fully incorporated herein by reference.

The battery as discussed above is implemented using one or more of a variety of approaches. In some embodiments, the battery is a coin cell battery that is included within the housing and powers the digitizing and computing circuits. In some implementations, the housing has a battery compartment that holds the coin cell battery and couples the power therefrom, with the battery compartment having a threaded cap that secures the coin cell battery therein.

In some embodiments, the apparatus above includes one or more amplifier circuits (e.g., as part of the digitizing circuit), that amplifies the sensed ECG signals to provide amplified ECG signals for digitizing. In certain embodiments, the amplifier is a circuit that provides a buffering function and has a gain of one. In other embodiments, the amplifier circuit is a filter that removes frequencies outside the bandwidth of the ECG signal.

In accordance with various example embodiments, a system computes a parameter value for a segment of a cardiac-related signal, using a computer circuit that carries out functions as follows(e.g., software-based modules). The cardiac-related signal may include, for example, one of an ECG signal, a blood pressure signal, a photoplethysmography signal, a blood oxygen saturation signal and a blood flow signal. In the context of this disclosure, a cardiac-related signal generally refers to any signal that includes an information component that is modulated by or correlates with the cardiac cycle.

The following discussion characterizes example embodiments as may be carried out with a computer circuit, such as that described above, with the understanding that various aspects may be implemented in separate, communicatively coupled computer circuits (e.g., computers communicating over a network). The example embodiments may also be implemented in connection with a computer-readable medium having instructions that, when executed by a processor (e.g., computer circuit) cause the processor to carry out the described functions. Correspondingly, the various approaches may also be implemented as part of a method in accordance with one or more example embodiments.

In a particular embodiment, a computer circuit identifies cardiac cycles within a segment of a physiologic signal, and at least one feature point within the cardiac cycles. For each of the identified feature points, the computer circuit computes a signal-to-noise ratio (SNR) representative of the ratio of signal energy to noise energy for a cardiac cycle subsegment containing the identified feature point, and determines a validity characteristic of the feature point based on the signal-to-noise ratio computed for the subsegment. In some implementations, the SNR values corresponding to multiple cardiac cycles in the cardiac-related signal are combined. The computer circuit further computes a parameter value by combining feature points contained within said segment based upon the determined validity characteristics of the feature points. This parameter value may, for example, pertain to a cardiac-related signal representative of valid feature points as corresponding to the determined validity characteristic.

The computer circuit computes the SNR representative of the ratio of signal energy to noise energy for a cardiac cycle subsegment containing the identified feature point in various manners, depending upon the implementation. In one implementation, the computer circuit computes a SNR for a cardiac cycle subsegment consisting of a point in the cardiac cycle at which the identified feature point occurs. In another implementation, the computer circuit computes a SNR for a cardiac cycle subsegment consisting of about 10% of the cardiac cycle. The computer circuit computes the SNR for a cardiac cycle subsegment consisting of a portion of the cardiac cycle excluding approximately the QRS complex, in another implementation.

In a more particular implementation, the computer circuit computes the SNR by decomposing the physiological signal from a first domain into subcomponents in a second domain. Subcomponents that are primarily associated with noise and those that are primarily associated with a desired signal are respectively identified. A ratio of energy contained in subcomponents primarily associated with the desired signal to subcomponents primarily associated with noise is computed and used to characterize the SNR.

In another more particular implementation, the cardiac-related signal is a digitized signal having a multitude of sample points, and the computer circuit computes the SNR by defining the subsegment as a subsegment of the digitized signal including at least two sample points consecutively before the identified feature point, and two sample points consecutively after the identified feature point. The SNR values for each sample point in the subsegment are combined to compute the SNR for the subsegment.

The computer circuit identifies feature points in a variety of manners. In one implementation, the computer circuit identifies feature points by decomposing the physiological signal from a first domain into subcomponents in a second domain and identifying subcomponents of the physiological signal associated with a signal wave containing a feature point. The identified subcomponents are used to construct an emphasis signal, and the emphasis signal is evaluated to identify at least one of a peak, valley, and inflection point as corresponding to a feature point. Other signal characteristics may also be used to identify feature points, as may be applicable to a particular type of signal being processed (e.g., a period of time with no change, or a range covering particular events).

In some embodiments, the computer circuit compresses the cardiac-related signal. In one implementation, the cardiac-related signal is compressed by removing noise from the signal and identifying uninterpretable segments of the signal. For example, in-band noise may be removed using at least one of adaptive filtering, linear filtering, nonlinear filtering, and multidomain filtering. Segments may be identified as uninterpretable by identifying segments exhibiting a signal to noise ratio (SNR) that is less than a predefined threshold.

A predetermined data value and cycle length is assigned to the uninterpretable segments, and a two-dimensional image of cardiac cycles sorted by the cycle length is created. The two dimensional image is then compressed (e.g., and communicated for use in evaluating a subject). In a more particular implementation, the two dimensional image is compressed by executing an encoding algorithm including an algorithm based upon one of embedded zerotree wavelet, set partitioning in hierarchical trees (SPIHT), modified SPIHT, and embedded block coding with optimal truncation encoding.

Another example embodiment is directed to a system for evaluating a physiological signal including a computer circuit configured to automatically classify segments in the physiological signal as uninterpretable, which can be used to reduce (or significantly reduce) a remaining amount of data to be evaluated. A signal to noise ratio (SNR) is calculated as the ratio of energy corresponding to an expected signal to energy corresponding to noise, for a plurality of sample points in a segment of said physiological signal. The SNR is compared to a predefined threshold (e.g., selected based upon a type of a physiological signal) below which said segment is uninterpretable, and the segment is classified as uninterpretable if the SNR is less than the threshold. A plurality of such segments can be processed, with an output generated to include those segments not determined to be uninterpretable.

In a more particular embodiment, the computer circuit computes the SNR by decomposing the physiological signal from a first domain into subcomponents in a second domain, and identifying subcomponents that are primarily associated with noise and those that are primarily associated with a desired signal. The ratio of energy contained in subcomponents primarily associated with the desired signal as relative to subcomponents primarily associated with noise is used as the SNR.

In another more particular embodiment, the computer circuit sets an alarm indicating poor signal quality, which can be used to determine an error or malfunction. In various implementations, the computer circuit sets the alarm in response to the duration of an uninterpretable segment exceeding a predetermined time period, and/or a proportion of uninterpretable segments in a physiological signal exceeding a threshold for a predetermined time period.

Another example embodiment is directed to a system for detecting a cardiac arrhythmia event spanning two or more cardiac cycles in a cardiac signal. A computer circuit identifies cardiac cycles in the signal, computes a feature signal comprised of valid R-wave feature points, and detects a cardiac event by evaluating a characteristic of said feature signal. A signal-to-noise ratio (SNR) is computed as a ratio of signal energy to noise energy for substantially the full duration of each cardiac cycle contained in said detected event. A confidence value is computed as a function of the SNR, and the detected cardiac event is classified as valid in response to said confidence signal exceeding a predetermined first threshold. Such confidence values may, for example, make up part of a confidence signal that includes one or more such values. In addition, the confidence value may be computed based upon the SNR, morphology of the signal and a pattern of feature points in the signal.

In a more particular embodiment, the computer circuit compares the confidence value to a second threshold less than the first threshold, and classifies the detected event as uncertain if the confidence value is less than the first threshold and greater than the second threshold. The detected event is further classified as invalid if the confidence value is less than the second threshold.

Another example embodiment is directed to a method for reporting arrhythmia information of a subject. The method may be carried out, for example, in a computer-based circuit (e.g., executing instructions to carry out the method), or as part of the execution of instructions on a computer-readable medium. R-wave feature points of a conditioned, digitized and denoised ECG are detected and a signal-to-noise ratio (SNR) is computed for each feature point. Valid R-wave feature points are identified based upon the signal to noise ratio. Arrhythmic events are detected by evaluating characteristics of consecutive ones of the identified valid R-wave feature points, and a confidence signal is computed for each event-based upon the computed SNR. Each event is classified as one of valid, invalid, or uncertain based upon said confidence signal. Event data indicative of valid and uncertain events is generated and output to facilitate both the review of the uncertain events for determining the presence of a valid arrhythmia event and the reporting of valid arrhythmia events.

In some implementations, the ECG is denoised by decomposing the ECG from a first domain into subcomponents in a second domain. Subcomponents associated with noise are identified based upon the spatial distribution of the subcomponents, and a denoised ECG is constructed from subcomponents that are not identified as being associated with noise.

The signal-to-noise ratio may be computed using one or more approaches as discussed herein. In one implementation, the ECG recording is decomposed from a first domain into subcomponents in a second domain, and target subcomponents associated with noise are identified based upon the spatial distribution of the subcomponents. The signal to noise ratio is computed as the ratio of energy not contained in said target subcomponents to energy contained in said target subcomponents.

The arrhythmic events may be detected in a variety of manners. In one example, an arrhythmic event is detected by identifying a pattern of feature points characteristic of an arrhythmia. An arrhythmic event may also be detected by identifying a change in ECG morphology characteristic of an arrhythmia.

The confidence signal may be computed in various manners as well. In one implementation, the morphology of the signal including the event is evaluated to determine if the morphology is consistent with the presence of an arrhythmia. The confidence signal is computed based upon the determined consistency and the computed SNR.

The event data may be output for a variety of applications and processed accordingly. In one embodiment, the event data is received at a remote monitoring facility, arrhythmia events classified as valid are automatically reported, and arrhythmia events classified as uncertain are further evaluated. For instance, the uncertain events can be reviewed to confirm or deny the presence of an arrhythmia. The events classified as uncertain for which the presence of an arrhythmia is confirmed are also reported.

Another example embodiment is directed to a system for denoising an ECG-based signal having a signal-to-noise ratio ($SNR_A$) of about 5 dB (e.g., between 3-7 dB) and that exhibits noise characteristics corresponding to (e.g., falling within a common range of) a single channel digitized noise-free human $ECG_C$ signal contaminated with additive white noise that is band-limited to between about 0.5 Hz-100 Hz. In this context, the $SNR_A$ is a signal-to-noise ratio computed using the NST procedure described in PhysioNet [17] and in ANSI/AAMI EC57:1998 standard [18]. The system includes a circuit that decomposes the ECG-based signal into subcomponents using a transform, a circuit that identifies subcomponents containing noise energy and subcomponents containing signal energy. Another circuit removes subcomponents identified as containing noise energy and reconstruct a denoised ECG signal by performing an inverse transform on the subcomponents that are not removed, the denoised ECG signal having $SNR_A$ of at least 20 dB and quality of signal reconstruction (QSR)>95% (e.g., as exemplified further below). These circuits may, for example, be a common, shared circuit or include one or more different circuits.

Another example embodiment is directed to an article of manufacture that includes a processor-readable storage medium configured with configuration data that when executed by a processor, cause the processor to perform the following steps. Cardiac cycles within a segment of a cardiac-related signal are identified, by at least one feature point within the cardiac cycles. For each of the identified feature points, a signal-to-noise ratio (SNR) representative of the ratio of signal energy to noise energy is computed for a cardiac cycle subsegment containing the identified feature point. A validity characteristic of the feature point is determined as a function of said signal-to-noise ratio. A parameter value is computed by combining feature points contained within the segment based upon the determined validity characteristics of the feature points.

According to another example embodiment, and referring to FIG. 1, physiological signals from one or more subjects are monitored using a system that includes one or more telemetric ambulatory monitoring devices (TAMD) 101 (examples shown as 101A-D), also referred to as subject devices, associated with each monitored subject and at least one data collection and review system (DCRS) 106. DCRS 106 includes at least one wireless communication module 102 (examples 102A-102B shown) that provides bidirectional communications between the TAMD 101 and a DCRS 106. The physiologic monitoring system of FIG. 1 also includes communication link 104 to pass information between DCRS 106 and remote communicator 105 and slave computing device 107. DCRS 106 includes a review function/system 103, via which trained persons can review information received from TAMD 101, and a reporting function 108 that generates reports summarizing information gathered from monitored subjects. The reports can be configured with sufficient information for use by decision makers such as physicians or researchers as an aid in making choices regarding therapies and the safety and efficacy of experimental devices and drugs.

Figure 2:
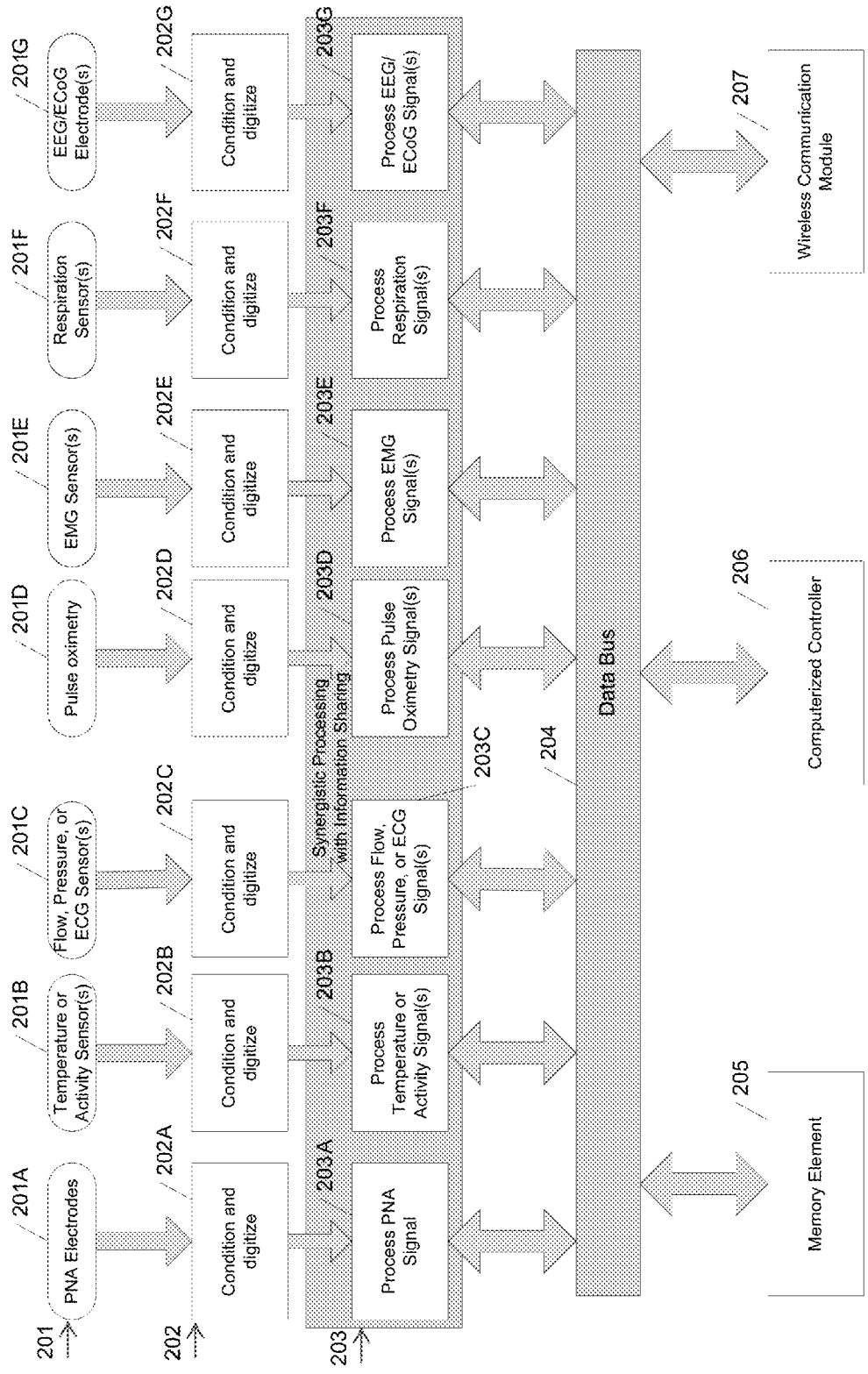
FIG. 2 shows a block diagram of a TAMD, indicating the various sensors, data flow, control, communications, signal processing, and data storage functions, consistent with another example embodiment of the present invention.

In one embodiment, referring to FIGS. 1 and 2, TAMD 101 performs: a) sensing of one or more physiological signals via sensors 201 (with examples shown as 201A-201G), b) conditioning and digitizing of the sensor output via circuits 202 (examples shown as 202A-202G), c) processing of digitized signals using computerized circuitry 203 (examples shown as 203A-203G) including a microprocessor, a state-machine, or a combination thereof to remove noise, extract information and reduce data volume for transmission, d) storing of data in a memory element 205 for later transmission to the DCRS, e) detection of alarm conditions using computerized circuitry 203, and f) communication of data and control commands to and from the TAMD via wireless communication module 207. Data bus 204 is used to communicate data and signals between various system elements of TAMD 101. Computerized controller 206 is a microprocessor, microcontroller, or state machine that provides control of data sampling, data processing, wireless communications, and other functions necessary to control operation of the TAMD. In some embodiments, the functions of computerized controller 206 and the computerized circuitry of 203 are performed by a single data processing and control element. In certain embodiments, TAMD 101 is powered by a battery and configured to be worn on the surface of the subject or implanted within the body of the subject.

Figure 3:
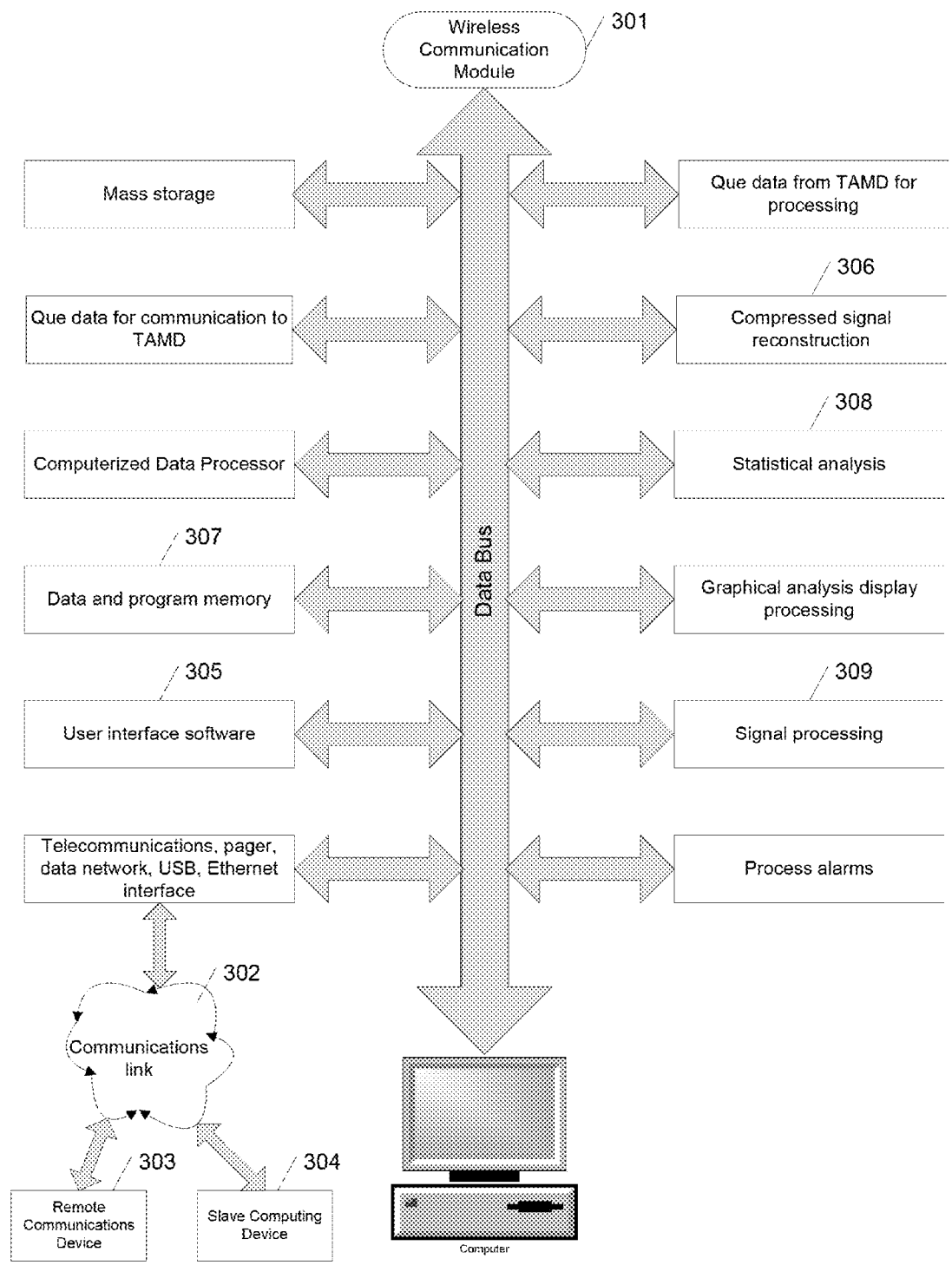
FIG. 3 shows an example block diagram of the DCRS, in connection with another example embodiment of the present invention.

In one embodiment, referring to FIG. 3, the DCRS 106 performs: a) processing, displaying, analyzing, and storing of signal waveforms, data, and alarms received from TAMDs 101, b) system control functions including providing a user interface for entry of setup and control parameters that independently define certain functions of each TAMD as well as the operating parameters of the data review system, c) provision and/or operation of a user interface to control retrieval, analysis, and review of data and signals stored on the data review system, and d) the controlling of communications to devices located remote from the data review system that may be used for receipt of notifications of important events detected by the system and for review of data, signals, analysis results, and system performance metrics. In one embodiment, DCRS 106 includes a computer-based software system such as a microprocessor-based personal computer system running the Microsoft Windows 7, XP, or Vista operating system with a computer monitor, hard disk drive, memory, keyboard, mouse, and Ethernet and USB communications capability. In one embodiment, a USB communications port is used to communicate with a wireless communication module to transmit data to and from the TAMD. In another embodiment, communications link 302 provides a way of communicating with a remote communications device 303 to notify a user located remote from DCRS 106 that an alarm condition has occurred. Communications link 302 can be a wide-area network, local area network, or a direct connection via a USB or Ethernet link. Remote communications device 303 may include one or more appliances that communicates via email (e.g., networked PC or mobile phone), a pager, automated telephone message, SMS text message, or facsimile, and that displays a received message.

Communications link 302 can also provide for communication with a slave computing device 304. In some embodiments slave computing device 304 provides a platform for implementing data processing, analysis, or control functions, and provides a way to add functionality to the system without having to modify the design of the DCRS. New system updates and functionality can be implemented while mitigating expensive and time consuming validation efforts (e.g., for customers that are using the system in an FDA GLP environment). Further, the updates may not provide value to these GLP customers. With this architecture, the DCRS can remain unchanged and added functionality that is not of interest to GLP customers can be implemented in slave computing device 304. This architecture also provides the ability for customers to add unique functionality to their system by adding it to device 304.

In another example embodiment, and referring to FIGS. 1 and 2, TAMD 101 includes sensors 201 for sensing at least one of ECG, blood pressure, EEG, EMG, blood oxygen (via pulse oximetry), blood flow, peripheral nerve activity, hemoglobin (via pulse oximetry), temperature, motor activity, and respiration (via impedance or pulse oximetry). TAMD 101 may also include other physiological signals of interest including acoustic sensors for monitoring respiration, heart sounds, and vocalization. Sensors for ECG, blood pressure, blood flow, respiration, impedance, blood oxygen, and hemoglobin are often used to assess the status of the cardiovascular and pulmonary system. Temperature and motor activity may be used to evaluate pyrogenic effects of medications or infectious agents, reproductive cycle status, as well as the general well-being of a subject. Sounds and vocalizations can be used to assess cardiac rhythm, social behavior, respiration, and heart failure decompensation status. TAMD 101 includes circuitry 202 to condition and digitize the signal provided by sensors 201, computerized signal processing circuitry 203 to process the digitized signal to remove noise, compress the signal, and extract information, a data bus 204 for communication between functional elements within the TAMD, a memory element 205 to store data, configuration information, and computing instructions. In one embodiment, the TAMD includes wireless communication module 207 that provides the capability of communicating to and from DCRS 106.

Various embodiments include a number of different types of sensors 201. The sensors for measurement of bioelectric potentials such as PNA, ECG, EEG, EMG, and ECoG, include two or more electrodes positioned at an appropriate location. Bioelectric signals are communicated from the electrodes to amplifiers in TAMD 101 via connecting wires. Amplifiers in condition and digitize circuitry 202 may have associated filtering that suppresses spectral content outside the bandwidth of the signal of interest. Such filters may incorporate both low pass and high pass filtering functions. The cutoff frequency of the low-pass filter is often chosen to preserve the signal content and to avoid aliasing.

Signal conditioning for other sensor types such as temperature, activity, pressure, respiration, and pulse oximetry may vary depending upon the implementation. In one embodiment, temperature is sensed using a thermistor and signal conditioning circuitry converts resistance changes to a voltage that can be digitized. In another embodiment, an activity sensor includes an accelerometer that produces a voltage signal when an acceleration of the subject occurs. Signal conditioning for the activity sensor includes an amplifier and integrator. In various other embodiments, one or more sensors are used as follows: pressure is sensed using a piezoresistive or capacitive sensor; respiration is sensed using a tissue impedance sensor, an acoustical sensor, resistive strain gauge, piezoelectric strain gauge, or diaphragmatic EMG sensor; flow is sensed using an ultrasonic or electromagnetic flow sensor; and pulse oximetry involves the use of multiple diodes to measure reflectance or transmission of light in tissue. A variety of signal conditioning techniques that convert the sensed signal into a voltage that can be digitized are used, depending upon the implementation. Digitization of the analog signal can be performed using various analog-to-digital converters. In some embodiments, the sampling rate is chosen to be 2.5 to 5 times the cut-off frequency of the low-pass anti-aliasing filter implemented in signal conditioning circuits 202.

Many physiological signals can be characterized as having features and parameters. A feature point is an identified point within a physiological signal. In heart related signals, such as ECG, arterial pressure, and blood flow, this is a point that is present in most cardiac cycles. Examples include the onset of the Q-wave (e.g., Q-wave onset) in an ECG or systole in an arterial blood pressure signal. Each of these feature points is described by time of occurrence and amplitude and consecutive feature points form a feature signal. In some implementations, a predetermined number of feature points or features points over a predetermined period of time are combined to compute a parameter. For example, systole feature points can be combined over a 30 second period to compute a mean systolic pressure. Computing a parameter can have the effect of reducing or eliminating short-term physiological fluctuations (e.g., changes with respiration) that are not of interest to the user.

Physiological signals may also contain events, and identifying the onset and offset of the event, or simply the fact that an event occurred, can be useful. For example, when monitoring the ECG of a subject it may be useful to know that an arrhythmic event such as ventricular tachycardia or atrial fibrillation has occurred; various embodiments are directed to detecting such events based upon a degree of validity of the signals. In additional embodiments, feature points are combined from multiple signals to compute features and parameters. For example, QA interval is often used as a surrogate for cardiac contractility, employs both a pressure and ECG signal from a subject, and is computed as the time difference between Q-wave onset and the upstroke of an arterial pressure wave. QA interval feature points are computed for a cardiac cycle, can be used to create a feature signal, and can be averaged over a predetermined period of time to create a QA parameter.

In various embodiments, the digitized signals from the sensors are processed by computerized signal processing circuitry 203 to remove noise (e.g., denoising), detect the presence of predetermined conditions and performance anomalies, reduce the volume of data through data compression, compute a dynamic signal-to-noise ratio as a metric of signal quality, extract information, detect feature points, compute parameters, detect physiological events, and determine the validity and accuracy of extracted information such as feature points and parameters, or the validity of detected physiological event. The extent of signal processing functions performed by the complete system and by each component within the system varies according to a number of factors including the nature of the signal to be processed and the intended application, features, and performance objectives of the system. In some embodiments, all signal processing functions are performed within TAMD 101. In other embodiments, a subset of these functions is performed in TAMD 101, and remaining functions are performed in DCRS 106. For example, in some embodiments denoising, identification of feature points, computation of the dynamic signal-to-noise ratio (dSNR), and determination of the validity of feature points within TAMD 101 are carried out. In these embodiments, event detection, and parameter computation are performed within DCRS 106.

As referenced above and otherwise used herein, the term dynamic signal-to-noise ratio generally refers to a signal to noise ratio of at least one point. Accordingly, such a ratio may apply to a signal to noise ratio (SNR) as discussed herein, or to the combined SNR of several points (e.g., corresponding to an ECG).

Figure 4:
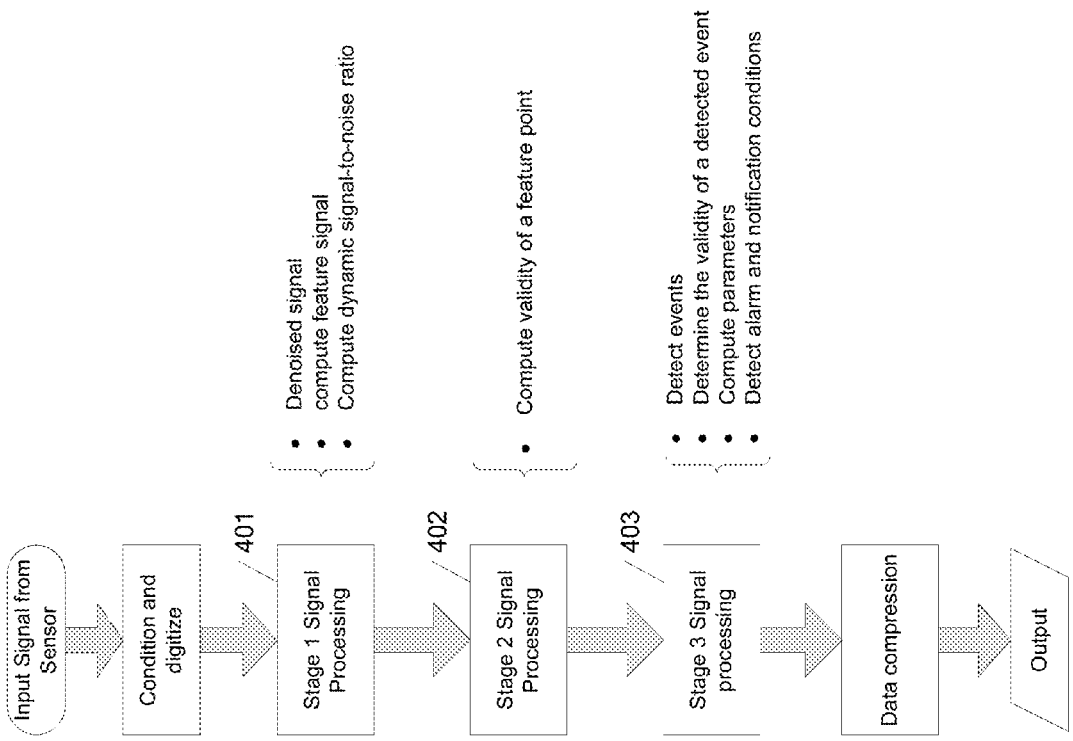
FIG. 4 shows high-level signal processing flow including stage 1, 2, and 3 signal processing partitions, according to another example embodiment of the present invention.

In various example embodiments, and referring to FIG. 4, certain signal processing functions can be partitioned into three stages; stage 1, stage 2, and stage 3. Stage 1 (process 401) includes denoising, identifying features (feature points), and computing a dynamic signal-to-noise ratio (dSNR). Stage 2 (process 402) includes determining the validity of feature points. Stage 3(process 403) includes event detection, determining the validity of a detected event, computing parameters, and detecting alarm and notification conditions. In connection with these and other embodiments as discussed herein, the various stages may be implemented with a specific circuit, such as a processor, a computer program to carry out some or all stages, or a combination of circuits, circuits and computers, or related arrangements.

In one embodiment, TAMD 101 performs stage 1, stage 2, and stage 3 functions. In connection with various example embodiments, it has been discovered that, by computing all 3 stages of signal processing within the TAMD (e.g., with SNR used to automatically determine the validity of points), a high degree of data volume reduction can be achieved and hence the power required by wireless communication module 207 is reduced. However, in some embodiments, the TAMD 101 performs less than all functions (e.g., TAMD performs stage 1 functions with DCRS 106 computing stage 2 and stage 3 functions). In some embodiments, to conserve power TAMD 101 can be configured by the user to perform only those functions required by the application, with the remaining functions being implemented in DCRS 106. The desired configuration is selected with user interface software 305 in DCRS 106 and is communicated from the DCRS to TAMD 101 via modules 102 and 207. The configuration is implemented within TAMD 101 via computerized controller 206. For example, the user may enter information as to which features to extract from a denoised signal, which type of events to capture, how often to compute parameters, or how long the interval should be for combining features to compute a parameter. Configuration information may also be used to optimize performance of the signal processing algorithms performed by computerized signal processing circuitry 203, such as the range of heart rates, species selection, or other information that is specific to a particular subject and may require a different characteristic of the algorithm to optimize performance. Communication modules 102 and 207 may also be used to communicate commands instructing TAMD 101 to transmit a real-time denoised signal, communicate device status, or communicate signals, events, parameters, features, and alarms stored in TAMD memory element 205. In certain embodiments user inputs are used to configure the partitioning of certain signal processing functions between TAMD 101 and DCRS 106, and wireless communication modules 102 and 207 are used to download embedded code into TAMD 101, which reconfigures its operating modes and capabilities based upon the code. In an alternative embodiment, the embedded code necessary to reconfigure operating modes and capabilities is stored in memory located within TAMD 101.

Although the system provides for transmission of the signal waveform, some embodiments are directed to only communicating information extracted from the signal rather than transmitting the signal waveform. This can result in a substantial reduction in power consumption within TAMD 101. Although extracting information requires power, a net reduction in power to operate TAMD 101 can be achieved using efficient signal processing algorithms that require much less power to compute parameters than is required to transmit a continuous signal waveform. These embodiments can be useful to extend battery life and reduce the size of the TAMD.

Computing a Denoised Signal

Various embodiments are directed to reducing noise in a physiologic signal and improving the signal-to-noise ratio to improving the accuracy of aspects of physiologic signal processing including feature point detection, event detection, parameter computation, and data compression. Denoising in the context of various embodiments involves removing at least some of the noise that is within the bandwidth (e.g., in-band) of the signal. However, various embodiments may be implemented in connection with denoising that involves the use of other filtering techniques that remove noise that is outside the signal bandwidth, such as band pass filtering. Various embodiments involving denoising may be applied with the specific aspects of an embodiment specific to the characteristics of a particular signal. In one embodiment, denoising of signals such as ECG, respiration, pulse oximetry, blood pressure, EEG, EMG and flow is accomplished using adaptive filtering [1], Kalman filtering [2], or wavelet thresholding [3]. In another embodiment, a signal processing approach using multiple domains is used as described in connection with one or more example embodiments in U.S. patent application Ser. No. 12/938,995, entitled "Physiological Signal Denoising," which is fully incorporated herein by reference. For example, one or more embodiments as described in the 12/938,995 application referred to as involving MultiDomain Signal Processing (MDSP) may be implemented in connection with one or more embodiments as described herein. In some embodiments of denoising of PNA signals, high pass filtering, wavelet thresholding and MDSP may be used as described in detail later in this document. Embodiments of MDSP involving denoising may also be referred to as MultiDomain Filtering (MDF) as discussed in the U.S. patent application Ser. No. 12/938,995.

In an example embodiment, a signal in a first domain is decomposed into subcomponents in a second domain of higher dimension than the first domain. The decomposition may be performed in a manner consistent with one or more example embodiments as described in U.S. patent application Ser. No. 12/938,995, referenced above. In some embodiments, decomposition is accomplished using a discrete cosine transform [4], Fourier transform [5], Gabor transform [6] or Karhunen-Loeve transform [7,8]. In another embodiment, decomposition is accomplished using a wavelet-related transform and the decomposition levels correspond to wavelet scales.

In the second domain the subcomponents associated with noise and signal are identified and separated. This is accomplished by using one or more of principal component analysis (PCA), independent component analysis (PCA), periodic component analysis ($\pi$CA) and spatially selective filtering (SSF). PCA and ICA are applicable to multi-lead signals such as ECG, while $\pi$CA and SSF can be applied to either multi-lead or single lead signals.

The PCA technique [9,10] uses subcomponent covariance information to orthogonalize subcomponents. The orthogonalized subcomponents with low signal power are often associated with noise and can be removed to achieve denoising. PCA can be used as a preliminary step prior to applying an ICA technique. The ICA technique [11] further separates signal sources as a solution of an optimization problem that maximizes independence between them. The $\pi$CA technique computes and jointly diagonalizes covariance and autocorrelation matrices of subcomponents to separate them based on their periodicity or quasi-periodicity [12, 13]. The autocorrelation matrix is calculated as an average of autocorrelation matrices computed over time lags corresponding to cardiac cycle lengths. In another embodiment a quasi-periodic signal is phase-wrapped by mapping the cardiac cycle length to a linear phase $\phi(t)$ assigned to each sample. Then the autocorrelation matrix can be calculated in the polar coordinates in which cardiac cycles are phase aligned. The $\pi$CA technique extracts most quasi-periodic subcomponents corresponding to physiologic signals and, since noise is not generally periodic, it is left behind.

SSF techniques [14, 15, 16] are used to detect signal-related features and pass them across the subcomponents while blocking features inherent to noise. The technique relies on the differences of noise and signal distributions across decomposition levels. In one embodiment, spatially selective filtering is facilitated by a decomposition whereby signal energy is concentrated in a small number of large subcomponent coefficients while noise is spread out across many decomposition levels and is represented by small coefficients. Techniques similar to wavelet thresholding can be used to remove this noise.

In another embodiment, spatially selective filtering is used to exploit the fact that most noise subcomponents are confined to decomposition levels that represent high frequencies. In this embodiment the locations of signal features are identified by examining subcomponents corresponding to lower frequency. For example, a QRS wave location can be identified as high amplitude changes in peaks and valleys that occur simultaneously across multiple decomposition levels associated with lower frequencies. The subcomponents associated with high frequency are then passed if they are around identified peaks and valleys, otherwise they are zeroed. For further information regarding these methods for denoising subcomponents and their implementation, reference may be made to U.S. patent application Ser. No. 12/938,995, referenced above.

By zeroing out the subcomponents or time segments within subcomponents associated with noise, and reconstructing the subcomponents associated with the physiological signal, the in-band noise level in the signal is substantially reduced, or "denoised," to create a denoised signal.

Denoising Approach/Performance Evaluation

To quantify performance of a physiological signal denoising technique, a Quality of Signal Reconstruction (QSR) and SNR improvement can be computed. The following characterizes an example embodiment specific to ECG, although this same technique can be applied to any signal. In this technique, quantifying SNR improvement and QSR is done under controlled conditions whereby a noise-free ECG ($ECG_{Clean}$) is purposely contaminated with band-limited (0.5 to 100 Hz) additive white noise to create a noisy input signal $ECG_{Noisy}$. The denoised version output is referred to $ECG_{Den}$ To quantify morphology preservation, QSR is computed as a point-by-point comparison of the denoised signal $ECG_{Den}$ to the original noise-free signal $ECG_{Clean}$ prior to imputing noise using the formula:

$$QSR = 100\% \left(1 - \frac{\sum_{i=1}^{N}(ECG_{clean} - ECG_{Den})^2}{\sum_{i=1}^{N}(ECG_{clean})^2}\right)$$

The SNR of input signal $ECG_{Noisy}$ and output signal $ECG_{Den}$ are each computed using the NST procedure described in PhysioNet [17] and in ANSI/AAMI EC57:1998 standard [18]. SNR computed using this ANSI/AAMI standard is referred to as $SNR_A$.

Various embodiments are directed to processing ECG or other signals exhibiting noise characteristics corresponding to (e.g., within the indicated ranges) a purposely contaminated signal as discussed above. The signals are denoised to achieve a resulting SNR and QSR as discussed above, using a clean ECG signal as a reference (e.g., with an actual denoised signal used in the above equation in place of $ECG_{Den}$).

Computing Dynamic Signal-to-Noise Ratio

Computing dSNR, the energy level of signal relative to noise, is used in various embodiments for evaluating the validity and accuracy of information derived from a signal or segment of a signal as well for determining if useful information can be extracted from a segment of a signal. In some embodiments, dSNR is used directly to assess the validity or accuracy of information derived from a physiologic signal such as feature points (e.g., systolic blood pressure, QRS peak, T-wave offset) or events (e.g., onset and offset of ventricular tachycardia) of a cardiac signal. In yet other embodiments, dSNR is computed on an ongoing basis to determine the quality of a physiological signal. If the dSNR is too low, the signal is considered uninterpretable (e.g., based upon a likelihood that no useful information can be extracted, even with review by a trained person). In other embodiments, if dSNR remains very low for more than a predetermined period of time, an alarm is activated indicating that a malfunction such as a sensor failure or sensor lead disconnect may have occurred.

In one embodiment, dSNR is computed as the ratio of the energies in signal and noise subcomponents computed as a byproduct of an MDSP-type denoising process as described in U.S. patent application Ser. No. 12/938,995. The MDSP approach is used to identify subcomponents as either noise related or signal related. The power contained in noise related subcomponents is computed independent of the power in signal-related subcomponents. The relative power of the noise and signal components is computed to estimate dynamic signal-to-noise ratio (dSNR). This technique allows dSNR to be updated on a sample-by-sample basis. In one embodiment, dSNR is updated for each cardiac cycle. Alternative implementations may update dSNR more or less often. In one implementation, a value of dSNR is computed for a window of two to ten cardiac cycles and this value is used in calculating a validity metric for all cardiac cycles within the window. In other implementations, dSNR is computed for a portion or segment of a cardiac cycle containing a feature point and is used to determine the validity of the feature point contained within the segment.

In other embodiments, dSNR is evaluated by computing a spectral distribution of the denoised signal. For example, in an ECG signal, amplitude of spectral distribution is evaluated to determine the relative power in the spectrum that occurs within and outside of the normal range of the QRS complex, T-wave, and P-wave. In other embodiments, the signal energy relative to noise energy is determined by computing the density of zero crossings using multiple adaptive thresholds, adaptive thresholds varying as a function of the peak signal measured. In some embodiments, this approach is applied to a region within a cardiac cycle of an ECG, such as between T-wave offset and P-wave onset.

Computing a Confidence Signal.

In some embodiments, a confidence signal is computed as an indicator of the accuracy or validity of derived information such as features and events. The confidence signal is dynamic and in some embodiments (e.g., for cardiac signals), it is updated for each cardiac cycle or it may be computed for a portion or segment of a cardiac cycle and used to evaluate the accuracy or validity of a feature point contained within the segment. In other embodiments, the dynamic confidence signal (dCS) is computed specifically for a detected event to determine if it is valid. In one example embodiment, a confidence signal is used in determining whether a detected event is ventricular tachycardia or high amplitude periodic noise. In yet other embodiments, the dCS is computed on an ongoing basis to determine the quality of a physiological signal captured by a TAMD. If the signal is found to be of such poor quality then no useful clinical information could be obtained, even with review by a trained person, the signal is classified as uninterpretable. If dCS remains uninterpretable for more than a prespecified period of time, an alarm may be triggered indicating that there is a potential malfunction such as a loose or failing sensor. In some embodiments, if the confidence signal indicates that the captured signal is classified as uninterpretable, the signal is discarded and is not wirelessly communicated by the TAMD. This effectively enhances battery life by avoiding transmission.

In some embodiments, the factors considered and the methods used for computing dCS vary with the application. For example, when dCS is used to evaluate the accuracy and validity of a feature point, dSNR and the result of a signal morphology evaluation can be used to compute a dynamic confidence signal for a feature point ($dCS_{fp}$). For example, detection of T-wave offset may be meaningless during ventricular tachycardia (VT) and ventricular fibrillation (VF). If VT is detected, the value of $dCS_{fp}$ relating to the T-wave offset feature point is driven to a very low value indicating that it is invalid. The acceptable level of dSNR to achieve a given $dCS_{fp}$ value depends upon type of signal, feature, or event as well as the criticality and implications of making an error in the specific application. Some types of feature points require a higher dSNR than others in order to achieve a given level of confidence in the accuracy of the derived information. For example, the level of allowable dSNR to achieve a high confidence that an R-wave feature point is valid is less than the level of dSNR required to achieve a high confidence that a T-wave offset feature point is valid. Due to the flat nature of the signal in the vicinity of T-wave offset and the low amplitude of T-wave offset, detection accuracy is much more sensitive to noise than it is when identifying the peak of the R-wave. In another embodiment, computing dCS to assess the validity of an arrhythmic event involves the use of dSNR as well as evaluating signal morphology and feature signal characteristics.

Figure 5:
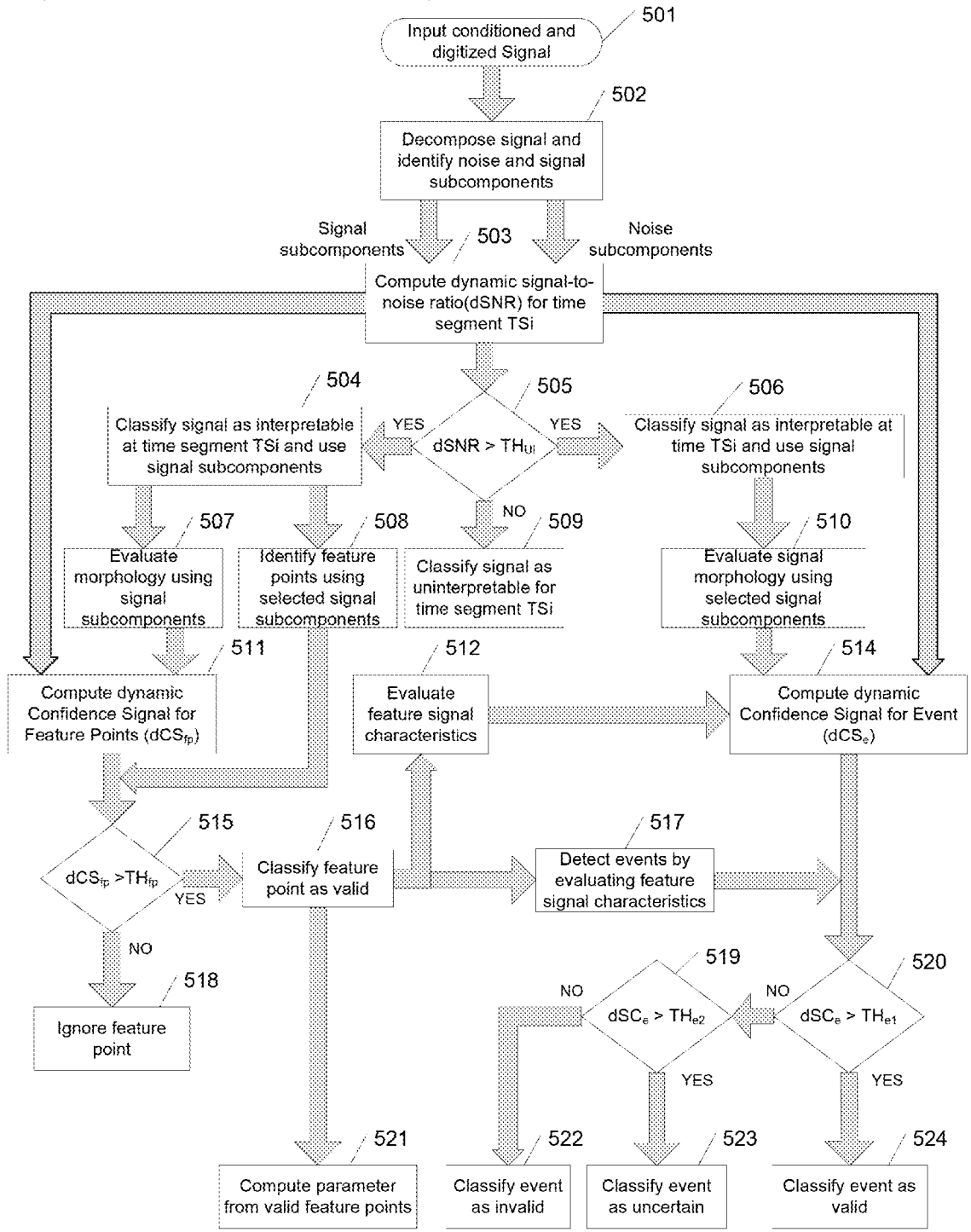
FIG. 5 shows a process for identification and validity evaluation of feature points and events, according to another example embodiment of the present invention.

FIG. 5 shows signal processing stages 1, 2, and 3 performed within TAMD 101, in accordance with various example embodiments. Feature points and events are detected and a confidence signal is computed to assess their validity. For additional detail related to identifying feature points and events in accordance with one or more embodiments, reference may be made to U.S. patent application Ser. No. 12/938,995, referenced above. Conditioned and digitized signal input in process 501 is decomposed into subcomponents and signal and noise subcomponents are identified in process 502. In process 503, the ratio of energy in signal and noise subcomponents is computed as a dynamic signal-to-noise ratio (dSNR). dSNR in process 503 can be computed on a point-by-point basis, and in some embodiments is computed for a cardiac cycle, for a short (e.g., 50 msec) segment containing a feature point (e.g., T-wave offset), or it may be computed for multiple cardiac cycles. In decision process 505, dSNR for a time segment TS is compared to a threshold $TH_{UI}$. If dSNR exceeds the threshold, the signal is classified as interpretable and the signal-related subcomponents are passed on for further evaluation and processing per processes 504 and 506. If dSNR is less than $TH_{UI}$, then the signal is classified as uninterpretable (process 509), meaning that virtually no useful information can be extracted from the signal, even if the signal is reviewed by a trained person. In alternate embodiments, decision process 505 is performed following (rather than before) detection of events and feature points. If dSNR was less than the required threshold value, feature points and events detected would be classified as invalid.

Using a Confidence Signal to Identify Valid Feature Points

In process 508, feature points are identified such as by combining relevant signal subcomponents to create a feature signal. Peaks or valleys of the feature signal are evaluated, as appropriate to identify the feature point of interest. In process 507, morphology is evaluated. In one embodiment, this is accomplished by combining appropriate subcomponents to form an emphasis signal. The emphasis signal is then evaluated for peaks and valleys to test for the presence of relevant morphologies (e.g., those of expected signal characteristics, or characteristics of a particular physiological event). The specific type of morphology of interest depends upon the type of feature detected for which validity is being assessed.

In connection with various example embodiments, techniques used for morphology evaluation are implemented in connection with one or more approaches as described in detail in references 20 and 21 (cited below), which are included herein by reference. In some embodiments involving the evaluation of signal morphology, a physiologic signal or its emphasis signal is evaluated to determine location of peak amplitudes, zero-crossings, signal widths, and signal slopes. In some embodiments, the techniques involve various waveform analysis methods such as template cross-correlation, minimum area difference [19] and Correlation Waveform Analysis [20].

In process 511, a dynamic Confidence Signal for feature points is computed ($dCS_{fp}$). In one embodiment, $dCS_{fp}$ is computed as a function of dSNR and morphology. Morphology is evaluated to determine whether a feature point should exist based upon the characteristic of the signal. For example, for an ECG and T-wave offset feature point, if evaluation of the morphology shows that ventricular tachycardia is present, a T-wave offset may not exist. The output of the morphology evaluation process 507 then functions as a multiplier, $M_i$, equal to 1 if morphology indicates a feature point should exist and 0 if not. Accordingly, $dSC_{fp} \approx M_i * k * dSNR$ where Mi is 1 or 0, dSNR is the dynamic signal to noise ratio, and k is a constant that depends on the type of feature point for which $dSC_{fp}$ is being evaluated.

In decision process 515, $dSC_{fp}$ is compared to a threshold $TH_{fp}$. If the threshold is exceeded, the feature is classified as valid in process 516 and, in some embodiments, valid features (e.g., R-R interval) are combined to compute a parameter (e.g., heart rate) in process 521. If the threshold is not exceeded, the feature point is classified as invalid and ignored for the purpose of computing a parameter, as in process 518.

Using a Confidence Signal to Classify the Validity of Events

In process 510, the morphology of the signal is evaluated. In one embodiment, this is accomplished by combining appropriate subcomponents to form an emphasis signal. The emphasis signal is then evaluated for peaks and valleys to test for the presence of relevant morphologies. The specific type of morphology of interest depends upon the type of signal and the type of event detected for which validity is being assessed.

In process 514, a dynamic Confidence Signal for an event ($dCS_e$) is computed. In one embodiment, $dCS_e$ is a function of the dSNR computed in process 503, the morphology evaluation in process 510, and the feature signal characteristics evaluation in process 512. For example, when detecting ventricular tachycardia (VT) from an ECG signal feature signal characteristics are evaluated in 512 to assess the heart rate. If the heart rate exceeds the threshold established for detection of VT, then the QRS complex is evaluated in process 510 to confirm that signal morphology is consistent with VT.

Feature point characteristics evaluated in process 512 include rate and regularity. For example, if the heart rate computed from an ECG exceeds a threshold, it may be indicative of high levels of EMG noise. In this case, process 512 would trigger process 514 to consider the morphology of the ECG signal. If morphology evaluation computed in 510 indicates the presence of a high-amplitude EMG signal, the value of dCS is driven to a low value and the event is deemed invalid. The output of the morphology evaluation process 510 thus functions as a multiplier equal to 1 if morphology indicates an event may exist and 0 if not. $dSC_{fp} \approx M_i * k * dSNR$ where Mi is 1 or 0, dSNR is the dynamic signal-to-noise ratio, and k is a constant that depends on the type of feature point for which $dSC_e$ is being evaluated. Events are detected in process 517 by evaluating characteristics of the feature signal. For example, a highly irregular heart rate could be indicative of atrial fibrillation.

In decision process 520, $dSC_e$ is compared to a threshold $TH_{e1}$ to determine if the event detected in process 517 is valid. If threshold $Th_{e1}$ is exceeded, the event is classified as valid. If threshold $TH_{e1}$ is not exceeded, then $dSC_e$ is compared to a second threshold $TH_{e2}$, where $TH_{e2} < TH_{e1}$. If $TH_{e2}$ is exceeded, then the detected event is classified as uncertain, meaning that an event might be present. If $dSC_e < TH_{e2}$ then the detected event is classified invalid. In some embodiments, threshold $TH_{e1}$ is chosen such that if $dSC_e > TH_{e1}$ the likelihood that the event is valid is so high that it isn't justifiable to have a trained person review the event before forwarding it to a decision maker, such as a physician that will use the information to diagnose and direct therapy. Various embodiments are thus directed to setting and/or using such threshold values to suit particular applications, or particular patients. Likewise, $TH_{e2}$ may be chosen such that if $dSC_e$ is $<TH_{e2}$ then the event is invalid with a very high likelihood, review by a trained person may not be justified, and the event detected in process 517 can be ignored for purposes of decision making. In some embodiments, the system is configured to recommend that only events classified as uncertain be reviewed by a trained person to assess validity.

In one embodiment, the system is configured to accept user inputs to specify, through a user interface in the DCRS and communicated to the TAMD via a wireless link, desired confidence levels relating to thresholds $TH_{e1}$ and $TH_{e2}$. For instance, a user may be willing to tolerate a 0.5% error in assigning an event as valid and a 0.5% error in assigning an event as invalid. Tolerating a higher error rate will reduce the number of events classified as uncertain Likewise, in other embodiments, the user may want to reduce errors in assigning events as valid or invalid and are willing to tolerate a higher rate of uncertain events.

In alternate embodiments, one or more portions of the signal processing can be performed outside TAMD 101. For example, TAMD 101 could compute a denoised signal, feature signals, and confidence signals and detect events while parameters as well as validity and classification of event types and alarms are computed in the data review system. In some embodiments the confidence signal can be used to trigger capture of a waveform signal. As an example, the TAMD may be configured to trigger capture of the related waveform signal prior to and after the point at which the confidence signal fell below a threshold for a specified period of time. This provides the ability to examine the circumstances under which the computation of information from the waveform signal was of suspect accuracy and also provide information that may assist in troubleshooting the reason for poor signal quality.

In some embodiments the confidence signal is used to detect a possible sensor failure (e.g., failure of a sensor, such as a pressure sensor, an electrode coming loose, or another issue that may result in a substantial decline in SNR). This may be implemented by evaluating the confidence signal for a predetermined period of time. If the confidence signal remains below a specified threshold for the specified time interval, a sensor failure alarm is activated.

In another embodiment, the dCS signal can be computed based on information shared between multiple signals to improve the reliability of the feature and event detection, and computation of the confidence signal. For example, in one embodiment, information is shared between blood pressure and ECG signals to improve the accuracy of $dCS_{fp}$ in assessing the validity of a feature point. If the detected cardiac cycles do not correspond between the two signals, there may be an error in identifying the cardiac cycle in one or both of the signals and the value of $dCS_{fp}$ will be reduced in value as a result. In another embodiment, information is shared between blood pressure and ECG to determine the validity of an arrhythmic event. If a ventricular fibrillation event is detected in the ECG but evaluation of blood pressure morphology and values indicate that hemodynamics are stable, for example, $dCS_e$ would be set to zero as stable hemodynamics are inconsistent with a ventricular fibrillation event.

Computing Parameter Values.

Parameter values are computed for a variety of different types of signals, to suit various embodiments, implementations thereof and as relevant to particular applications. In one embodiment, and referring to FIG. 6, parameter values are computed by combining valid feature points of a feature signal over a specified period of time or number of cycles of a pseudoperiodic physiologic signal. In some embodiments, each feature point is characterized by a time of occurrence and value. A feature signal is comprised of a sequence of feature points. For example, a feature signal comprised of systole feature points for cardiac cycles occurring over a period of 30 seconds can be combined to form a representative value of systolic pressure and heart rate over the 30 second interval. The time span over which features are combined to compute a parameter can be user-selectable via a user interface in DCRS 106. Time spans ranging from 10 seconds to 5 minutes for cardiovascular and respiratory related signals can be used to smooth out local fluctuations. For signals such as PNA, EMG, and EEG it may be useful to combine features over a time span of 0.5 to 5 seconds.

Figure 6:
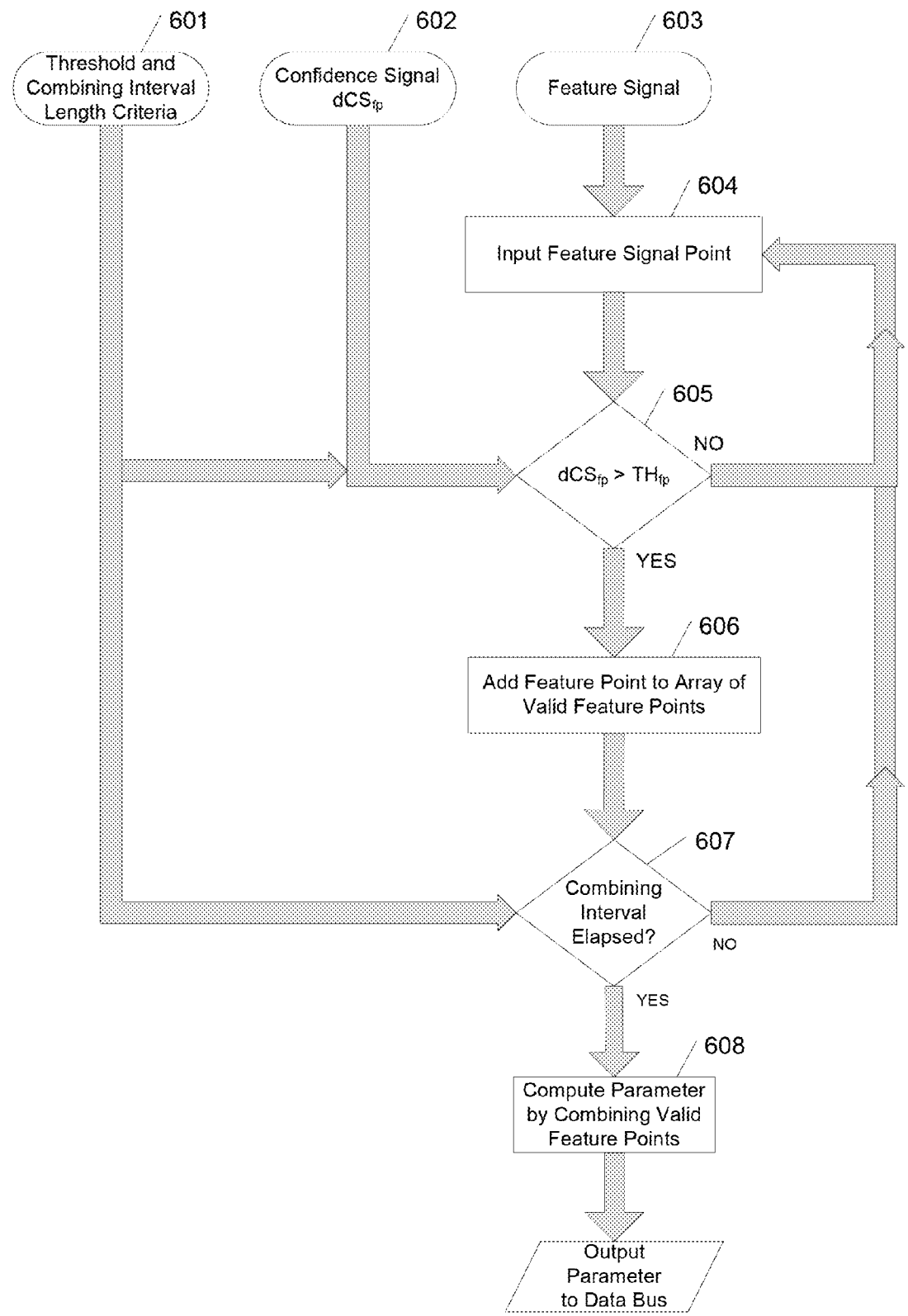
FIG. 6 shows an example data flow block diagram for computing parameters from feature points, according to another example embodiment of the present invention.

In one embodiment, and referring to FIG. 6, a parameter is computed as the arithmetic mean of valid feature points. The validity of a feature point in the feature signal is evaluated by comparing the dynamic Confidence Signal for a feature point ($dCS_{fp}$) for the corresponding cardiac cycle to a threshold $TH_{fp}$ in decision process 605. $dCS_{fp}$ is computed as in process 511 in FIG. 5.

Examples of parameters that may be derived from ECG include heart rate, QT interval, heart rate variability, heart rate turbulence, and QRS duration. Examples of parameters that may be derived from arterial pressure include heart rate, arterial pressure, diastolic pressure, and systolic pressure. Examples of parameters that may be derived from arterial blood flow include stroke volume, mean velocity, and volume flow.

In some embodiments, multiple feature signals are used to compute a parameter. As an example, a computed QA interval can be used as a measure of cardiac contractility. Computation of QA interval involves identifying the occurrence of the Q-wave in the denoised ECG and the A-point, marking initiation of the upstroke in the denoised arterial pressure signal and then measuring and recording the time difference between these two points [21].

In another embodiment, multiple feature signals can be used to improve the accuracy of parameter values. As an example, accurate R-wave detection in an ECG is essential to nearly every parameter derived from ECG, whether it is QRS duration, heart rate, or heart rate variability. However, accurate R-wave detection can be compromised if the noise level in the ECG is so high that the denoising is unable to remove enough noise to achieve accurate detection, as indicated by the dSNR or dCS being below the desired threshold. If such a situation is to arise, and both ECG and arterial pressure are available, a diastole or systole feature signal of arterial pressure is used to confirm or deny the R-wave detection in the ECG.

In another embodiment, detected locations of systole are used to identify a time window where a QRS complex would be expected. This windowing facilitates denoising using spatially selective filtering where subcomponents in the QRS window are preserved and subcomponents corresponding to high frequencies that are outside the QRS window are removed. In other embodiments, a photoplethysmography signal is used to facilitate identification of the QRS complex location for purposes of applying a window for spatially selective filtering.

In some embodiments, a parameter is computed directly from the denoised signal. For example, when processing EEG, it may be desirable to compute the power in frequency bands of an EEG signal for consecutive time periods. The power in a band would then be the computed parameter. In some embodiments, a parameter is computed from a derived signal. For example, the level of neural activity can be computed from the envelope of denoised PNA. This signal is then averaged in a specified time window (e.g., 0.5 to 5 sec) to compute a parameter of average neural activity.

In another embodiment, statistical outliers of measured intervals (such as QT or RR interval) are detected for the purpose of identifying invalid or inaccurate feature detection. In another embodiment measured intervals outside of physiologic range are evaluated. If an interval is identified as a statistical outlier or being outside of physiologic range, the value of the confidence signal will decline for the flagged cardiac cycles.

Processing Flow, Pressure, or ECG Signals

Figure 7:
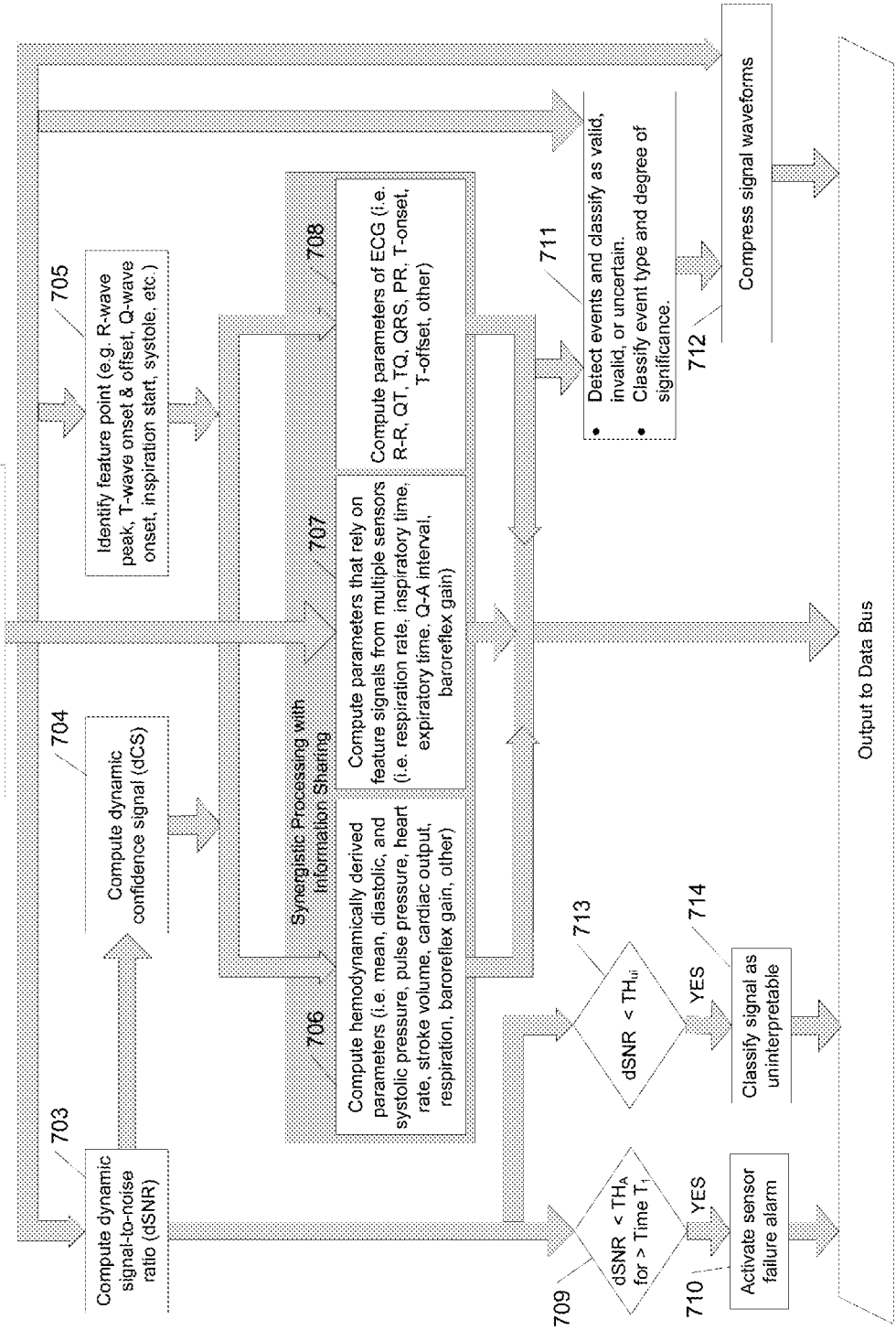
FIG. 7 shows an example data flow block diagram for processing of ECG, blood flow, and blood pressure signals, in connection with another example embodiment of the present invention.

In accordance with various example embodiments, and referring to FIG. 7, blood flow, blood pressure, and ECG are processed to remove noise, identify features and events, compute parameters, and detect alarm conditions. In some embodiments, signal waveforms are compressed in order to conserve power if the waveforms are communicated wirelessly.

Process 701 provides conditioned and digitized input signals. In this embodiment, signals include one or more cardiac signals such as flow, pressure, and ECG. In process 702, signals are denoised (e.g., in-band noise is removed using one or more of several techniques such as adaptive filtering [1], Kalman filtering [2], wavelet thresholding [3], band-pass filtering, signal averaging, and a multi-domain filtering process such as the denoising approaches as described in U.S. patent application Ser. No. 12/938,995, all of which are fully incorporated herein by reference.

In some embodiments, a dynamic signal-to-noise ratio (dSNR) is computed in process 703 to assess the whether a signal is interpretable, by comparing to a threshold as in process 713. In some embodiments, a dynamic confidence signal (dCS) is computed in process 704 based upon dSNR, feature signal characteristics, and signal morphology as described earlier in FIG. 5. The specific approach used to compute dCS may vary according to the signal type (e.g., blood pressure, flow, or ECG) and the parameter or event type for which dCS is computed. The dCSis used to assess the accuracy and validity of feature points and detected events. In embodiments where multiple signals are processed, information from one signal may be used to improve the accuracy of dCS as it applies to another signal. In one example, the detection of a systolic pressure feature point of an arterial blood pressure signal is used to verify that a QRS feature point detected in a noisy ECG is valid. To assess validity of feature points identified in process 705 and events detected in process 711, dCS is passed through from process 704.

In some embodiments, feature points are identified in process 705 from the denoised signal as described earlier in FIG.

5. The validity of the identified feature points is assessed in processes 706, 707, and 708 using the dCS computed in process 704. Those feature points that are determined to be valid are used to construct a feature signal including a two-dimensional sequence of values representing the time and amplitude of the occurrence of features of interest within the denoised signal. Examples of feature signals of possible interest that are derived (in various embodiments) from an ECG include the R-wave, Q-wave, P-wave, S-wave offset, the onset, offset and peak of the T-wave, and respiration cycles. Examples of feature signals of interest in an arterial pressure signal include systole, diastole, mean pressure over a cardiac cycle, respiration, and the point of maximum dP/dt. Examples of features of interest in a flow signal include peak flow, and mean flow over a cardiac cycle. In some embodiments, the feature signal is compressed prior to communicating to the data review system in order to reduce the volume of data to be transmitted. In the data review system the feature signal and the denoised signal are used in combination to present a graphic of feature point locations marked in the denoised signal. This may be used to visually confirm the accuracy of features and parameters computed within the TAMD, as may be required by FDA GLP regulations or by other regulatory bodies or by a user that is concerned about the accuracy of derived information.

Feature signals are computed using one or more of a number of approaches, and in some embodiments, feature signals for flow, pressure, or ECG are computed by combining certain signal subcomponents to create an emphasis signal that exaggerates a particular aspect of the signal. Computations for this approach may be effected in a manner that is consistent with that shown in and described in connection with FIG. 5 and U.S. patent application Ser. No. 12/938,995, referenced above. For example, computing the R-wave feature signal involves emphasizing the R-wave so it stands out with a higher amplitude and prominence relative to other features of the ECG such as the T-wave and P-wave. Once the R-wave is emphasized, the peak is clearly and accurately identified.

In one embodiment, the R-wave is emphasized by applying a differentiator filter to the denoised signal and squaring the resulting signal to emphasize the slope of QRS complex. In another embodiment, MDSP subcomponents that correspond to the energy of the feature of interest (e.g., R-wave) are used to compute an emphasis signal. In some embodiments, a combination of subcomponents is employed to create the emphasis signal. Depending upon feature morphology different logic is used for detecting feature points by evaluating the emphasis signal including detecting peaks, valleys, and zero crossings in subcomponents or their combinations. In another embodiment an adaptive threshold is used to detect features in the emphasis signal.

In another embodiment, a respiration rate is determined by evaluating ECG and pressure. Detection of respiratory rate from ECG and arterial pressure is accomplished by low pass filtering the R-wave feature signal, R-R interval signal, R-wave peak amplitude and baseline feature signal or the raw ECG signal as well as the systolic and mean blood pressure feature signals. The low-pass filtered signal is further processed to detect inspiration and expiration phase and measure respiration rate. By evaluating both ECG and pressure the accuracy of respiration rate measurement can be improved relative to evaluation of only one of the signals.

In some embodiments, a dSNR approach such as described herein is used to detect sensor failure such as a loose ECG skin electrode or pressure sensor failure. In process 709, dSNR is compared to a threshold $TH_A$. If dSNR remains below threshold $TH_A$ for more than a predetermined time, an alarm is activated in process 710. Activation of an alarm can cause an audible or visible form of communication to the subject that a sensor failure has occurred. In some embodiments, activation of an alarm can cause TAMD 101 to communicate a message to DCRS 106 indicating a sensor failure has occurred. A person at the DCRS can then contact the subject and take corrective action.

In process 711, events such as ventricular tachycardia, atrial fibrillation, QT prolongation, and ST segment elevation are detected and classified. In one embodiment, events are classified as valid, invalid, or uncertain as described in FIG. 5. In some embodiments, events that are detected as valid or uncertain are further classified in process 711 as to their degree of significance. In some embodiments, if an event is found to be highly significant, TAMD 101 is configured to promptly communicate a notification that such as event occurred to DCRS 106. Such an event could be one that requires prompt attention from a health care provider, or it could be an event that occurred in a research study, such as expiration of an experimental animal, that requires prompt attention. In some embodiments, the communication of events that are classified as having lower level significance is delayed to reduce cost of transmission (e.g., if cost of transmission is dependent upon time of day) or to facilitate efficiencies in a data review center where the DCRS is located.

Figure 14:
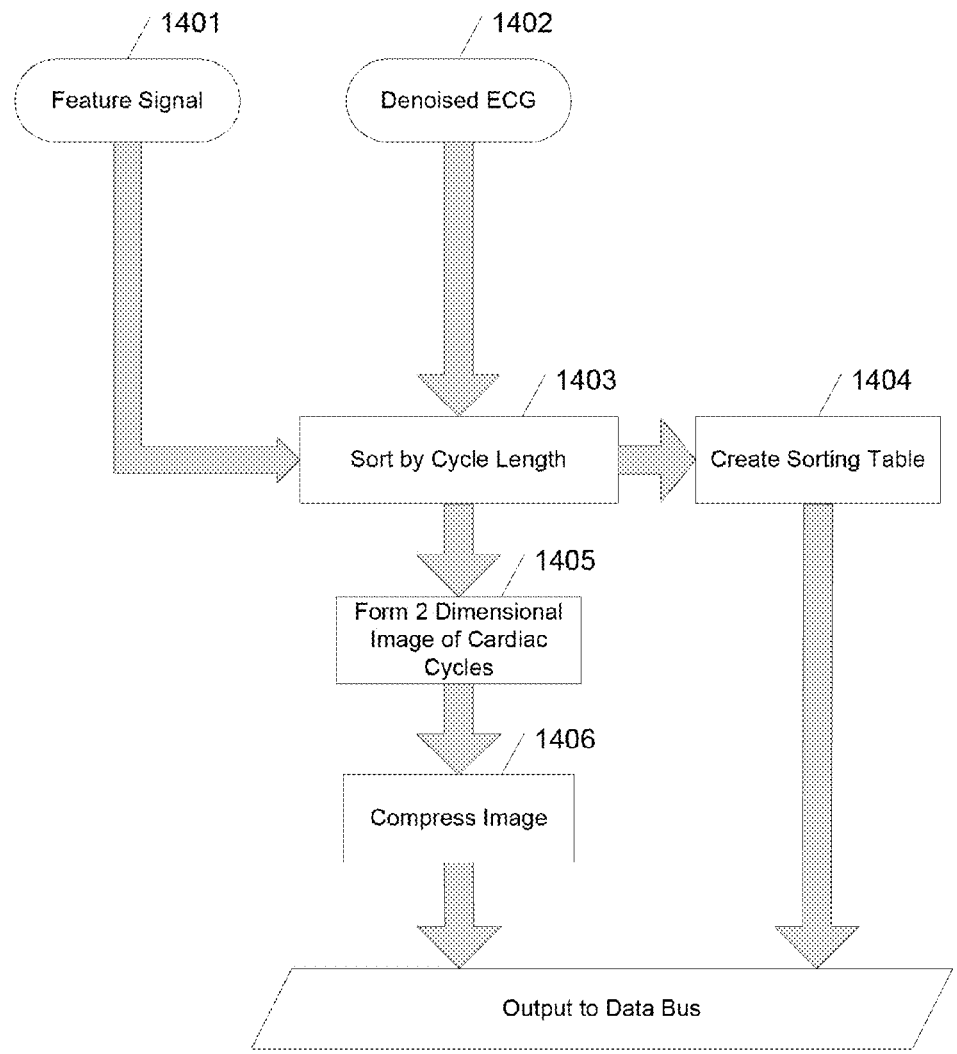
FIG. 14 shows an example data flow block diagram for compressing pseudoperiodic physiological signals according to another example embodiment of the present invention.

In some embodiments, signal waveforms are compressed in process 712 to reduce the volume of data to conserve power and extend battery life. Compression is accomplished as described in FIG. 14.

Detecting and Classifying Physiologic Events

Figure 8:
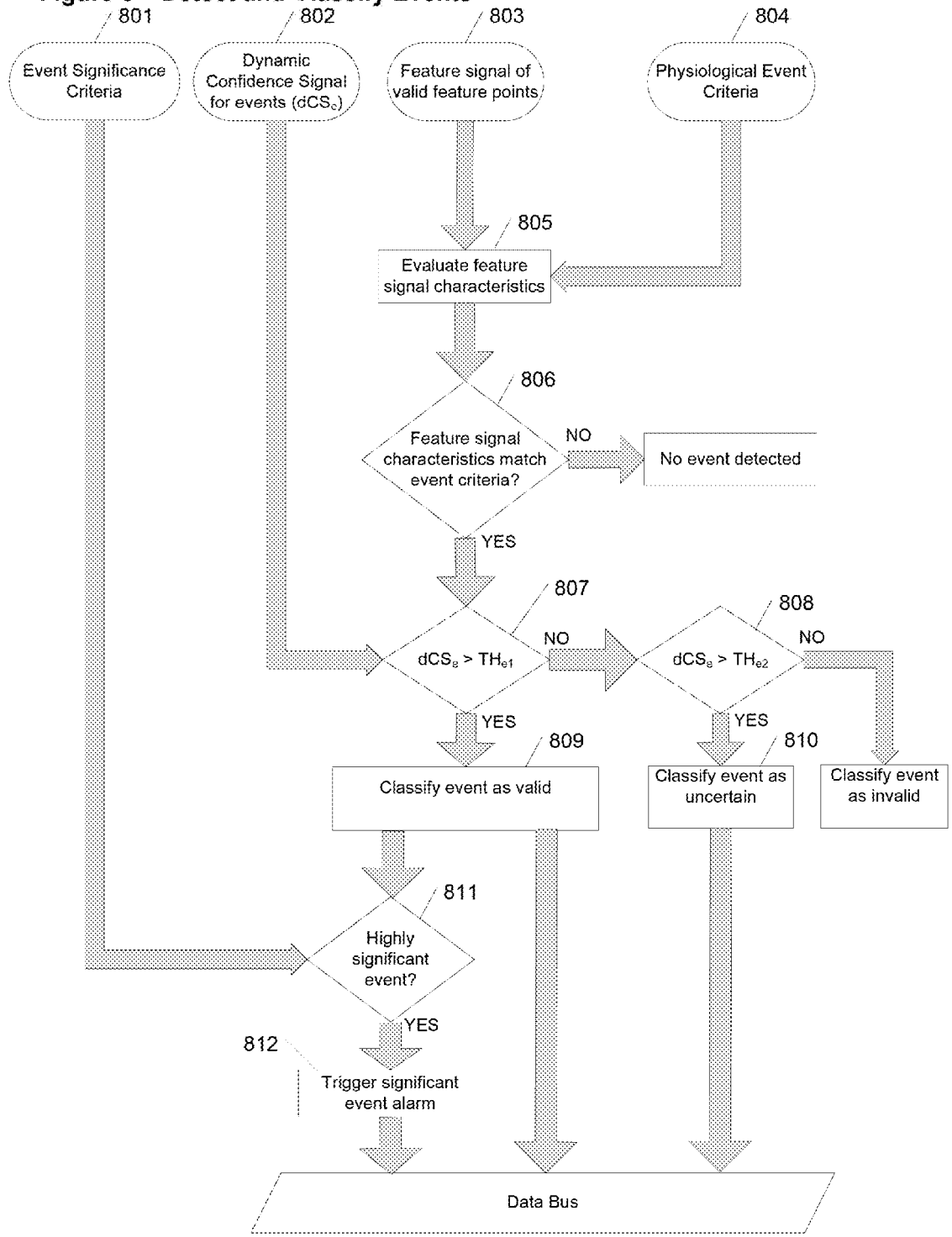
FIG. 8 shows an example process flow diagram for detection and classification of events, according to another example embodiment of the present invention.

In some embodiments, referring to FIG. 8, various cardiac arrhythmia and hemodynamic events are detected, as may be present in flow, ECG, photoplethysmography (PPG), and pressure signals. Many of the principles outlined in this section also apply, but are not limited to, detection of event in signals such as EEG, temperature, activity, and respiration. Examples of cardiac arrhythmia events of interest include bradycardia, tachycardia, Torsades de Pointes, atrial fibrillation, atrial flutter, asystole, and ventricular fibrillation. Examples of hemodynamic events that are detected include hypotension, hypertension, and unstable hemodynamics such as those that can occur during arrhythmias. In some embodiments, the accuracy of event detection can be improved by evaluating multiple signals. For example, if a tachyarrhythmic event is detected based upon evaluation of an ECG signal, the system can discriminate between sinus tachyarrhythmia and ventricular tachyarrhythmia by examining arterial pressure and determining if the characteristics of the arterial pressure signal are consistent with the occurrence of a life-threatening ventricular tachyarrhythmic event. In some embodiments, detection of cardiac cycles in ECG and arterial pressure signals are matched to verify consistency of cardiac cycle detection.

In some embodiments, user interface software 305 provides for the configuration of settings in DCRS 106 that are communicated to TAMD 101 that will cause a denoised signal containing a detected event to be captured. The denoised signal can be saved just prior to, during, and for a period of time just following occurrence of the event and will be communicated to the DCRS. This will allow a researcher or clinician to view the transition into and out of the event as well as observe the characteristics of the event itself. The captured signal can be saved in the memory of TAMD 101 for later communication to DCRS 106. An example of this is a tachycardia whereby the ECG is captured for 15 second prior to the onset of the tachyarrhythmia through a time 15 seconds post termination.

In one embodiment, detection of an event is performed by evaluating feature signal characteristics in process 805. Criteria for feature signal characteristics provided by input 804 are compared to the result of the evaluation of process 805. If a match of feature signal characteristics and physiologic criteria exists, as determined by decision process 806, then a possible event may have been identified. The $dCS_e$, provided by input 802, is compared to threshold $TH_{e1}$ in decision process 807. If $dCS_e$ exceeds $TH_{e1}$, then the event is classified as valid. In process 807 if $dCS_e$ is $<TH_{e1}$, then process 808 evaluates $dCS_e$ vs. threshold $TH_{e2}$. If the threshold is exceeded, the event is classified as uncertain. If the threshold is not exceeded, the event is classified as invalid and is given no further consideration.

In some embodiments, valid events are tested in decision process 811 to determine if they are considered to be highly significant. To determine if an event is highly significant, characteristics of the event such as morphology and rate, are compared to the event significance criteria from input 801. For example, if the detected and validated event was ventricular tachycardia (VT) with a rate >220 and this rate exceeded the threshold for VT established by input 801, this event would be deemed highly significant and the alarm would be triggered. If an event is found to be highly significant, a significant event alarm is triggered in process 812 and notification that such as event occurred would be promptly communicated from TAMD 101 to DCRS 106.

In a more particular example embodiment, arrhythmic events are detected in an ECG signal as follows. After computation of an R-wave feature signal as an input in process 803, consecutive R-R intervals are evaluated to determine whether the heart rate falls above or below the thresholds specified in input 804 for tachycardia or bradycardia detection. In one implementation, process 805 evaluates the heart rate of 14 consecutive valid feature points. If at least 10 of the feature points exceed the rate threshold, then a process 806 would indicate that a tachycardia has been detected. Decision process 807 then evaluates dCSe during the event. If dCSe exceeds threshold THe1, then the tachycardia event is classified as valid. In one embodiment, event criteria is set by a user via user interface software 305 of DCRS 106. For example, the criteria for detection of a tachyarrhythmia may specify the heart rate threshold that must be exceeded for a predetermined proportion of the cardiac cycles in a sequence of cardiac cycles. In another embodiment, event criteria input in process 804 include morphology criteria, such as QRS width and amplitude, to allow process 805 to discriminate between supra-ventricular tachycardia and life-threatening ventricular tachycardia.

Respiration Signals.

In accordance with various example embodiments respiration information is extracted from sensors and signals of various types. In one embodiment, respiratory rate is extracted from blood pressure, flow, photoplethysmography, and ECG signal using MDSP. In another embodiment, the signals indicating respiratory function include thoracic impedance and diaphragmatic EMG. Impedance sensors measure changes in impedance of the chest during respiration and rely on modulation of the impedance signal by the volume of air located in the lungs. Diaphragmatic EMG sensors measure electrical activity of the diaphragm during respiration and indicate when the muscles of the diaphragm contract, providing a diaphragmatic contraction signal. In some embodiments, intrapleural pressure is measured, which can be used in combination with indicators of inspiration and expiration, as may be derived from diaphragmatic EMG or impedance, to obtain a measure of airway resistance.

Figure 9:
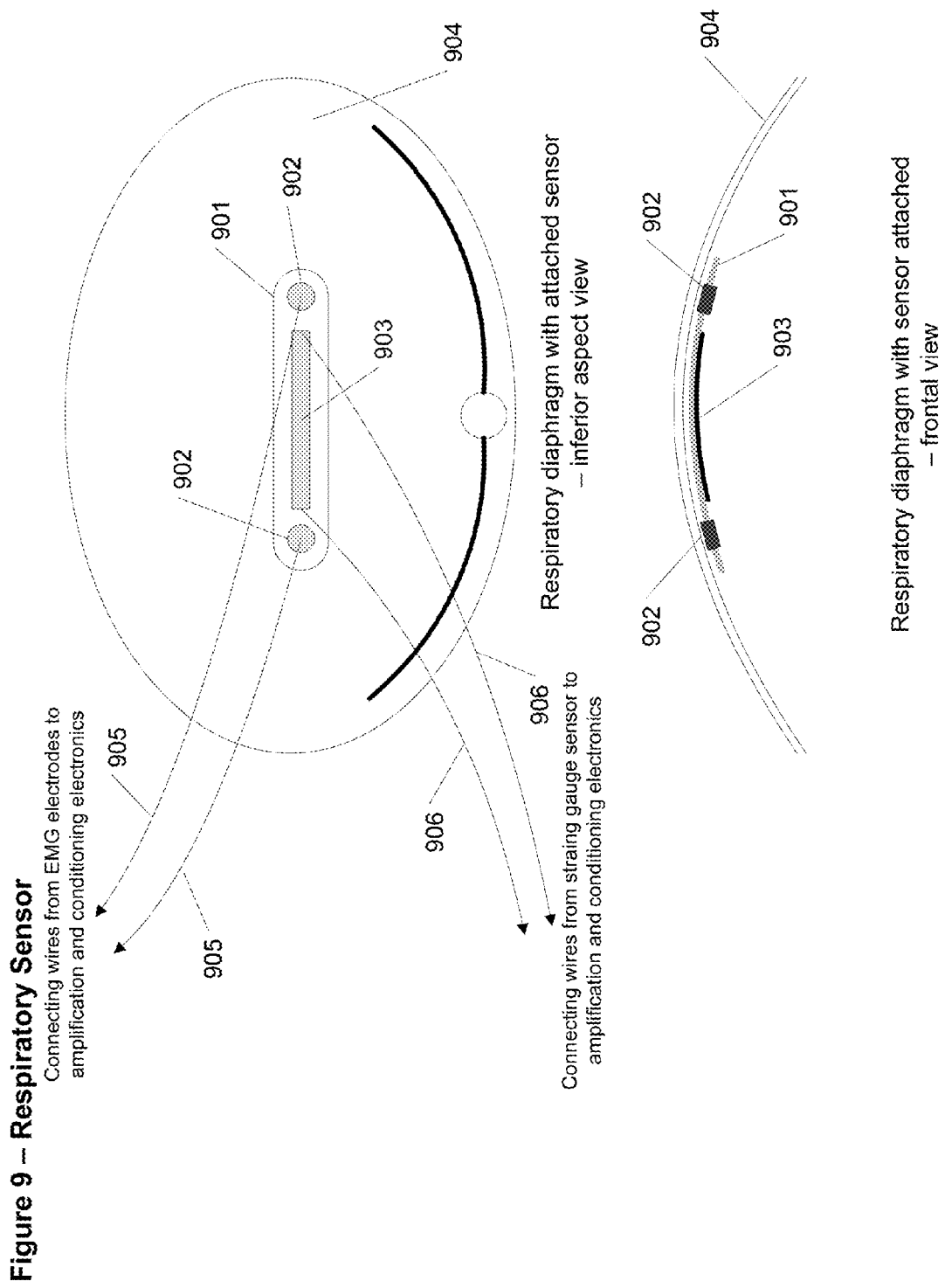
FIG. 9 shows a respiratory sensor for attachment to the respiratory diaphragm, in connection with another example embodiment of the present invention.

In another embodiment, respiration is sensed using a sensor attached to the diaphragm of an experimental animal. This can be useful to obtain accurate measurements of respiratory rate and tidal volume from a single sensor assembly that can be surgically placed on the respiratory diaphragm. Referring to FIG. 9, patch 901 is fabricated of a flexible material, such as a Dacron fabric or an insulating polymer, containing a pair of EMG sensing electrodes 902 and a strain gauge 903 that is attached to surface of the respiratory diaphragm. A conductive surface of the EMG electrodes is exposed on the side of patch 901 facing the respiratory diaphragm. In one embodiment, electrodes 902 have a surface area of about 5 to 10 square mm and are fabricated of an inert metal such as titanium, MP35N, or stainless steel 316L. In some implementations, the conductive surface of the electrodes is roughened by sintering, etching, or another process in order to improve the electrical contact between the electrodes and the diaphragmatic tissue. In some embodiments, a coating such as platinum is applied to the conductive surface to provide a reduced half-cell potential. Connecting wires 905 are attached to each electrode on the side opposite the diaphragm to connect to amplification and conditioning electronic circuits in TAMD 101.

In one embodiment, strain gauge 903 is adhered to the side of patch 901 opposite the diaphragm and senses deflection in the diaphragm during respiration. Strain gauge 903 is chosen of a type that provides spring constant when deflected by the diaphragm in order to allow the diaphragm to move relatively freely. Various strain gauges can be used, such as those of a type such as a piezoresistive or piezoelectric mechanism. In one embodiment, piezoelectric strain gauge 903 includes a piezoelectric nanowire such as that described in [22]. The signal produced by strain gauge 903 is proportional to the degree of deflection and is nominally proportional to the depth of respiration. Connecting wires 906 are attached to strain gauge 903 to conduct the signal to electronics for amplification and conditioning in TAMD 101.

In one embodiment, the side of patch 901 facing the diaphragm is fabricated of or coated with a material that quickly promotes the growth of adhesions, such as Dacron. This is used to promote rapid stabilization of the patch following placement and in some situations preclude the need for sutures to hold patch 901 in place, facilitating rapid deployment. The side of patch 901 away from the diaphragm is fabricated or coated with a material that will not promote adhesions, such as silicone, in order to reduce the risk of adhesions to the abdominal organs. In one embodiment, the length of patch 901 is about 35 to 75% of the lateral dimension of the diaphragm. This distance provides for strong signals from both sensors and improved correlation of signal amplitude with depth of respiration, especially for the signal derived from the strain gauge. In some embodiments where interference with function of the diaphragm is of concern, the length of patch 901 is reduced to about 15 to 25% of the lateral dimension of the diaphragm to reduce the area of scar tissue on the diaphragm.

Processing EEG/ECoG Signals.

Figure 10:
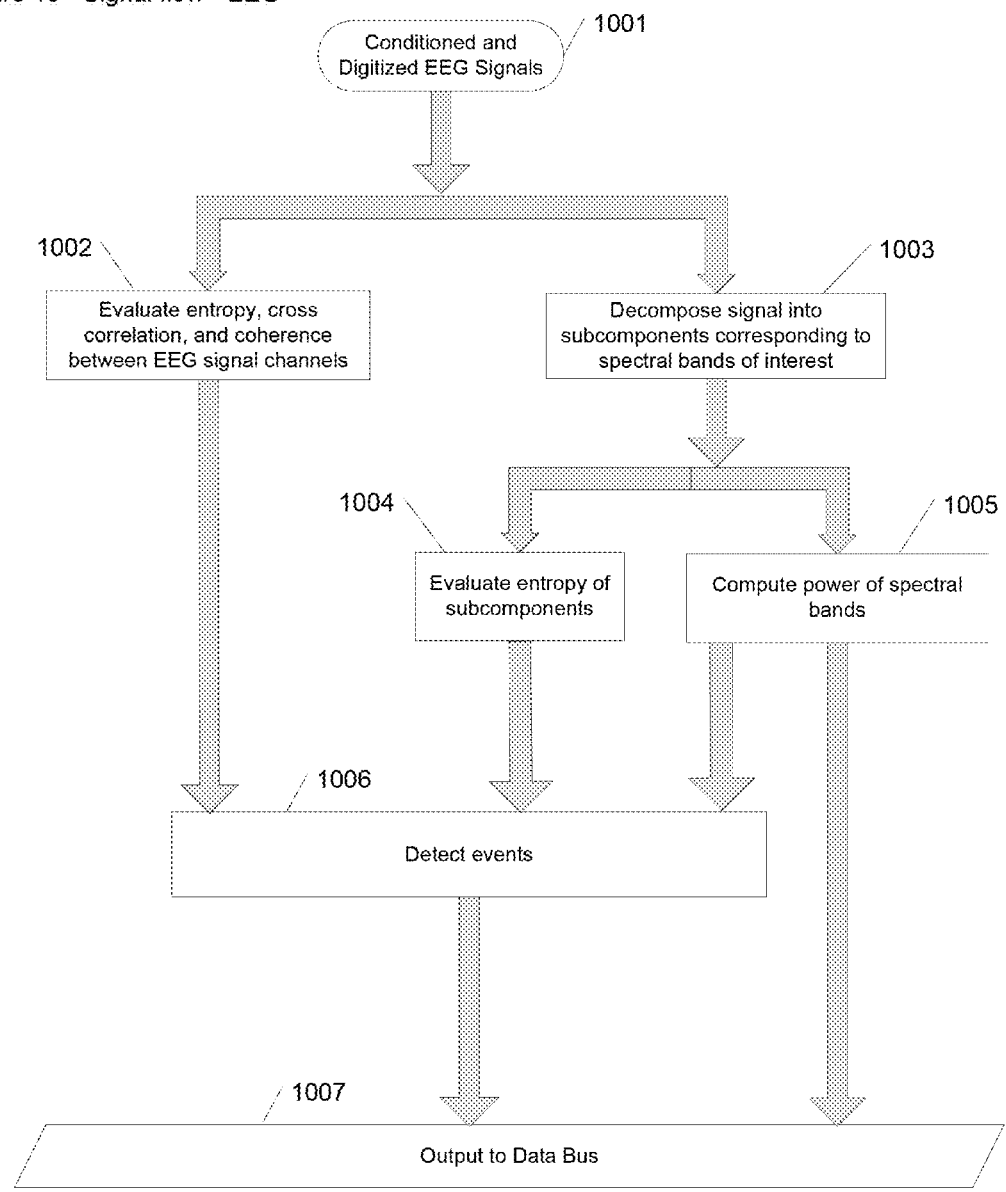
FIG. 10 shows an example data flow block diagram for processing of EEG signals, in connection with another example embodiment of the present invention.

Referring to FIG. 10 and in accordance with another example embodiment, EEG and ECoG signals are processed to compute the power in frequency bands of interest and to detect events such as epileptic events and sleep stages. In an example embodiment, and referring to FIG. 10, a multichannel EEG signal input in 1001 is decomposed into subcomponents corresponding to spectral bands of interest in process 1003. Spectral bands of interest can include, for example, those associated with alpha, beta, theta, delta, and gamma. In process 1002, the entropy of the input EEG signals is evaluated using techniques such as approximate entropy and multiscale entropy. In addition, cross-correlation and coherence between signal channels is computed. If entropy is low and correlation is high, it is indicative of a high level of organization of brain waves, such as would occur during an epileptic event or REM sleep. In process 1004, entropy of subcomponents is evaluated using a technique such as approximate entropy. In process 1005, the power or amplitude of selected spectral bands is computed from the related subcomponents and compared to a threshold. Detection of an event in process 1006 is based upon a weighted combination of the output of processes 1002, 1004, and 1005. For example, in the case of an epileptic event, process 1005 would indicate an elevated power in selected spectral bands. Process 1004 would indicate a low-level of entropy of subcomponents and process 1002 would indicate high coherence and low entropy between signal channels during an epileptic event.

Evaluation of the power in defined frequency bands provides the researcher with information on brain functioning including sleep stage, depth of anesthesia, cognitive state of the subject, and the brain centers impacted by a particular drug. In some embodiments, in response to detecting a significant event, capture of the EEG is triggered before and after a relevant transition occurred in order to confirm the shift in EEG pattern or to allow further analysis, either through the use of additional processing in DCRS 106, or through evaluation by an operator skilled in review of EEG waveforms.

In some embodiments other feature signals and denoised signals are evaluated in combination with EEG in order to improve the accuracy of detection. For example, evaluation of EMG in combination with EEG may improve the accuracy of detection of certain types of epileptic seizures.

By processing the EEG within TAMD 101 in the manner described here, the volume of data requiring transmission and the power required to transmit data can be substantially reduced. By implementing the signal processing algorithm efficiently within TAMD 101, the power required to process the data is much less than the power that would be required to transmit the waveforms for analysis in the data review system. Hence, a net reduction in current consumed by TAMD 101 can be achieved.

Processing PNA Signals.

Figure 11:
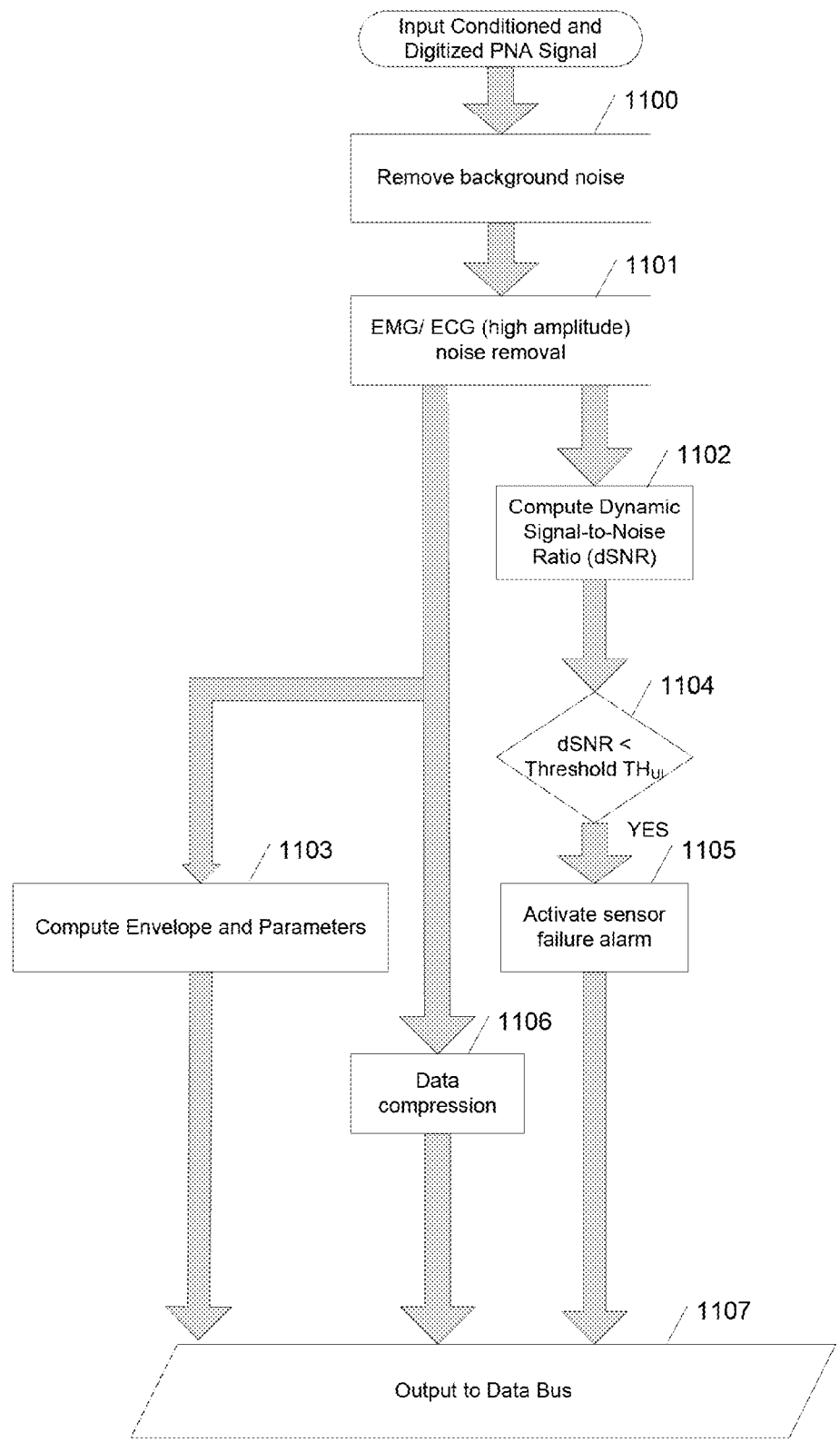
FIG. 11 shows an example data flow block diagram for processing of a peripheral nerve activity (PNA) signal, according to another example embodiment of the present invention.

In connection with various embodiments, and referring to FIG. 11, signals from a peripheral nerve, referred to as peripheral nerve activity (PNA), are conditioned (e.g., amplified and filtered to remove out-of-band noise) and digitized and the digitized signal is processed to remove noise and extract information using a computerized algorithm. In some embodiments, a sensor used to capture PNA signals includes multiple conductive elements (electrodes) secured on or around a nerve that pick up the electrical activity associated with nerve firings. The embodiments described here are particularly well suited to situations where the number and frequency of firings of nerve fibers contained within a nerve bundle is of interest.

The signal sensed by the electrodes is conditioned and digitized, in which conditioning includes amplification and filtering with an antialiasing filter as well as high pass filtering to remove baseline fluctuations. In some embodiments, the filtering provided in the conditioning process removes most of the out-of-band noise. The conditioned and digitized signal is denoised to remove at least some of the noise present in the captured PNA signal by, for example, electrical interference from radiated electromagnetic energy sources, noise introduced by the amplifier, ECG, EMG, or other sources. An envelope is computed for the denoised signal to provide a signal indicating the time course profile of neural activity that is used as an indicator of amplitude and frequency of nerve firings in the nerve bundle.

In some embodiments, and referring to FIG. 11, the denoised PNA signal is compressed in process 1106 in order to reduce the volume of data that must be telemetered in order to reduce current required by TAMD 101 to wirelessly communicate the signal to DCRS 1106. Communication of the denoised and compressed PNA signal may be enabled on demand by the user via a command entered in the DCRS user interface 305, or it may be enabled automatically by TAMD 101 at regular or pseudorandom intervals of time. The transmitted PNA waveform (either denoised or the raw signal) can be used for troubleshooting to assess the viability of the sensing electrodes or to verify the accuracy of the signal processing algorithms on board TAMD 101.

In an example embodiment for denoising the PNA signal, and referring to FIG. 11, the input conditioned and digitized PNA signal is processed in 1100 to remove low-amplitude background noise such as that introduced by the amplifier or radiated emissions. Several methods can be used to remove background noise [3, 23, 24]. In one embodiment, the input PNA signal is decomposed into subcomponents, decomposition coefficients that are below a pre-specified threshold rule are deleted. The threshold can be identified in a variety of manners, such as by using a technique described by Donoho [3]. In one embodiment, the decomposition is wavelet-based and the background noise removal is accomplished by wavelet thresholding.

Following removal of background noise in process 1100, high amplitude noise such as EMG or ECG noise is removed in process 1101. In one embodiment, high amplitude noise is removed by decomposing signals collected in a first domain into a second domain of higher dimension than the first domain. In some embodiments, decomposition is accomplished using a discrete cosine transform [4], Fourier transform [5], Gabor transform [6] or Karhunen-Loeve transform [7,8]. In another embodiment, decomposition is accomplished using a wavelet-related transform and the decomposition levels correspond to wavelet scales. Decomposition coefficients corresponding to high amplitude noise, such as ECG and EMG, are identified by using PCA, ICA or spatially selective filtering as described in U.S. patent application Ser. No. 12/938,995, referenced above. Once identified, ECG and EMG noise is removed by deleting the identified coefficients. The residual signal subcomponents are used to reconstruct a denoised signal in the first domain.

In another embodiment, an envelope of the denoised PNA signal is used to provide an indication of amplitude and frequency of nerve firings to quantify neural activity. The envelope can be computed by rectification and bin-integration of the denoised signal [25]. In one embodiment, the envelope is computed as the square root of the energies of the original and the orthogonal components of the signal. The orthogonal component can be computed by using a Hilbert transform of the denoised signal. In yet another embodiment the envelope can be computed as the sum of low-pass filtered original and orthogonal components of the signal.

In various embodiments, the resulting envelope is used to indicate the frequency and amplitude of bursts of peripheral nerve firings and provide insight into the degree of nerve fiber recruitment. Nerve fiber recruitment is measured and used to provide insight into the role of peripheral nerves in regulation of physiological function and in the titration of neural stimulation therapies. The bursts of peripheral nerve firings are the result of coordinated firing of individual nerve fibers and the amplitude and frequency of these bursts carry information about the proportion of fibers recruited and their response to physiologic changes. These bursts can be detected using peak detection methods such as fixed or adaptive threshold methods. These threshold methods can be applied to the envelope or a signal derived from the envelope that emphasizes the peaks. In one embodiment, the peaks are emphasized by applying a differentiator filter to the envelope. The detected peaks can be further processed to report PNA parameters such as frequency, amplitude, and incidence of bursts per cardiac cycle in addition to average level of neural activity over time.

In addition to sympathetic nerves, this same approach can be used to quantify neural signals acquired from other peripheral nerves such as parasympathetic nerves and motor neurons.

In another embodiment, the evoked response from a periodic stimulation of a nerve is measured in the vicinity of the nerve to diagnose and evaluate pain. Electrodes used to sense these signals can include needle electrodes that are inserted through the skin with the tip placed near a nerve, using approaches as described herein to process such signals as may be characterized by low SNR and a limited number of observed channels. In some implementations, these signals are segmented in the time domain based upon knowledge of timing of stimulation. Segmentation in the time domain facilitates the creation of the equivalent of multiple channels from the observed signal, hence increasing the number of dimensions in the first domain. The signals are decomposed into a second domain and noise and signal subcomponents are discriminated using principal component analysis and spatially selective filtering, using approaches such as described in U.S. patent application Ser. No. 12/938,995, referenced above. This denoising facilitates evaluation of the evoked response of thin nerve fibers responsible for pain signaling (e.g., A-delta and C fibers).

Reporting Arrhythmia Information of a Subject

Figure 12:
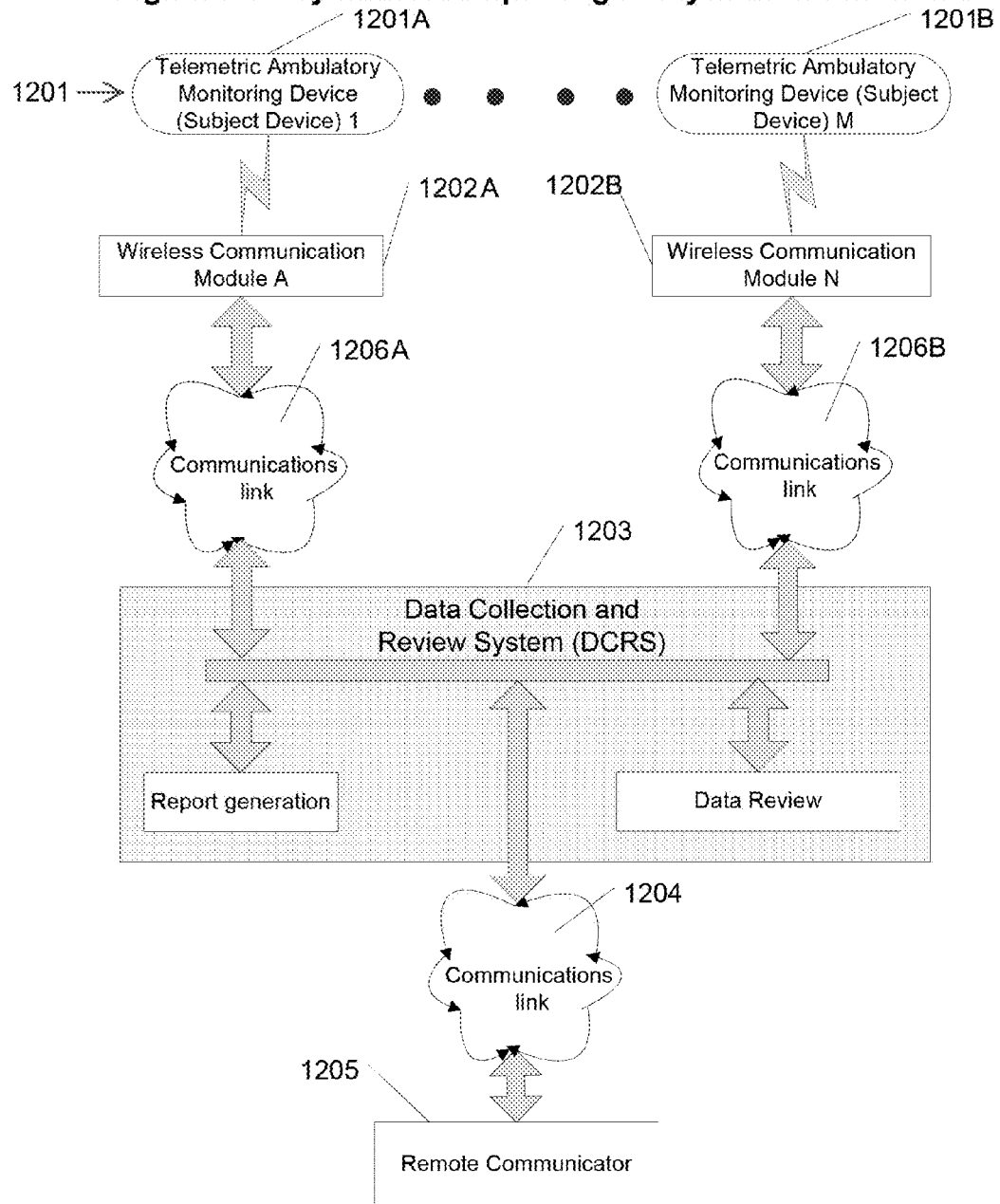
FIG. 12 shows a block diagram of a system for reporting arrhythmia information, according to another example embodiment of the present invention.

In some embodiments, and referring to FIG. 12, a system is configured for reporting an arrhythmia summary of subjects evaluated for the presence of cardiac arrhythmias. This can include human and animal subjects whose health is at risk due to cardiac arrhythmias and human and animal subjects that are being evaluated for arrhythmias as part of a clinical or preclinical trial of a device or drug. TAMD 1201 (examples shown as 1201A and 1201B) is worn by or implanted within a subject. TAMD 1201 senses and processes ECG signals to identify arrhythmias and other information such as parameter values and wirelessly transmits the information to a wireless communication module connected to communications link 1206 (examples shown as 1206A and 1206B). In one embodiment, communications link 1206 is a cellular data network or wide area network such as the Internet. The arrhythmia and other information is received at DCRS 1203. Arrhythmia events are classified as to their type (e.g., VT, bigeminy, atrial fibrillation, etc.) and a report is e compiled and forwarded to remote communicator 1205 via communication link 1204. In some embodiments remote communicator 1205 is a PC or smart phone capable of accessing a web site or receiving email. Communications link 1204 may be a wide area network such as the internet or a cellular network. Reports may be received by email, fax, or via a website.

Figure 13:
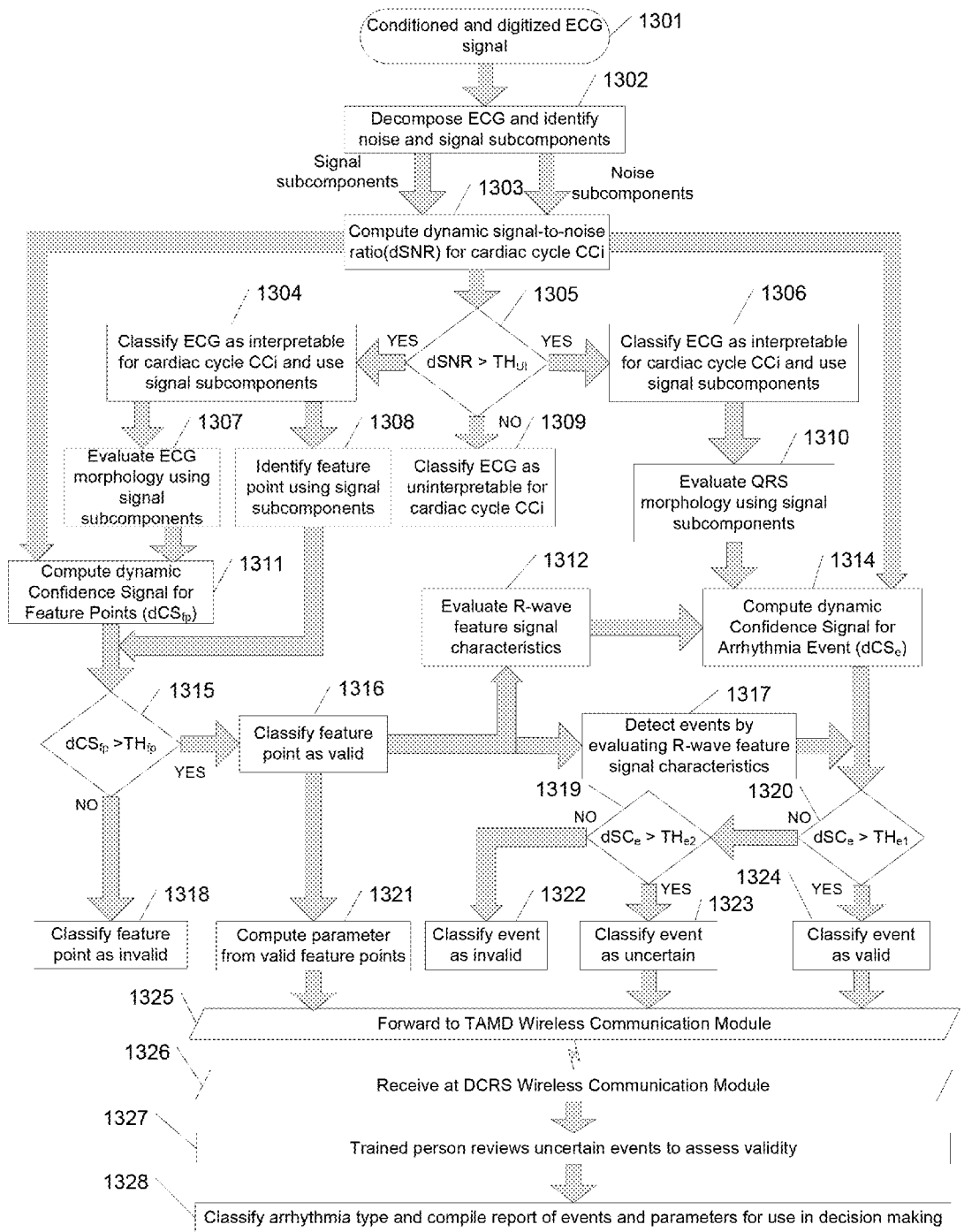
FIG. 13 shows a block diagram for a process and decision flow in a system for detecting, classifying, and reporting arrhythmia events, according to another example embodiment of the present invention.

In accordance with example embodiments, referring to FIG. 13, identification of feature points, computation of parameters, and detection, classification, and validity assessment of events takes place within TAMD 1201. For additional detail regarding approaches to signal decomposition, identifying signal and noise subcomponents, denoising, and identifying feature points and arrhythmic events that may be implemented herewith, reference may be made to U.S. patent application Ser. No. 12/938,995, referenced above. Conditioned and digitized input signals 1301 are decomposed into subcomponents and signal and noise subcomponents are identified in process 1302. In process 1303, the ratio of energy in signal and noise subcomponents is computed as dynamic signal-to-noise ratio (dSNR). dSNR in process 1303 is computed for a cardiac cycle, and can also be computed for regions within a cardiac cycle such as a segment in the vicinity of T-wave offset. In decision process 1305, dSNR is compared to a threshold $TH_{UI}$. If dSNR exceeds the threshold, the signal is classified as interpretable and the signal-related subcomponents are passed downstream via 1304 and 1306 for additional processing and reconstruction of a denoised ECG signal as needed. If dSNR is less than $TH_{UI}$, then the segment is classified as uninterpretable (process 1309) (e.g., meaning that no useful information can be extracted or identified in the signal, even if reviewed by a trained person). In alternate embodiments, identification of uninterpretable segments could be performed following detection of events and feature points.

In process 1308, feature points are identified. In one embodiment, feature points are identified by combining relevant signal subcomponents to create one or more feature signals. Feature points of interest include R-wave peak, P-onset, Q-onset, S-offset, and T-wave offset. The peaks and valleys of each feature signal are evaluated, as appropriate, to identify feature points of interest. In process 1307, morphology is evaluated for use in assessing the validity of a feature point. In one embodiment, morphology is evaluated by combining appropriate subcomponents to form an emphasis signal. The peaks and valleys of the emphasis signal are evaluated to identify the presence of relevant morphologies. The specific type of morphology of interest depends upon the type of feature detected for which validity is being assessed. In one embodiment, the R-wave feature signal is used for detecting events since it is the easiest and most reliable to detect. The output of the morphology evaluation process 1307 functions as a multiplier, $M_i$, to provide an output equal to 1 if morphology indicates that it is likely that an R-wave exists and 0 if not. To compute the dynamic Confidence Signal ($dCS_{fp}$) for an R-wave feature point in process 1311, then $dSC_{fp} \approx M_i * k * dSNR$ where Mi is 1 or 0, dSNR is the dynamic signal to noise ratio, and k is a constant that depends on the type of feature point for which $dSC_{fp}$ is being evaluated.

In decision process 1315, $dSC_{fp}$ is compared to a threshold $TH_{fp}$. If the threshold is exceeded, the feature is classified as valid in process 1316 and, in some embodiments, valid features (e.g., R-R interval) are combined to compute a parameter (e.g., heart rate) in process 1321. If the threshold is not exceeded, the feature point is classified as invalid and ignored for the purpose of computing a parameter, as in process 1318.

In process 1310, the morphology of the QRS complex is evaluated (e.g., in a process similar to that described for process 1307). In process 1314, a dynamic Confidence Signal for ECG arrhythmic events ($dCS_e$) is computed. In one embodiment, $dCS_e$ is a function of the dSNR computed in process 1303, the morphology evaluation in process 1310, and the R-wave feature signal characteristic evaluation in process 1312. For example, when detecting ventricular tachycardia (VT) from an ECG, the feature signal would be evaluated to assess the heart rate. If the heart rate exceeds the threshold established for detection of VT, then the QRS complex is evaluated for morphology typical of a beat initiated in the ventricle.

Evaluated feature point characteristics that may impact $dCS_e$ include rate and regularity. For example, if the heart rate computed from an ECG exceeds a threshold, it may be indicative of high levels of EMG noise. In some implementations, process 1312 is configured to trigger process 1314 to consider the morphology of the ECG signal based upon such feature point characteristics. If morphology evaluation indicates the presence of a high-amplitude EMG signal, the value of dCSis driven low and the event would be deemed invalid. The output of the morphology evaluation process 1307 functions as a multiplier equal to 1 if morphology indicates that an event could be valid and 0 if not. The $dSC_e \approx M_i * k * dSNR$ where Mi is 1 or 0, where dSNR is the dynamic signal-to-noise ratio, and k is a constant that depends on the type of event for which $dSC_e$ is being evaluated. Arrhythmic events are detected in 1317 in a process involving evaluation of feature signal characteristics. For example, a highly irregular heart rate could be indicative of atrial fibrillation. As another example, a feature signal indicating a high heart rate may indicate the presence of VT while a pattern of one fast beat followed by one slow beat would indicate the presence of a bigeminy.

In decision process 1320, $dSC_e$ is compared to a threshold $TH_{e1}$ to determine if the event detected in process 1317 is valid. If threshold $TH_{e1}$ is exceeded, the event is classified as valid. If threshold $TH_{e1}$ is not exceeded, then $dSC_e$ is compared to a second threshold $TH_{e2}$, where $TH_{e2} < TH_{e1}$. If $TH_{e2}$ is exceeded, then the detected event is classified as uncertain, meaning that the detected event is either valid or invalid. If $dSC_e < TH_{e2}$ then the detected event is classified invalid. In some embodiments, threshold $TH_{e1}$ is chosen such that if $dSC_e > TH_{e1}$ the likelihood of that the event is valid is so high that there it isn't justifiable to have a trained person review the event and it can therefore be included in an arrhythmia report without further review. Likewise, $TH_{e2}$ may be chosen such that if $dSC_e$ is $< TH_{e2}$, then the event is invalid with a very high likelihood. In this case, review by a trained person is determined as not justified and the event is excluded from the arrhythmia report. In some embodiments, the process used to create the arrhythmia report recommends that events classified as uncertain be reviewed by a trained person to assess validity. In other embodiments, the process used to create the arrhythmia report uses a cost-benefit of reviewing events classified as uncertain as inputs to a weighting algorithm, and concludes that review is unjustified in response to the incidence of uncertain events being smaller than a threshold. This embodiment can be used when arrhythmia events or arrhythmia reports are communicated directly to a patient for the purpose of managing their own health.

In one embodiment, parameters computed in process 1321 and ECG waveforms for uncertain events and valid events are forwarded to TAMD wireless communication module in process 1325 and are communicated to wireless communication module 1202 (with examples shown as 1202A and 1202B). Wireless communication module 1202 can be located near the monitored subject and is capable of communicating with TAMD 1201 using a short-hop communication technique such as Bluetooth or the Medical Information Communication Service. Communication module 1202 is in communication with a means of accessing the internet or cellular network to forward the information to DCRS 1203 where the information is received in process 1326. A trained person reviews uncertain events in process 1327 and decides whether those events are valid or invalid. In process 1328, arrhythmias are classified as to their type (e.g., VT, bigeminy, supra-ventricular tachycardia, trigeminy, atrial fibrillation, etc.) and valid arrhythmic events and parameter information are incorporated into the arrhythmia report in process 1328 for use in decision making. The report may include the prevalence of various types of arrhythmias as well as denoised waveforms for all or some of the valid arrhythmia events detected. In some embodiments, parameter information may also be included in the report including heart rate, QT interval, PR interval, and QRS duration. Decision making may include use of the information to decide upon a therapy regimen for a patient being treated for arrhythmias or it may include decisions on the safety and efficacy of an experimental therapy. Capture of Denoised Waveforms for Communication to Data Review System.

In some embodiments, TAMD 101 captures the denoised signal for a specified duration or stores multiple consecutive durations of a denoised signal waveform and stores it in memory element 205 of TAMD 101 for later communication to the data review system. A waveform strip or contiguous multiple waveform strips are captured to validate the accuracy of a feature signal created within TAMD 101, for performing specialized analysis off line by the researcher, for trouble shooting, or to provide a continuous recording to satisfy regulatory or study protocol requirements. In some embodiments compression is applied to the denoised waveforms prior to wireless communication to reduce power consumed in the communication module and to increase effective memory space. In one embodiment, capture of a waveform strip for real time or later transmission is triggered by detection of an event or an alarm. In another embodiment, capture of a waveform strip is triggered automatically by the computerized controller of TAMD 101 based upon lapse of predetermined time intervals. Time intervals at which waveform strips are automatically captured can be regular or pseudorandom.
Compression In connection with various example embodiments, and referring to FIG. 14, waveform signals are compressed prior to wireless communication in battery powered subject devices such as TAMD 101 and 1201 in order to reduce the volume of data to be transmitted. In some embodiments involving TAMD 101 and 1201, when compression is implemented efficiently, computing a compressed signal requires less energy than wirelessly communicating the uncompressed signal, thereby increasing battery life.

The choice of compression scheme is dependent upon the ability of a given scheme to leverage redundancies in the signal. In some embodiments, compression factors for signals exhibiting pseudoperiodic behavior such as ECG can be as high as 20 and when compression is computed in an efficient manner, resulting in more than a factor of 12 extension in battery life when full disclosure ECG waveforms are transmitted. Beyond computational efficiency and compression factor, it is also important to consider the degree of distortion introduced by the choice of compression scheme. Many compression schemes sacrifice signal fidelity in exchange for a high compression ratio and hence sacrifice the accuracy and clinical utility of the transmitted signal. The ideal compression scheme is therefore one that has a high compression ratio, exhibits negligible distortion following compression and decompression, and can be implemented very efficiently in an embedded system. For additional detail regarding one or more approaches to compression as may be implemented in accordance with various example embodiments, reference may be made to U.S. patent application Ser. No. 12/938,995, referenced above.

For signals exhibiting a quasi-periodic nature such as ECG, blood pressure, flow, pulse oximetry, and respiration relatively high rates of compression are achieved by leveraging the redundancy present in consecutive cardiac cycles. In one embodiment, and referring to FIG. 14, a denoised quasi-periodic signal is segmented by cardiac cycle or respiratory cycle using detected features in process 1403. Also in process 1403, cycles are sorted by length to increase the degree of redundancy in a two-dimensional (2D) image plot created in process 1405. This two-dimensional image shows consecutive cardiac or respiratory cycles in one dimension and the tracing of each cardiac cycle in the other dimension. A sorting table is created in process 1404 documents the location of each cardiac cycle within the two-dimensional sorted image. This table is transmitted to the DCRS along with the compressed image and is used in the decompression process to properly order the cardiac cycles prior to reconstruction. The 2D image created in process 1405 is compressed in process 1406 using techniques that leverage redundancies between adjacent cardiac cycles. In some embodiments, redundancies across adjacent subbands or wavelet scales are utilized by wavelet or cosine transforms of the image. Examples of techniques that could be utilized to achieve efficient compression of the 2D image in process 1406 include embedded zerotree wavelet (EZW) [26], set partitioning in hierarchical trees (SPIHT) [27], modified SPIHT [28] and embedded block coding with optimal truncation (EBCOT) encoding algorithms [29].

When compressing a signal, the compression factor is affected by the level of noise present in the signal, as noise reduces the degree of redundancy in adjacent cardiac cycles. Denoising the signal prior to compression using an MDSP approach as discussed herein is used in such situations to provide for improved compression ratios. Another attribute of such MDSP approaches that can be used to achieve an improved compression ratio is the ability to very accurately detect the cardiac cycle (e.g., QRS complex of an ECG) and accurately and consistently identify a fiduciary point in the cardiac cycle (e.g., the peak of the R-wave). This allows the cardiac cycles to be precisely aligned in the two dimensional image. This not only increases the redundancy between adjacent cardiac cycles, and hence improves the compression ratio, it also reduces the signal distortion resulting from the compression-decompression process. Another attribute of MDSP that can be used to improve compression performance (in connection with various embodiments) involves accurately and reliably identify segments of an ECG that are uninterpretable (e.g., have no useful information, even when reviewed by a trained person). Since segments classified as uninterpretable have no useful information, in some applications, these segments are replaced with zero-value samples and imposing an artificial cardiac cycle length as a function of the length of other cardiac cycles observed in the subject. Doing so will increase the redundancy between adjacent cycles and hence will increase the compression ratio and reduce TAMD power consumption.

In another embodiment, an efficient compression of a quasi-periodic signal is accomplished by phase wrapping cardiac cycles and converting the source signals into a polar or cylindrical system of coordinates [30]. The signal is efficiently represented by a 3 dimensional plot of phase-aligned cardiac cycles and compressed.

In another embodiment an ECG signal is compressed by calculating and subtracting a reference P-QRS-T template from detected normal P-QRS-T complexes. The residual data is low-filtered, decimated and compressed using differential and entropy based encoding. The reference beat is encoded using lossless encoding techniques.

For signals such PNA and EMG, where the denoised signal is often sparse but may not be characterized as pseudoperiodic, other approaches are carried out to achieve high levels of compression. The sparse signal can be compressed by any of several compression schemes such as direct time-domain coding or transform based coding [31]. Sparse characteristics of such signals are used to facilitate the effective denoising with these approaches to achieve efficient compression (e.g., of PNA and EMG signals).

For signals such as EEG, which are characterized by high entropy, transform based coding is used to improve compression rate.

Communication Modules.

In one embodiment, a bidirectional communication module 207 is located in each TAMD 101. This communication module receives commands and control parameters from the data collection system. Examples of commands received by TAMD 101 may include which types of features are to be extracted, which parameters are to be computed and how often, alarm trigger thresholds, sampling rates, dCS and dSNR threshold levels, event detection criteria, and confidence threshold levels. A communication module located in the data collection system communicates with the TAMD. In various embodiments, the communication modules employ low-energy Bluetooth communications, Zigbee, 6 LoWpan, or proprietary communication protocols can be employed on any of the ISM frequency bands, 916 and 400 MHz, for example.

Data Collection and Review System (DCRS).

In connection with various example embodiments, a data collection and review system (DCRS) as discussed herein is, along with communication modules, implemented as part of a data collection system as shown in FIG. 3. In one embodiment, the DCRS provides three primary functions: a) an input device/circuit for allowing a user to enter control functions and operating parameters for communication to TAMD 101 via user interface software 305, b) compressed signal reconstruction via process 306, storage and archival information received from the TAMD via data and program memory 307, c) review, display, analysis, classification, and report generation for information received from the TAMD, and d) control of remote alarm and communication functions to provide a warning to a remote communication device that an alarm has occurred. In one embodiment the DCRS stores data in compressed form and reconstructs upon retrieval in order to save disk and backup media space.

Figure 15:
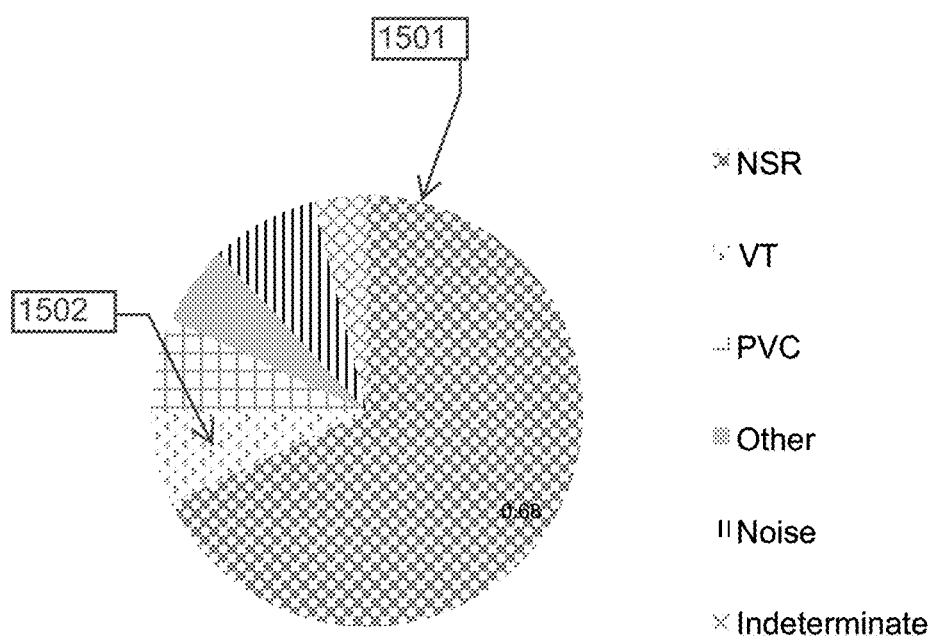
FIG. 15 shows an example pie chart graphic for display of arrhythmia event information by the data review system, consistent with another example embodiment of the present invention.

In one embodiment, and referring to FIG. 15, statistical analysis of extracted features, parameters and events are displayed as pie chart 1501. This allows a user to quickly view the types and prevalence of arrhythmias present. In one example, pie chart 1501 displays the breakdown of the % prevalence of each type of event/rhythm present is a specified time period. In this example, the percentage of each of the following classifications for the time period are normal sinus rhythm (NSR), ventricular tachycardia (VT), premature ventricular contraction (PVC), segments in the time period classified as uncertain, and segments in the time period classified as uninterpretable. In one example, the user may elect to display a pie chart for a 24-hour period. Once displayed on the pie chart, the user can click on a segment of the pie chart to display the recorded events/signals for the selected classification. For example, if the user clicked on pie chart slice 1502, VT events would be displayed. In one embodiment, the waveform is displayed with markers showing the location of identified feature point (QRS detections, T-wave offset, etc.).

In one embodiment the collected data are organized into a database that enables efficient querying approaches, information retrieval and data mining tools. An example of such database is data warehouse which includes tools to extract, transform, and load data into the repository.

In another embodiment, referring to FIGS. 1 and 3, the DCRS facilitates communications with a slave computing device 304 that runs applications that can interact with the DCRS. Communication link 302 may include one or more of a local area network, wide area network, or cellular data network. The addition of the application portal facilitates user customization of the system without the need to change the core programming in the DCRS This facilities customer or manufacturer customization or functionality changes while preserving the integrity and reliability of the core system. This approach can be used when the core system is used to collect data in GLP studies where validation can be very expensive and time consuming. Through the slave computing device, functionality can be added for those customers that want it without providing updates to the core system that would drive a need for a new validation effort for GLP customers that may not have a need for the added functionality. For example, in one embodiment, the functionality of the core DCRS system is limited to collection of data received from TAMD 101, providing rudimentary statistical analysis such as group mean statistics, dose response curves, and providing the ability to review the collected data and statistical results.

In one embodiment, the system is used in an animal study of thermoregulation. DCRS 106 communicates collected data to slave system 304 in real time. Slave computing device 304 evaluates the received data and controls application of power to cooling and heating elements in the animal's environment as a function of data collected by DCRS 106. This functionality could be added to the slave system without any changes to DCRS 106.

The communications link 302 may include a wired or wireless communication interface and may employ USB, Bluetooth, Ethernet, serial, parallel digital, or infrared communications. The DCRS 106 and communications link 302 is configurable for communicating information on a delayed basis or in real time. Slave computing device 304 processes the information received from the data review system and uses it to perform a useful function such as extracting additional information, providing a data display function, or providing a control function as part of an experimental protocol. In some embodiments, slave computing device 304 is a personal computer outfitted with the necessary peripheral devices to perform the required functions. For example, slave computing device 304 can provide analysis or processing of the data communicated to it by the data review system and can act on the data, providing information to the user that is customized to their specific needs or it can communicate a signal back to the data review system that can initiate a change in configuration or operation. Slave computing device 304 can display the results of the additional analysis or processing, or take action to implement some useful function, including providing a feedback control to an experimental protocol.

In another example, TAMD 101 streams real time data to slave computing device 304 via communication link 302. Device 304 is interfaced to a control mechanism capable of administering a drug to an experimental subject. Device 304 evaluates the real time data received from DCRS 106 and uses it to adjust the administration of a drug to a laboratory animal subject via the control function of Device 304. This added functionality of using data received from TAMD 101 to control administration of a drug is accomplished without change to DCRS 106 and only involves modification of slave computing device 304.

In another example, TAMD 101 sends an alarm to DCRS 106 indicating that an arrhythmic event has occurred in a subject. Slave computing device 304 has been programmed by the customer to automatically change the configuration of TAMD 101 to continuously transmit a denoised signal to DCRS 106 if such an event were to occur. Upon receiving the alarm signal from DCRS 106 that the event occurred, device 304 communicates an instruction back to DCRS 106 which in turn communicates an instruction to TAMD 101 to provide transmission of a continuous denoised signal.

In yet another example, TAMD 101 sends an alarm message that the heart rate of an experimental animal has fallen below a rate needed to sustain life for a predetermined period of time, indicating that the experimental animal subject has died. The alarm is received by DCRS 106, which in turn sends a message via communication link 302 to remote communication device 303. In this example, remote communication device 303 is a pager worn by laboratory personnel. Upon receiving the message, the person makes arrangements to perform an autopsy on the experimental animal as soon as possible. In yet another example, the alarm message indicates that a patient wearing TAMD 101 has experienced a life threatening event such as VT. DCRS 106 receives the message and forwards it via communication link 302 to remote communications device 303, which, in this example, is a console at an emergency response center. In response, the emergency response center dispatches an ambulance to the patient's location.

In one embodiment TAMD 101 is constructed so as to fit in a small and lightweight housing that incorporates electronics for sensing, amplifying, and digitizing one or more ECG signals, a computing device for executing computerized instructions for processing the ECG signals (e.g., for removing noise from the signals), and a battery to power said electronics. In other embodiments the computing device also performs one or more of storing denoised ECGs for later retrieval, detecting arrhythmias, and measuring ECG intervals such as QT interval. In other embodiments TAMD 101 provides a wireless, wired, or removal media function to communicate ECGs and extracted information to DCRS 102. In some implementations, the TAMD 101 includes a fastener that fastens the TAMD 101 to an electrode, with TAMD 101 being of size and weight to be supported by the electrode and an adhering material that adheres the electrode to a patient.

Figure 16:
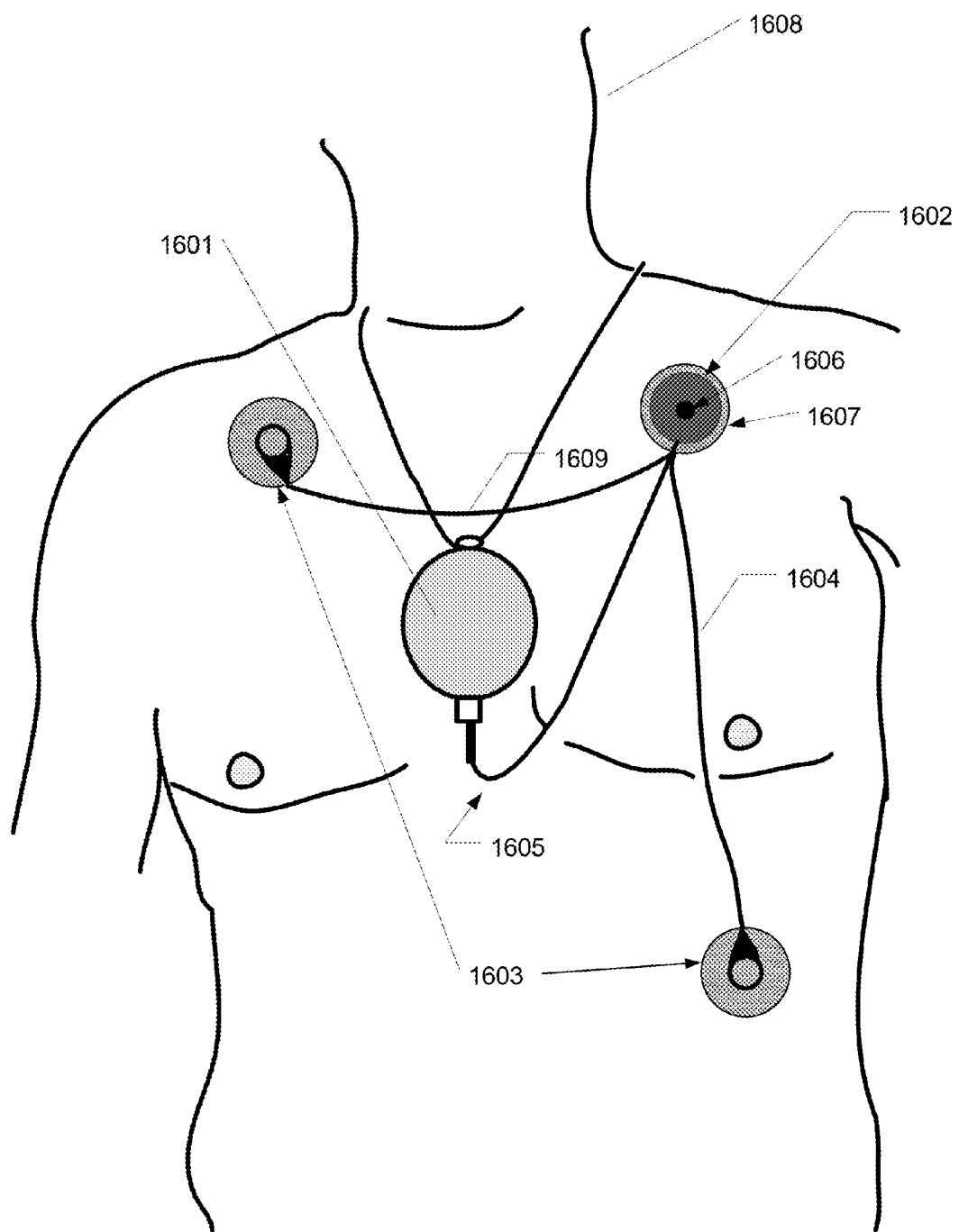
FIG. 16 shows an apparatus for recording ECG signals, in accordance with another example embodiment.

In one embodiment, and referring to FIG. 16, TAMD 1602 processes a two-lead ECG signal to remove noise, is packaged in a small and lightweight housing (e.g., <15 cc in volume and that weighs <15 grams), and incorporates an ECG electrode snap 1606 on one side such that it can be attached directly to surface ECG electrode 1607 such as a 3M (St. Paul, Minn.) Model 2259. In this embodiment, filtered ECG signals are electrically communicated to a Holter or event recording device 1601 via cable 1605.

In one embodiment, two off-board electrodes 1603 are electrically connected to TAMD 1602 via connection wires 1604 and 1609. Snap 1606 serves to mechanically secure TAMD 1602 to the subject and also provides for electrical connection from electrode 1607 to the front-end electronics of TAMD 1602. Incorporating snap 1606 directly into the TAMD 1602 and packaging TAMD 1602 in a small, thin, and lightweight package can be useful for avoiding the need for monitored subject 1608 to wear a strap around the neck or use a belt clip to secure TAMD 1602 to subject 1608. These package characteristics allow electrode 1607 to both hold TAMD 1602 in place and electrically connect TAMD 1602 to electrode 1607. This may be useful for improving comfort and convenience of subject 1608 by eliminating the need for a third electrode wire, such as 1604 and 1609 and also by eliminating the need for a different means of securing the device such as a string around the neck or belt clip. This arrangement may also be useful by providing the subject comfort and convenience in combination with high quality ECG recordings that result from a relatively wide electrode spacing.

In some embodiments, such high quality ECG recordings are achieved in such a small package as facilitated by the use of denoising approaches described herein and/or in the underlying patent documents to which priority is claimed, which can be effected with relatively low processing overhead and power, via compact circuitry with a relatively small battery. In connection with such embodiments, it has been recognized/discovered that the use of such denoising approaches can facilitate the ability to render such functionality in a small package that is comfortably wearable and supported by a single electrode.

Figure 17:
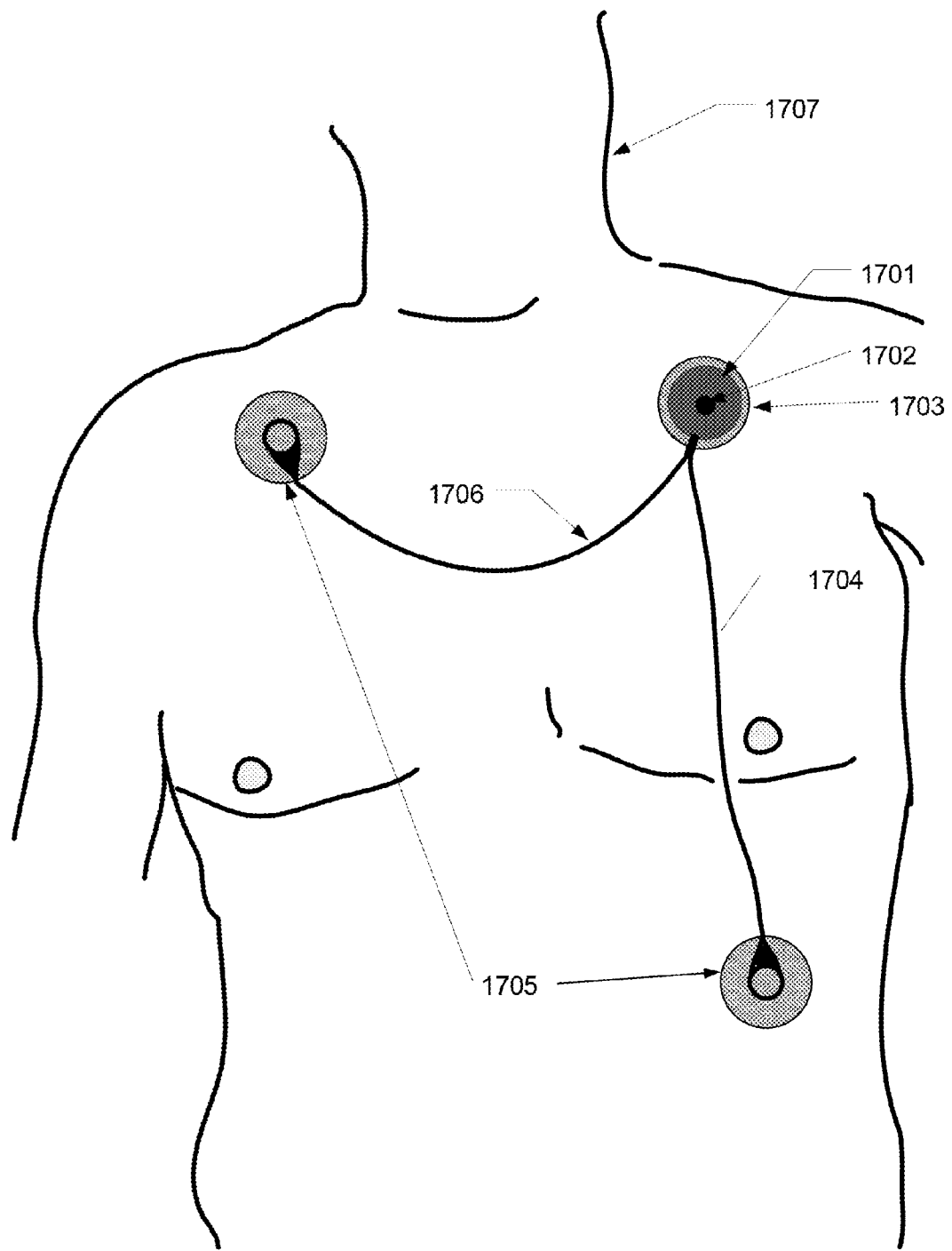
FIG. 17 shows another apparatus for recording ECG signals, in accordance with another example embodiment.

In another embodiment, and referring to FIG. 17, TAMD 1701 is configured as a two-lead Holter device. It processes a two-lead ECG to remove noise and stores the denoised (e.g., filtered) ECG in on-board memory. Data stored in memory can be communicated to DCRS 102 using a wired connection such as a USB interface or a wireless means such as RF or infrared communications. In one embodiment, the device is packaged in a small and lightweight housing of <15 cc in volume and <15 grams weight, and incorporates an ECG electrode snap 1702 on one side such that it can be attached directly to surface ECG electrode 1703 such as a 3M (St. Paul, Minn.) Model 2259.

In one embodiment, two off-board electrodes 1705 are electrically connected to TAMD 1701 via connection wires 1704 and 1706. Snap 1702 serves to mechanically secure TAMD 1701 to the subject and also provides for electrical connection from electrode 1703 to the front-end electronics of TAMD 1701. Incorporating snap 1702 directly into the TAMD 1701 and packaging TAMD 1701 in a small, thin, and lightweight package can be useful for avoiding the need for monitored subject 1707 to wear a strap around the neck or use a belt clip to secure TAMD 1701.

These package characteristics allow electrode 1703 to both hold TAMD 1701 in place and electrically connect TAMD 1701 to electrode 1703. This may be useful for improving comfort and convenience of subject 1707 by eliminating the need for a third electrode wire, such as 1704 and 1706 and also by eliminating the need for a different manner of securing the device such as a string around the neck or belt clip. This arrangement may also be useful by providing the subject comfort and convenience in combination with high quality ECG recordings that result from relatively wide electrode spacing.

Accordingly, various embodiments are directed to a patient-worn apparatus for recording an ECG from the patient, as may be implemented in a manner similar to that shown in FIG. 17. A first circuit (e.g., at 1701) digitizes an ECG signal obtained from the patient via at least two ECG leads (e.g., from 1703 and one or both of electrodes 1705). A computing circuit (e.g., also at 1701) decomposes the digitized ECG signal into subcomponents, computes a statistical variance of the subcomponents over a time interval (e.g., 10-60 seconds), and determines if one of the at least two ECG leads is disconnected from the patient based upon the statistical variance of the subcomponents. In some embodiments, the computing circuit generates a trigger alarm in response to determining that one of the at least two ECG leads is disconnected, and communicates the trigger alarm to at least one of the patient and a wireless communication circuit. In certain embodiments, the computing circuit operates in a low-power mode in response to determining that all of the at least two ECG leads are disconnected.

Referring to FIG. 21, a representative drawing of TAMD 1701 and 1602 is shown, as applicable to one or more embodiments. Snap 2101 provides for mechanical and electrical connection to an ECG electrode adhered to the patient's skin.

In one embodiment, snap 2101 is a standard size snap commonly used for ECG electrodes. Housing 2102 contains the electronic circuits of the TAMD. Battery cap 2103 provides access to the battery. In one embodiment, the cap is threaded and contains a rubber O-ring inside to protect moisture ingress. LEDs 2104 are used as indicators of operating status and alarms such as lead off.

In one embodiment, TAMD 101 is a Holter or event monitor and includes a subject activated symptom marker that places a mark in the data recording when activated. In one embodiment, TAMD contains at least one pair of sensors on opposite sides of the housing. When the subject squeezes the sides of the device together (e.g. by squeezing with thumb and index finger) the sensors detect that it is being squeezed and an event mark is triggered. In one embodiment the sensors are pressure sensors and the housing design is adapted for transmitting pressure from the subject's fingers through the wall of the housing to the sensor located inside the housing. In another embodiment, the sensors are capacitive sensors that sense that the subject has placed fingers on both sides of the device.

In some embodiments, TAMD 101 is operable for submerging in water without impact upon function. This can be accomplished in part by back-filling most of the enclosure with epoxy or similar material. The lining of the battery cap contains a rubber O-ring to provide a moisture seal. In some embodiments where communication of data is handled via a USB interface, a micro-USB communications port is located inside the device housing such that it is accessible when the screw-on battery cap is removed.

Some embodiments of TAMD 101 operate for detecting that one or more ECG electrodes are no longer making adequate contact to provide a good quality signal. In one embodiment, TAMD 101 provides a visual alarm such as a flashing LED. In another embodiment, TAMD 101 provides an audible alarm. In another embodiment, TAMD 101 contains an RF communication link such as Zigbee or Bluetooth and communicates to a receiving device such as a mobile phone, computer, or base station that one or more leads are in poor contact with the skin. The receiving device is programmed to communicate an appropriate message to one or more of a monitoring service center, the cell phone of the subject wearing the device, or the cell phone of a friend, relative, or caretaker of the subject. The person or persons receiving the message can then take appropriate action to correct the issue.

In another embodiment TAMD 101 employs a bidirectional communication link that allows a device with Bluetooth capability such as a smart phone or computer to communicate setup and configuration information to TAMD 101. Such information communicated may include sampling rate, parameters to be extracted from the ECG, and patient/subject information. This may also provide the capability to interrogate device status such as remaining battery life and the portion of time that a good quality signal has been recorded.

In other embodiments TAMD 101 incorporates a "leads connected" mode that automatically assesses the quality of the signal received from the electrodes. In some embodiments TAMD 101 evaluates the quality of the ECG by determining whether QRS complexes are detected with sufficient regularity and frequency. If the quality of the signal is good, the system communicates that the ECG electrodes are connected. If it senses that the electrodes are not connected, an alarm is issued. Based upon the signal quality, the device illuminates a specific LED on the device or wirelessly communicates a message indicating signal quality to a device located away from TAMD 101.

In some embodiments TAMD 101 includes a communication circuit that wirelessly streams the ECG signal to a Bluetooth device such as a smart phone, computer, or any device having the ability to receive Bluetooth signals and display them. In some embodiments, this feature is enabled for a short time by a person operating TAMD 101. This can be done by pressing one or more controls on TAMD 101 or remotely via a command from a Bluetooth device in communication with TAMD 101. This feature can be useful to confirm that the electrodes have been placed on the subject properly and the device is acquiring data appropriately.

In some embodiments TAMD 101 enters a low-power (sleep) mode if no ECG signal is sensed or if a poor quality signal is sensed from the electrodes. If, after a period of time (sensing time), the device determines that it is not connected to a patient TAMD 101 goes into a low power mode for a sleep time to reduce battery drain. Following expiration of the sleep time, the device wakes up and evaluates the input signal for a time equal to sensing time to determine if it is connected to a patient. If a signal is identified, the device stays on for a time interval of at least as long as the operating time interval. In some embodiments, operating time is significantly longer than the sensing time. During the operating time, the system continues to evaluate the input signal for a valid ECG. If a valid ECG is detected the timer for the operating time interval is reset. If the device mode is in operating mode and no valid signal is found over the course of the operating time interval, the device enters the sleep mode and periodically wakes up to assess whether a signal is present. In one embodiment, the sensing time interval is 10 to 60 seconds, the sleep time interval is 30 seconds to 5 minutes, and operating time interval is 5 minutes to 30 minutes. In one embodiment evaluating the input signal to determine if it is connected to a patient includes measuring: whether shifts in baseline are occurring, the incidence of QRS complexes, and the character of noise. In another embodiment the morphology of any detected QRS complexes is evaluated to confirm they are real.

Figure 18:
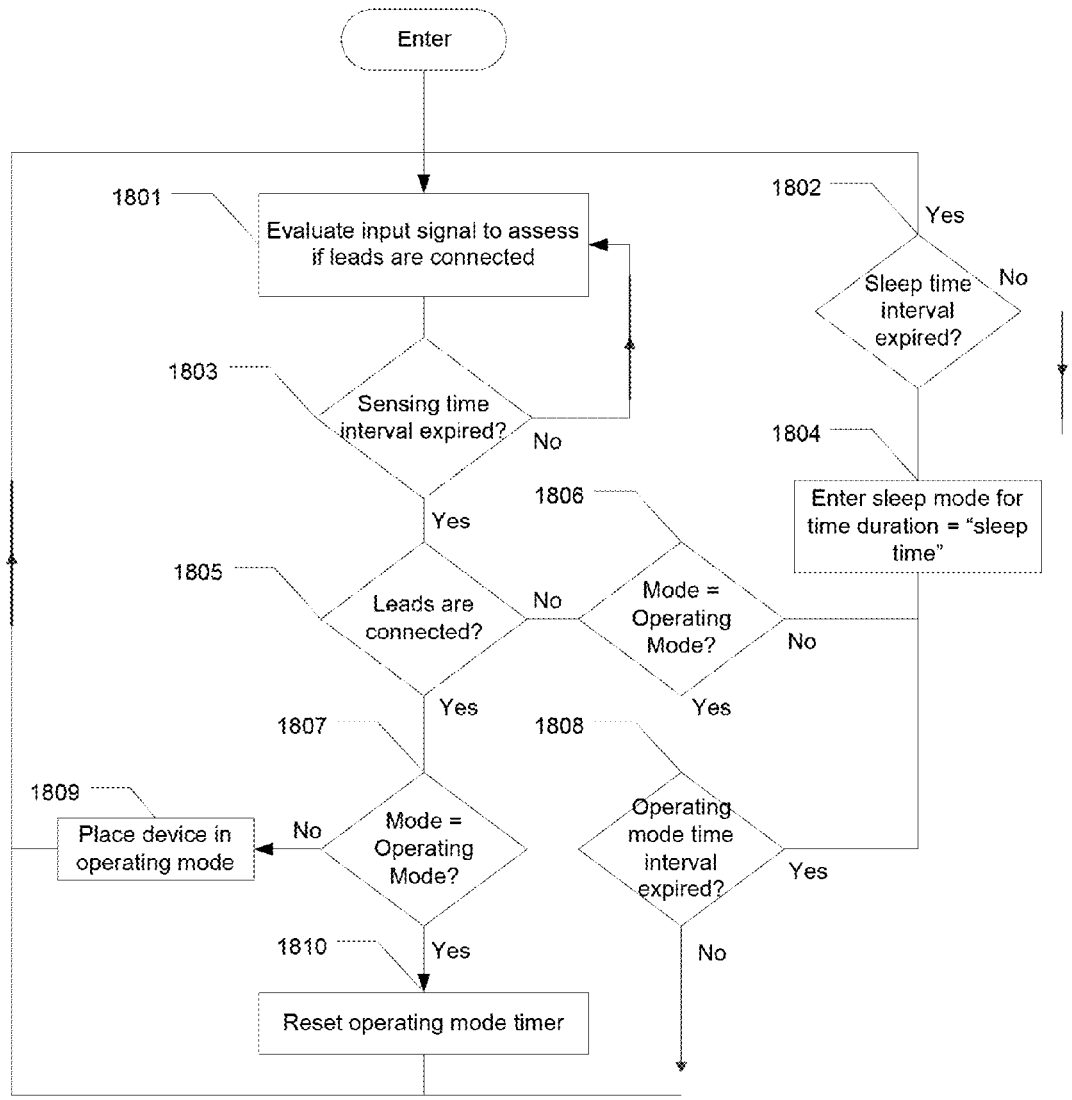
FIG. 18 shows a block diagram for a method of recording ECG signals, in accordance with another example embodiment.

In one embodiment, referring to FIG. 18, TAMD 101 executes a number of steps to determine whether the ECG sensing leads are connected and whether the device should enter low-power mode. FIG. 18 employs three time intervals including a sensing time interval during which the device is evaluating the input signal to determine if the leads are connected to the patient, an operating mode time interval during which the device is processing the input signal normally, and a sleep time interval during which the device is in a low-power mode to reduce battery power drain. Once the device enters an operating mode, it remains in that mode for at least the duration of the operating mode time interval. No signals are evaluated when in low-power mode (sleep mode). When the low-power mode expires, the device wakes up and looks for the presence of a signal for the duration of the sensing time interval.

In step 1801 the ECG signal is evaluated for a segment of time (the sensing time interval) to determine if a signal is present and hence whether the leads are connected to a patient. In one embodiment of step 1801, MDSP techniques as described and/or incorporated herein are used to identify whether an ECG is present. This involves decomposing the input ECG signal into subcomponents and computing statistical variance of subcomponents for the duration of the sensing time interval. In one embodiment each subcomponent center frequency corresponds to a particular frequency band of the input signal. The distribution of the variance of subcomponents (e.g., the variance of individual subcomponents over the sensing time interval) approximates the power spectral density function of the input signal.

Figure 19:
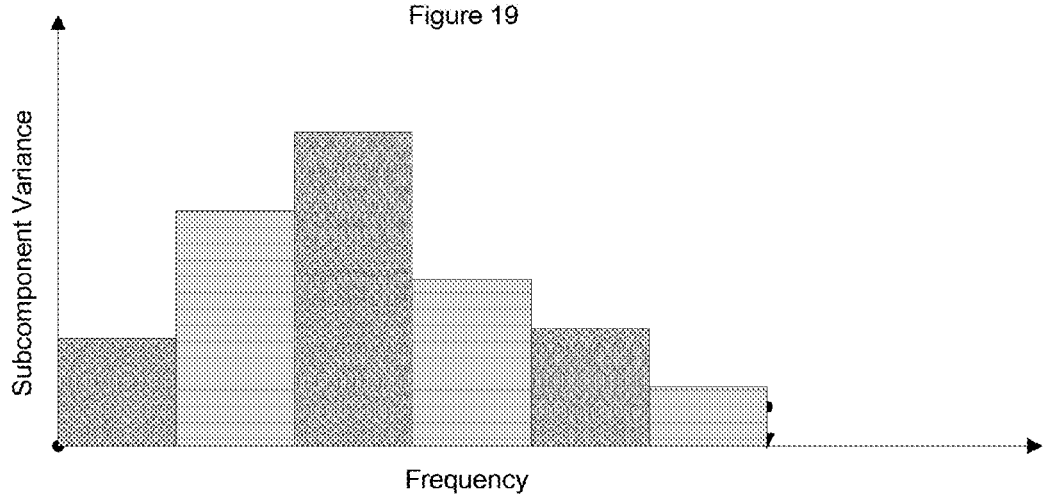
FIG. 19 shows a plot of subcomponent variance as implemented with one or more example embodiments.
Figure 20:
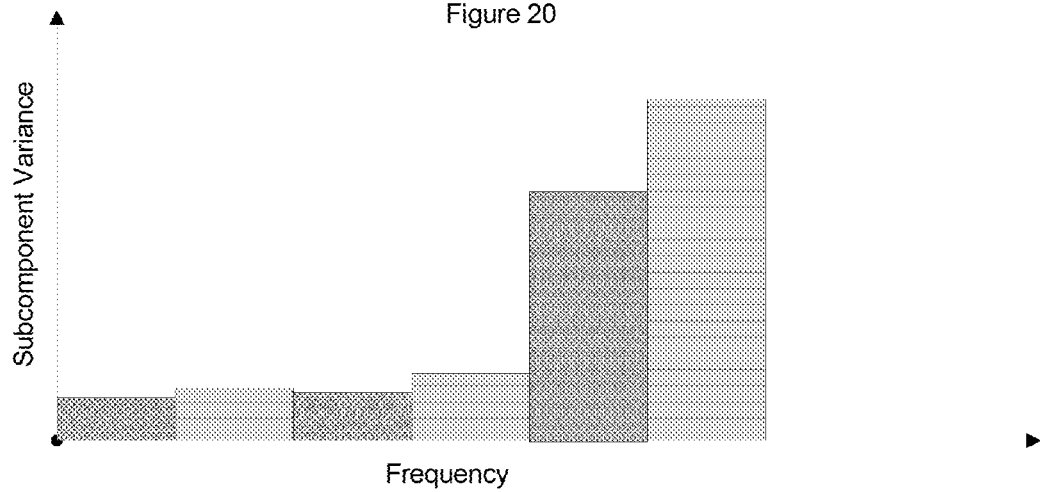
FIG. 20 shows another plot of subcomponent variance as implemented with one or more example embodiments.

FIGS. 19 and 20 provide examples of the distribution of subcomponent variance when an ECG signal is present (FIG. 19) and when the sensing electrodes are not connected (FIG. 20), in accordance with respective embodiments. Approaches for evaluating the distribution of subcomponent variance include identifying which subcomponent has the highest variance, and comparing the profile of the distribution of subcomponent variance to a profile of a known condition of the sensing leads. This technique can be applied to the signals from individual leads to determine if a single lead is disconnected, and is an alternative to using the traditional impedance measurement approach. The approach described here for step 1801 can be useful in that it can be implemented with very little power and uses fewer hardware components than traditional methods to sense lead off and hence can result in a smaller and less expensive device.

At step 1803, a timer is used to determine when the sensing time interval has been completed. Step 1805 evaluates the result of the assessment of the input signal in step 1801 to determine if leads are connected. If leads are connected, then flow is directed to the operating mode at 1807 where the mode of TAMD 101 is queried. If the device is currently in the operating mode, the operating mode timer is reset at 1810 to assure that the device will remain in operating mode for at least the duration of the operating time. If the device is found to not be in the operating mode at 1807, the device is placed in the operating mode at 1809 and continues to step 1801 to assess whether the leads are connected to the patient.

If, at 1805 it is found that the leads are not connected, flow is directed to assessing the mode in step 1806. If the device is determined to be in operating mode at step 1806, the operating mode timer is interrogated at 1808 to determine if operating mode time interval has expired. If it has expired, then flow is directed to 1804 and the device is placed in sleep mode. If the operating mode timer has not expired, flow is directed to 1801 to assess whether the lead is off. If it is found that the device is not in operating mode in step 1806, flow is directed to 1804 and the device is placed in sleep mode. Once the device has been placed in sleep mode in 1804, it remains in that mode until the sleep time timer has expired. Once the sleep time has been determined as having expired at step 1802, flow is directed to 1801.

REFERENCES CITED

For general information regarding a variety of fields that may relate to one or more embodiments of the present invention, and for specific information regarding the application of one or more such embodiments, reference may be made to the following documents, which are fully incorporated herein by reference. Various ones of these references are further cited above via corresponding numerals, and may be implemented as such.

1. N V Thakor, Y S Zhu. Applications of adaptive filtering to ECG analysis: noise cancellation. IEEE Transactions on Biomedical Engineering, 1991, vol. 38, no 8, pp. 785-794
2. R Sameni, M B Shamsollahi, C Jutten, M Babaie-Zadeh. Filtering Noisy ECG Signals Using the Extended Kalman Filter Based on a Modified Dynamic ECG Model. Computers in Cardiology 2005
3. Donoho, D. L., "Denoising by soft-thresholding," IEEE Trans. on Inf. Theory, 42 3, pp. 613-627, 1995
4. K. R. Rao and P. Yip, *Discrete Cosine Transform: Algorithms, Advantages, Applications* San Diego, Calif.: Academic, 1990.

5. Mallat, S. G., and Zhang, Z., Matching Pursuits with Time-Frequency Dictionaries, IEEE TSP(41), No. 12, December 1993, pp. 3397-3415.
6. J. Woods. Subband Coding, Kluwer Academic Press, 1990.
7. K. S. Ball, L. Sirovich, L. R. Keefe, Dynamical eigenfunction decomposition of turbulent channel flow. International Journal for Numerical Methods in Fluids Volume 12, Issue 6, Date: 5 Apr. 1991, Pages: 585-604
8. Lipponen J, Tarvainen M, Laitinen T, Lyyra-Laitinen T, Karjalainen P. A Principal Component Regression Approach for Estimation of Ventricular Repolarization Characteristics. IEEE Trans Biomed Eng. 2010 vol. 57 no. 5 pp. 1062-1069
9. L. Smith A tutorial on Principal Components Analysis, http://users.ecs.soton.ac.uk/hbr03r/pa037042.pdf
10. Aminghafari, M.; Cheze, N.; Poggi, J-M. (2006), "Multivariate de-noising using wavelets and principal component analysis," *Computational Statistics & Data Analysis,* 50, pp. 2381-2398
11. P. Comon, "Independent component analysis, a new concept?," Signal Process. Special Issue on Higher Order Statistics, vol. 36, no. 3, pp. 287-314, 1994..
12. L. K. Saul and J. B. Allen, "Periodic component analysis: An eigenvalue method for representing periodic structure in speech," in NIPS, [Online]. 2000, pp. 807-813. Available: http://www.cs.cmu.edu/Groups/NIPS/00papers-pub-on-web/SaulAllen.pdf
13. R Sameni, et. al. Multichannel electrocardiogram decomposition using periodic component analysis. IEEE Transactions on Biomedical Engineering, 2008 vol 55, no 8 pp 1935-1940
14. Mallat, S. and Zhong, S. 1992. Characterization of Signals from Multiscale Edges. IEEE Trans. Pattern Anal. Mach. Intell. 14, 7 (July 1992),
15. Mallat, S. G., Hwang, W. L., Singularity Detection and Processing with Wavelets, IEEE Transactions on Information Technology (38), 1991, pp. 617-643.
16. Xu, Yansun, et. al. Wavelet transform domain filters: a spatially selective noise filtration technique, IEEE transactions on image processing 1994, vol. 3, no 6, pp. 747-758
17. G. Moody, W. Muldrow, and R. Mark, A noise stress test for arrhythmia detectors, Computers in Cardiology, 1984, pp. 381-384.
18. American National Standard ANSI/AAMI EC57:1998, Testing and Reporting Performance Results of Cardiac Rhythm and ST Segment Measurement Algorithms.
19. U.S. Pat. No. 5,817,027, P. Arand, W. Post. Method and apparatus for classifying heartbeats in an ECG waveform
20. Michaud G F, Li Q, Costeas X, Stearns R, Estes M 3rd, Wang P J, Correlation waveform analysis to discriminate monomorphic ventricular tachycardia from sinus rhythm using stored electrograms from implantable defibrillators. *PACE.* 1999 August;22(8):1146-51.
21. O. Adeyemi, et. al. QA interval as an indirect measure of cardiac contractility in the conscious telemeterised rat: Model optimisation and evaluation. Journal of Pharmacological and Toxicological Methods. 60 (2009) 159-166
22. Rusen Yang, Yong Qin, Cheng Li, Guang Zhu, Zhong Lin Wang Converting Biomechanical Energy into Electricity by a Muscle-Movement-Driven Nanogenerator Nano Letters 2009 9 (3), 1201-1205
23. C Taswell, "The What, How, and Why of Wavelet Shrinkage Denoising," Computing in Science and Engineering, vol. 2, no. 3, pp. 12-19, 2000
24. R. Brychta, Wavelet analysis of autonomic and cardiovascular signals, PhD Dissertation. Vanderbilt University, 2006
25. M. Haugland, Th. Sinkjaer. Cutaneous whole nerve recordings used for correction of footdrop in hemiplegic man, IEEE Transactions on Rehabilitation Engineering, vol3, no 4. 1995
26. M. L. Hilton. Wavelet and wavelet packets compression of electrocardiogram. IEEE Transactions on Biomedical Engineering, 44(5):394-402, May 1997.
27. Z. Lu, D. Y. Kim, and W. A. Pearlman. Wavelet compression of ECG signals by the set partitioning in hierarchical trees algorithm. IEEE Transactions on Biomedical Engineering, 47(7):849-856, July 2000.
28. S. C. Tai, C. C. Sun, and W. C. Tan, "2-D ECG compression method based on wavelet transform and modified SPIHT," IEEE Trans. Biomed. Eng., vol. 52, no. 6, pp. 999-1008, June 2005
29. Marcellin M., et. al, An Overview of JPEG-2000, Proc. of IEEE Data Compression Conference, pp. 523-541, 2000.
30. R Sameni, et. al. A nonlinear Bayesian filtering framework for ECG denoising. IEEE transactions on biomedical engineering, vol 54, n012, pp 2172-2185, 2007
31. K. Sayood, Introduction to Data Compression, Academic Press 2000.

Based upon the above discussion and illustrations, those skilled in the art will readily recognize that various modifications and changes may be made to the present invention without strictly following the exemplary embodiments and applications illustrated and described herein. Such modifications and changes may include, for example, incorporating one or more aspects described in the cited references priority documents, and/or applying one or more embodiments thereto, or combining embodiments. These and other modifications do not depart from the true spirit and scope of the present invention, including that set forth in the claims.

What is Claimed is:

1. An apparatus comprising:
at least two ECG sensing electrodes configured and arranged to adhere to remote locations on a patient and to sense ECG signals from the patient;
a digitizing circuit configured and arranged to digitize the ECG signals to provide digitized ECG signals;
a computing circuit configured and arranged to process the digitized ECG signals by reducing in-band noise as measured by the ANSI/AAMI EC57:1998 standard by at least 20 dB with a Quality of Signal Reconstruction of >95%;
a housing that houses the digitizing circuit and the computing circuit;
a fastener configured and arranged to mechanically fasten the housing to a first one of the ECG sensing electrodes and to electrically couple the first one of the ECG sensing electrodes to the digitizing circuit; and
for each additional one of the at least two ECG sensing electrodes that is in addition to the first one of the ECG sensing electrodes, a flexible insulated lead wire configured and arranged to couple the additional ECG sensing electrode to the digitizing circuit.

2. The apparatus of claim 1, wherein the fastener is configured and arranged to mechanically connect the housing to a first one of the ECG sensing electrodes by affixing the housing to the first one of the ECG sensing electrodes, wherein the computing circuit is configured and arranged to
remove noise from the digitized ECG signals while maintaining morphology of the digitized ECG signal, therein providing denoised ECG signals, and
process the denoised ECG signals by carrying out a function selected from the group consisting of: detecting an R-R interval, detecting a Q-T interval, detecting a QRS complex, and a combination thereof.

3. The apparatus of claim 1, further including a battery configured and arranged to power the digitizing and computing circuits, wherein the housing also houses the battery, and wherein the first one of the ECG sensing electrodes is configured and arranged to adhere to the patient and to support the entire weight of the housing via the fastener.

4. The apparatus of claim 1, further including an adhering component configured and arranged to adhere and fully support the first one of the ECG sensing electrodes and the housing to the skin of a patient.

5. The apparatus of claim 1, wherein each ECG signal is sampled at 300 Hz or less and the computing circuit is configured and arranged to reduce the in-band noise using an average power consumption that is less than 500 micro-Watts per ECG signal.

6. The apparatus of claim 1 wherein the housing has an average thickness of less than 12 mm and a volume of less than 18 cc.

7. The apparatus of claim 1, wherein the housing includes the first one of the electrodes.

8. The apparatus of claim 1, wherein the housing includes the fastener.

9. The apparatus of claim 1 wherein the flexible insulating lead wires are >10 cm in length.

10. The apparatus of claim 1 wherein the flexible insulating lead wires are >15 cm in length.

11. The apparatus of claim 1 wherein the flexible insulating lead wires are <3 mm diameter.

12. The apparatus of claim 1 further including a coin cell battery configured and arranged to power the digitizing and computing circuits, wherein the housing has a battery compartment configured and arranged to hold the coin cell battery and couple power from the battery to the digitizing and computing circuits, the battery compartment having a threaded cap configured and arranged to secure the coin cell battery therein.

13. The apparatus of claim 1, wherein the digitizing circuit includes an amplifier circuit configured and arranged to amplify the sensed ECG signals to provide amplified ECG signals for digitizing.

14. An apparatus comprising:
at least two ECG sensing electrodes configured and arranged to adhere to remote locations on a patient and to sense ECG signals from the patient;
a digitizing circuit configured and arranged to digitize the ECG signals to provide digitized ECG signals;
a computing circuit configured and arranged to process each digitized ECG signal by
decomposing the signal into subcomponents;
identifying a location of the QRS complex of a cardiac cycle in the ECG signal;
identifying a first time window in the cardiac cycle that includes the QRS complex;
identifying at least one time window in the cardiac cycle that does not include the QRS complex;
for each of the identified time windows, identifying target subcomponents as subcomponents that contain more energy that is within the band of frequencies characteristic of a desired ECG signal in the time window than energy that is outside the band of frequencies of the desired ECG signal; and
reconstructing a denoised physiological signal using at least two of the identified target subcomponents;
a housing that houses the digitizing circuit and the computing circuit;
a fastener configured and arranged to mechanically fasten the housing to a first one of the ECG sensing electrodes and to electrically couple the first one of the ECG sensing electrodes to the digitizing circuit; and
for each additional one of the at least two ECG sensing electrodes that is in addition to the first one of the ECG sensing electrodes, a flexible insulated lead wire configured and arranged to couple the additional ECG sensing electrode to the digitizing circuit.

15. A patient-worn apparatus for recording an ECG from the patient, the apparatus comprising:
a first circuit configured and arranged to digitize an ECG signal obtained from the patient via at least two ECG leads; and
a computing circuit connected to the first circuit to receive the digitized ECG signal, the computing circuit being configured and arranged to
decompose the digitized ECG signal into subcomponents,
compute a statistical variance of the subcomponents over a time interval, and
determine if one of the at least two ECG leads is disconnected from the patient based upon the statistical variance of the subcomponents.

16. The apparatus of claim 15, wherein the computing circuit is configured and arranged to generate a trigger alarm, in response to determining that one of the at least two ECG leads is disconnected, and to communicate the trigger alarm to at least one of the patient and a wireless communication circuit.

17. The apparatus of claim 15, wherein the computing circuit is configured and arranged to determine if all of the at least two ECG leads are disconnected and, in response to determining that all of the at least two ECG leads are disconnected, operate the apparatus in a low-power mode.

18. The apparatus of claim 15, wherein the time interval ranges from 10 seconds to 60 seconds.

19. The apparatus of claim 15, further including determining if at least one of the at least two leads is in poor contact with the patient based on the computed statistical variance.

20. An apparatus comprising:
a first sensing electrode configured and arranged to adhere to a patient and to sense physiological signals from the patient;
a denoising component coupled to the first sensing electrode and configured and arranged to receive the sensed physiological signals via the coupling to the first sensing electrode and coupling to a second sensing electrode, the denoising component including
a digitizing circuit configured and arranged to digitize the signals,
a computing circuit configured and arranged to process the digitized signals to remove noise therefrom while maintaining morphology of the physiological signals by reducing in-band noise as measured by the ANSI/AAMI EC57:1998 standard by at least 20 dB with a Quality of Signal Reconstruction of >95%,
a battery configured and arranged to power the digitizing and computing circuits, and
a housing configured and arranged to house the battery, digitizing circuit and computing circuit; and
a fastener configured and arranged to mechanically fasten the housing to the first sensing electrode, the first sensing electrode being configured and arranged to support the weight of the denoising component via the fastener while the first sensing electrode is adhered to the patient.

21. An apparatus comprising:
at least two ECG sensing electrodes configured and arranged to adhere to remote locations on a patient and to sense ECG signals from the patient;
a digitizing circuit configured and arranged to digitize the ECG signals to provide digitized ECG signals;
a computing circuit configured and arranged to:
 decompose the digitized ECG signal into subcomponents,
 compute a statistical variance of the subcomponents over a time interval, and
 determine if one of the at ECG sensing electrodes is disconnected from the patient based upon the statistical variance of the subcomponents;
a housing that houses the digitizing circuit and the computing circuit;
a fastener configured and arranged to mechanically fasten the housing to a first one of the ECG sensing electrodes and to electrically couple the first one of the ECG sensing electrodes to the digitizing circuit; and
for each additional one of the at least two ECG sensing electrodes that is in addition to the first one of the ECG sensing electrodes, a flexible insulated lead wire configured and arranged to couple the additional ECG sensing electrode to the digitizing circuit.

* * * * *

UNITED STATES PATENT AND TRADEMARK OFFICE
CERTIFICATE OF CORRECTION

PATENT NO. : 9,339,202 B2  
APPLICATION NO. : 13/931228  
DATED : May 17, 2016  
INVENTOR(S) : Brockway et al.

Page 1 of 1

It is certified that error appears in the above-identified patent and that said Letters Patent is hereby corrected as shown below:

In the Specification

Column 1 Line 27 Please insert the following after the Title:
--STATEMENT REGARDING FEDERALLY SPONSORED RESEARCH AND DEVELOPMENT
This invention was made with government support under HL110739 and DA041815 awarded by the National Institutes of Health.--

Signed and Sealed this
Twenty-third Day of June, 2020

Andrei Iancu
*Director of the United States Patent and Trademark Office*